US010364466B2

(12) United States Patent
Bais et al.

(10) Patent No.: US 10,364,466 B2
(45) Date of Patent: Jul. 30, 2019

(54) BIOLOGICAL MARKERS FOR IDENTIFYING PATIENTS FOR TREATMENT WITH VEGF ANTAGONISTS

(71) Applicant: Genentech, Inc., South San Francisco, CA (US)

(72) Inventors: Carlos Bais, San Francisco, CA (US); Matthew Brauer, San Francisco, CA (US); Mallika Singh, San Francisco, CA (US); Maike Schmidt, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 259 days.

(21) Appl. No.: 13/836,535

(22) Filed: Mar. 15, 2013

(65) Prior Publication Data

US 2014/0017233 A1    Jan. 16, 2014

Related U.S. Application Data

(63) Continuation-in-part of application No. PCT/US2013/021306, filed on Jan. 11, 2013.

(60) Provisional application No. 61/586,660, filed on Jan. 13, 2012.

(51) Int. Cl.
| *A61K 39/395* | (2006.01) |
| *C12Q 1/68* | (2018.01) |
| *G01N 33/53* | (2006.01) |
| *C12Q 1/6886* | (2018.01) |
| *A61K 45/06* | (2006.01) |
| *G01N 33/574* | (2006.01) |
| *C07K 16/22* | (2006.01) |
| *C12Q 1/6883* | (2018.01) |
| *A61K 39/00* | (2006.01) |

(52) U.S. Cl.
CPC ........ *C12Q 1/6886* (2013.01); *A61K 39/3955* (2013.01); *A61K 39/39558* (2013.01); *A61K 45/06* (2013.01); *C07K 16/22* (2013.01); *C12Q 1/6883* (2013.01); *G01N 33/574* (2013.01); *A61K 2039/505* (2013.01); *C12Q 2600/106* (2013.01); *C12Q 2600/158* (2013.01); *G01N 2333/475* (2013.01); *G01N 2800/52* (2013.01)

(58) Field of Classification Search
None
See application file for complete search history.

(56) References Cited

U.S. PATENT DOCUMENTS

| 2005/0170444 A1 | 8/2005 | Karumanchi et al. |
| 2006/0204951 A1 | 9/2006 | Folkman et al. |
| 2011/0117083 A1 | 5/2011 | Bais et al. |
| 2011/0151468 A1 | 6/2011 | Wu et al. |
| 2013/0022596 A1 | 1/2013 | Yan et al. |
| 2014/0099326 A1 | 4/2014 | Schmidt et al. |

FOREIGN PATENT DOCUMENTS

| KR | 2010/0112000 A | 10/2010 |
| WO | WO-2008/060777 A2 | 5/2008 |
| WO | WO-2008/088854 A2 | 7/2008 |
| WO | WO-2009/050014 A1 | 4/2009 |
| WO | WO-2010/006232 A1 | 1/2010 |
| WO | WO-2010/075420 A1 | 7/2010 |
| WO | WO-2011/008696 A2 | 1/2011 |
| WO | WO-2011/020049 A1 | 2/2011 |
| WO | WO-2011/088149 A2 | 7/2011 |
| WO | WO-2011/089101 A1 | 7/2011 |

OTHER PUBLICATIONS

Yang et al. (2008). Clin. Cancer Res. 14(18):5893-5899.*
Fiebig et al. (2008). Journal of Clinical Oncology. 26:14519.*
International Preliminary Report on Patentability for International Application No. PCT/US2013/021306, dated Jul. 15, 2014 (10 pages).
International Search Report for International Application No. PCT/US2013/021306, dated Mar. 27, 2013 (4 pages).
Cheadle et al., "Analysis of microarray data using Z score transformation," J Mol Diagn. 5(2):73-81 (2003).
Speers et al., "Novel strategies for the treatment of estrogen receptor-negative breast cancer," Annual Summary: U.S. Army Medical Research and Material Command, Apr. 2009, <http://www.dtic.mil/dtic/tr/fulltext/u2/a512945.pdf>, retrieved on Oct. 8, 2014 (300 pages).
U.S. Appl. No. 13/828,826, Yan et al.
U.S. Appl. No. 13/829,262, Yan et al.
U.S. Appl. No. 13/744,135, Andres et al.
U.S. Appl. No. 13/801,404, Andres et al.
U.S. Appl. No. 13/801,360, Andres et al.
U.S. Appl. No. 13/728,333, Delmar et al.
U.S. Appl. No. 13/801,628, Delmar et al.
U.S. Appl. No. 13/801,541, Delmar et al.
U.S. Appl. No. 13/728,411, De Haas et al.
U.S. Appl. No. 13/801,914, De Haas et al.
U.S. Appl. No. 13/801,923, De Haas et al.
U.S. Appl. No. 13/737,586, Delmar et al.
U.S. Appl. No. 13/802,003, Delmar et al.
U.S. Appl. No. 13/802,205, Delmar et al.
Anonymous, "Anti-human VEGF-A (#3C5)," CoaChrom Diagnostica Gmbh, Retrieved from the Internet: URL: <http://www.coachrom.com/docs/rel/101-M56.pdf> (2009).
van Cutsem et al., "Phase III trial of bevacizumab in combination with gemcitabine and erlotinib in patients with metastatic pancreatic cancer," *J Clinical Oncology* 27(13): 2231-2237 (2009).

(Continued)

Primary Examiner — Christine J Saoud
Assistant Examiner — Jon M Lockard
(74) Attorney, Agent, or Firm — Clark & Elbing LLP; Karen L. Elbing

(57) ABSTRACT

The invention provides methods and compositions to detect expression of one or more biomarkers for identifying and treating patients who are likely to be responsive to VEGF antagonist therapy. The invention also provides kits and articles of manufacture for use in the methods.

17 Claims, 24 Drawing Sheets
(18 of 24 Drawing Sheet(s) Filed in Color)

(56) References Cited

OTHER PUBLICATIONS

DePrimo et al., "Circulating protein biomarkers of pharmacodynamic activity of sunitinib in patients with metastatic renal cell carcinoma: modulation of VEGF and VEGF-related proteins," *J Translational Medicine* 5(32): 1-11 (2007).
Dowlati et al., "Cell adhesion molecules, vascular endothelial growth factor, and basic fibroblast growth factor in patients with non-small cell lung cancer treated with chemotherapy with or without bevacizumab—An Eastern Cooperative Oncology Group study," *Clinical Cancer Research* 14:1407-1412 (2008).
Duda et al., "Plasma soluble VEGFR-1 is a potential dual biomarker of response and toxicity for bevacizumab with chemoradiation in locally advanced rectal cancer," *The Oncologist* 15(6): 577-583 (2010).
El-Rayes et al., "A phase II study of bevacizumab, oxaliplatin, and docetaxel in locally advanced and metastatic gastric and gastroesophageal junction cancers," *Annals of Oncology* 21:1999-2004 (2010).
Ferrara, "Vascular endothelial growth factor as a target for anticancer therapy," *The Oncologist* 9(1): 2-10 (2004).
Ferrara et al., "Discovery and development of Bevacizumab, an anti-VEGF antibody for treating cancer," *Nature Reviews-Drug Discovery* 3: 391-400 (2004).
Fischer et al., "Anti-PIGF inhibits growth of VEGF(R)-inhibitor-resistant tumors without affecting healthy vessels," *Cell* 131: 463-475 (2007).
Hansel et al., "Expression of neutropilin-1 in high-grade dysplasia, invasive cancer, and metastases of the human gastrointestinal tract," *American Journal of Surgical Pathology* 28:347-356 (2004).
Jain et al., "αPIGF: a new kid on the antiangiogenesis block," *Cell* 131(3): 443-445 (2007).
Kang et al., "AVAGAST: A randomized, double blind, placebo-controlled, phase III study of first-line capecitabine and cisplatin plus bevacizumab or placebo in patients with advanced gastric cancer (AGC)," *Journal of Clinical Oncology* 28: 2 pages (2010) (Abstract).
Karayiannakis et al., "Serum vascular endothelial growth factor levels in pancreatic cancer patients correlate with advanced and metastatic disease and poor prognosis," *Cancer Letters* 194(1): 119-124 (2003).
Kim et al., "The vascular endothelial growth factor proteins: Identification of biologically relevant regions by neutralizing monoclonal antibodies," *Growth Factors* 7:53-64 (1992).
Kindler et al., "Phase II trial of bevacizumab plus gemcitabine in patients with advanced pancreatic cancer," *J Clinical Oncology* 23(31): 8033-8040 (2005).
Ko et al., "A phase II study evaluating bevacizumab in combination with fixed-dose rate gemcitabine and low-dose cisplatin for metastatic pancreatic cancer: is an anti-VEGF strategy still applicable?" *Investigational New Drugs; The Journal of New Anticancer Agents* 26(5): 463-471 (2008).
Longo et al., "Pancreatic cancer: from molecular signature to target therapy," *Critical Reviews in Oncology/Hematology* 68(3): 197-211 (2008).
Miles et al., "Phase III study of bevacizumab plus docetaxel compared with placebo plus docetaxel for the first-line treatment of human epidermal growth factor receptor 2-negative metastatic breast cancer," *Journal of Clinical Oncology* 28:3239-3247 (2010).
Ohtsu et al., "Bevacizumab in combination with chemotherapy as first-line therapy in advanced gastric cancer: A randomized, double-blind, placebo-controlled phase III study," *Journal of Clinical Oncology* 29:3968-3976 (2011).
Parr et al., "Placenta growth factor is over-expressed and has prognostic value in human breast cancer," *European Journal of Cancer* 41(18): 2819-2827 (2005).
Pircher et al., "Biomarkers in tumor angiogenesis and anti-angiogenic therapy," *International Journal of Molecular Sciences* 12:7077-7099 (2011).
R&D Systems, "Human VEGF antibody," Retrieved from the Internet: URL: <http://www.rndsystems.com/pdf/mab293.pdf> (2009).
Shah et al., "Multicenter phase II study of irinotecan, cisplatin, and bevacizumab in patients with metastatic gastric or gastroesophageal junction adenocarcinoma," *Journal of Clinical Oncology* 24:5201-5206 (2006).
Taylor et al., "Altered tumor vessel maturation and proliferation in placenta growth factor-producing tumors: potential relationship to post-therapy tumor angiogenesis and recurrence," *International Journal of Cancer* 105(2): 158-164 (2003).
Taylor et al., "Role of placenta growth factor in malignancy and evidence that an antagonistic PIGF/FIT-1 peptide inhibits the growth and metastasis of human breast cancer xenografts," *Mol Cancer Ther* 6(2): 524-531 (2007).
Wei et al., "Placenta growth factor expression is correlated with survival of patients with colorectal cancer," *Gut* 54(5): 666-672 (2005).
Yang et al., "Gene expression profile and angiogenic markers correlate with response to neoadjuvant bevacizumab followed by bevacizumab plus chemotherapy in breast cancer," *Clin. Can. Res.* 14(18): 5893-5899 (2008).
Office Action for U.S. Appl. No. 12/644,883, dated Mar. 30, 2012 (21 pages).
Examination Report for Australian Patent Application No. 2009329994, dated Jun. 26, 2012 (3 pages).
English Translation of Notice of Rejection for Japanese Patent Application No. 2011-542578, dated Oct. 24, 2012 (3 pages).
English Translation of Notice of Preliminary Rejection for Korean Patent Application No. 10-2011-7017228 (4 pages).
Office Action for Mexican Patent Application No. MX/a/2011/006875, dated Jul. 2, 2012 (5 pages).
Written Opinion for Singaporean Patent Application No. 201104627-3, dated Jul. 17, 2012 (9 pages).
International Search Report for PCT/US2009/069254, date of completion Feb. 23, 2010, dated Mar. 8, 2010 (2 pages).
International Search Report and Written Opinion for International Application No. PCT/EP2011/062231, dated Nov. 2, 2011 (13 pages).
International Search Report and Written Opinion for International Application No. PCT/EP2011/063932, dated Feb. 22, 2012 (17 pages).
International Search Report and Written Opinion for International Application No. PCT/EP2011/062226, dated Dec. 29, 2011 (13 pages).
International Search Report and Written Opinion for International Application No. PCT/EP2011/062232, dated Nov. 4, 2011 (12 pages).
Jubb et al., "Biomarkers to predict the clinical efficacy of bevacizumab in cancer," Lancet Oncol. 11(12):1172-83 (2010).
Reinmuth et al., "Current data on predictive markers for anti-angiogenic therapy in thoracic tumours," Eur Respir J. 36(4):915-24 (2010).
Whitlock et al., "Combining probability from independent tests: the weighted Z-method is superior to Fisher's approach," J Evol Biol. 18(5):1368-73 (2005).
Extended European Search Report for European Patent Application No. 13736138.2, dated Sep. 17, 2015 (7 pages).
Search Report for Singaporean Patent Application No. 11201403927X, dated Jun. 19, 2015 (9 pages).
Jahangiri et al., "Biomarkers predicting tumor response and evasion to anti-angiogenic therapy," Biochim Biophys Acta. 1825(1):86-100 (2012).
Notice of Reasons for Rejection for Japanese Patent Application No. 2014-552348, dated Oct. 18, 2016 (14 pages).
Examination Report for Australian Patent Application No. 2018200270, dated Nov. 7, 2018 (3 pages).

* cited by examiner

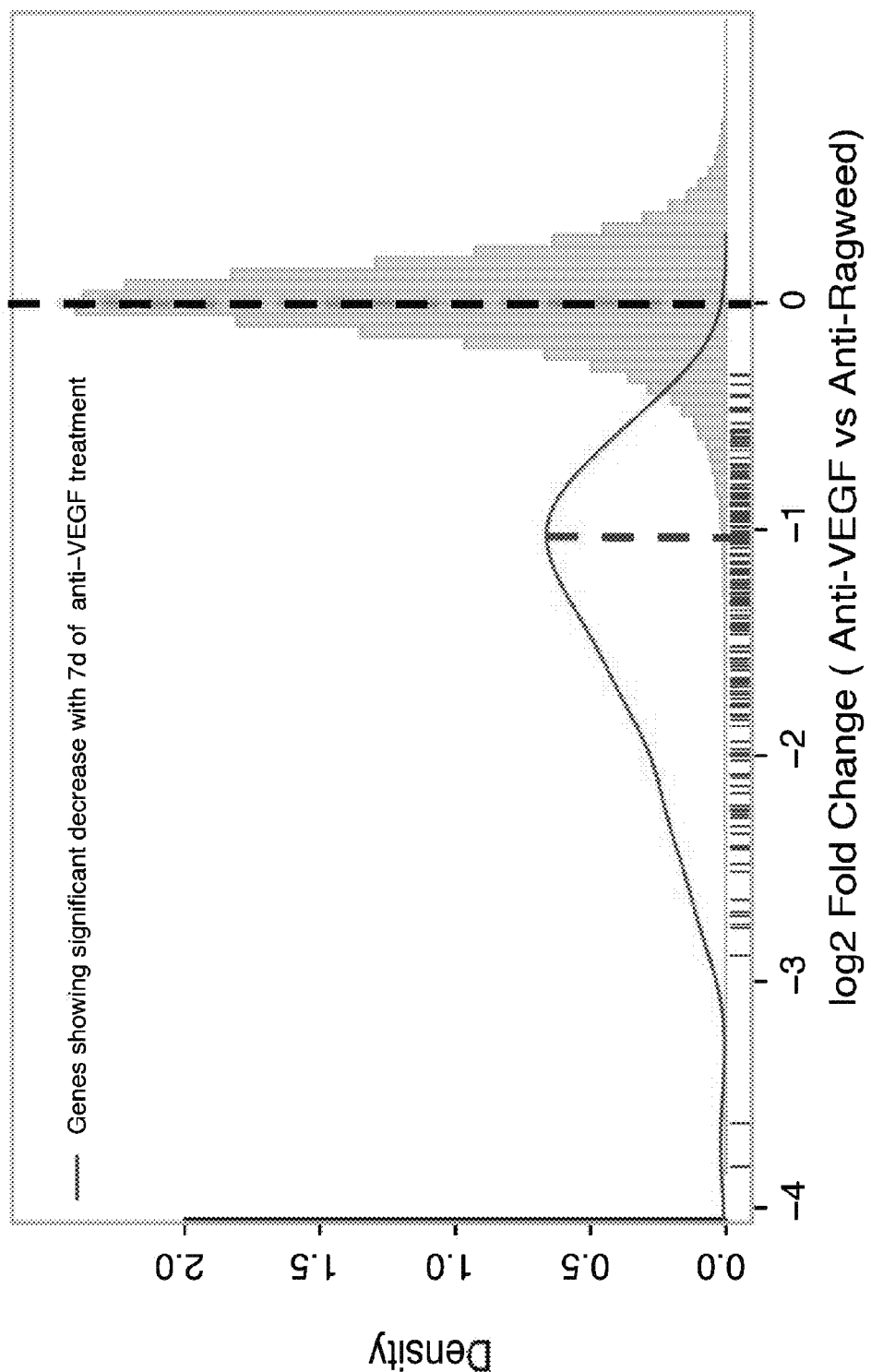

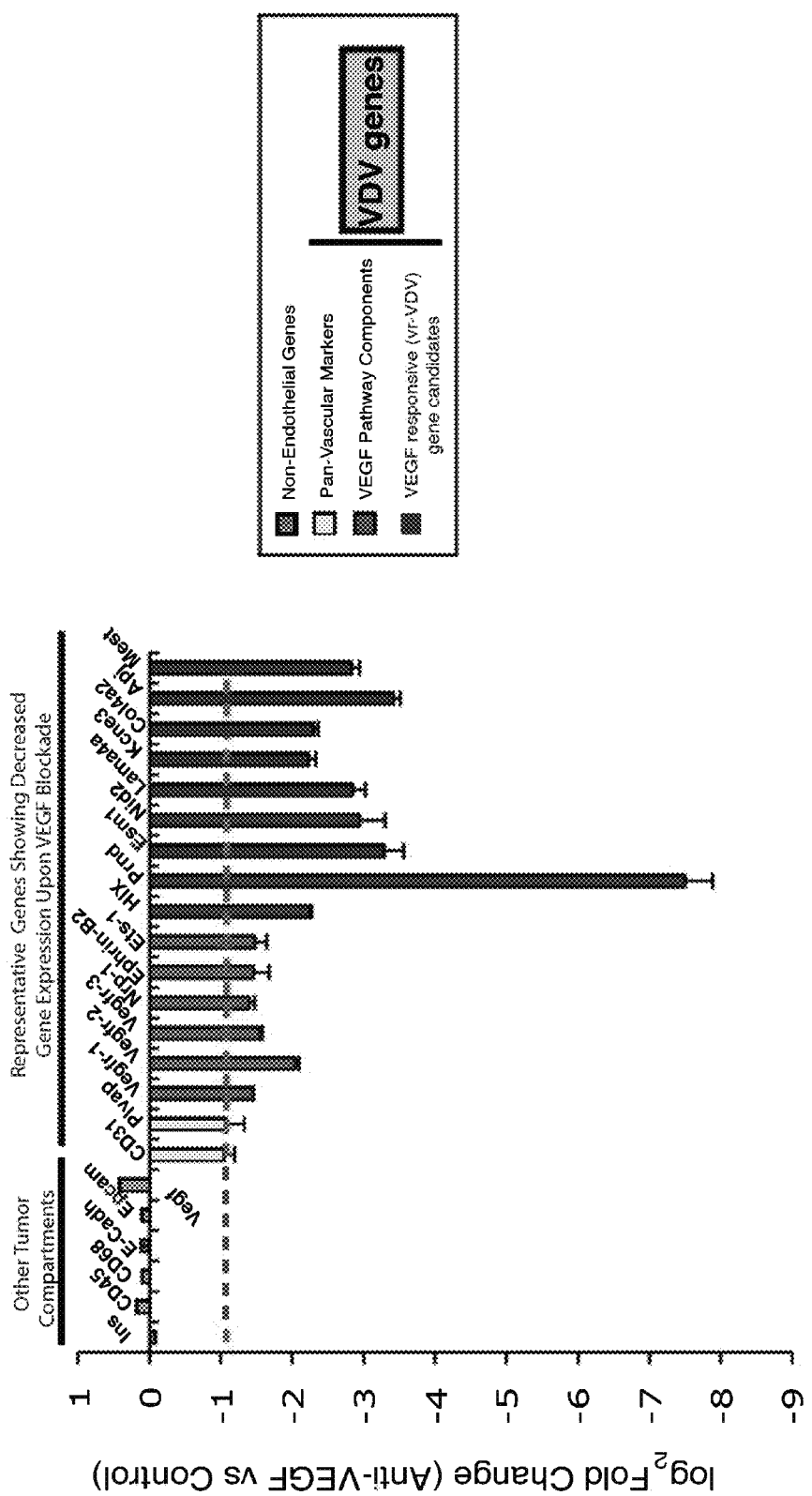

MDA-MB-231 Human breast cancer model
(Subcutaneous, 24 Hours of Treatment)

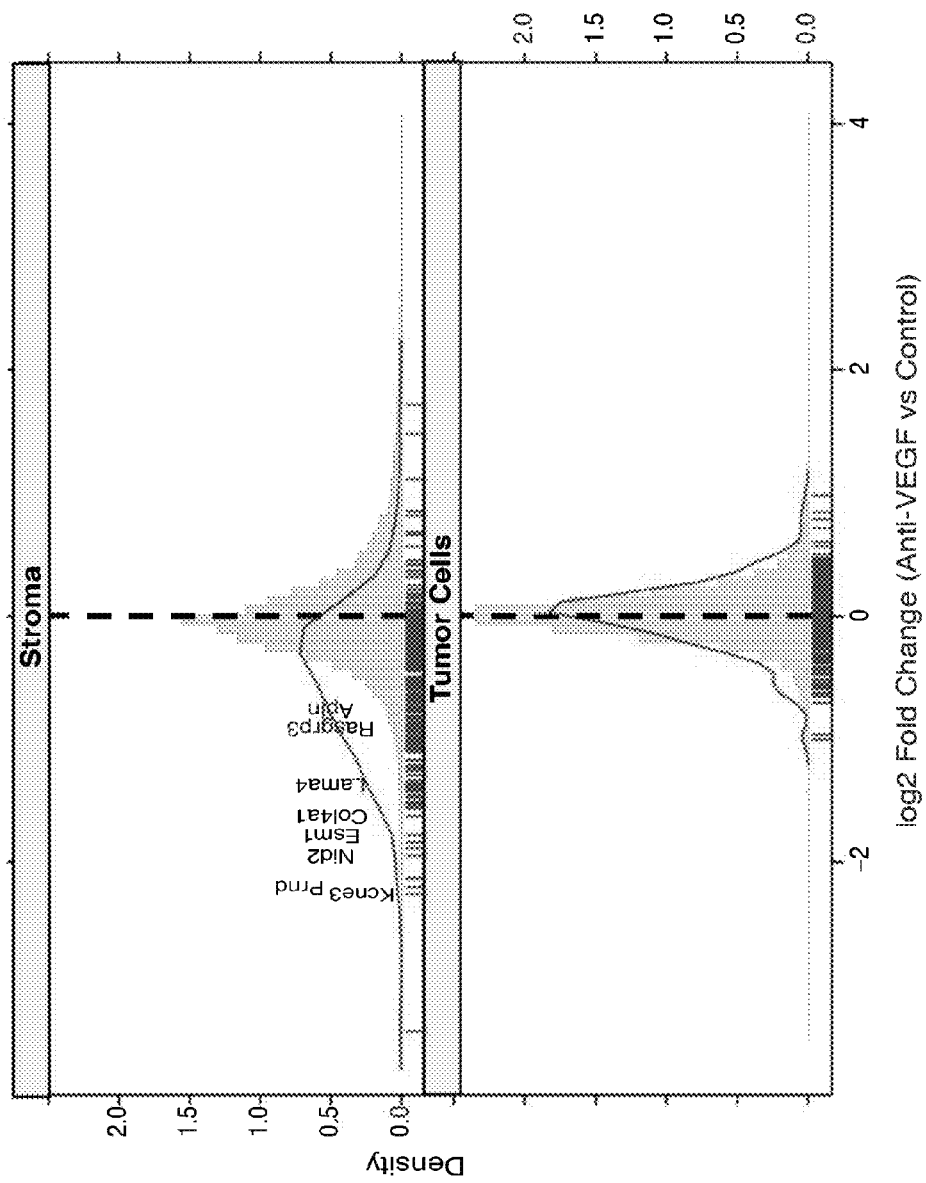

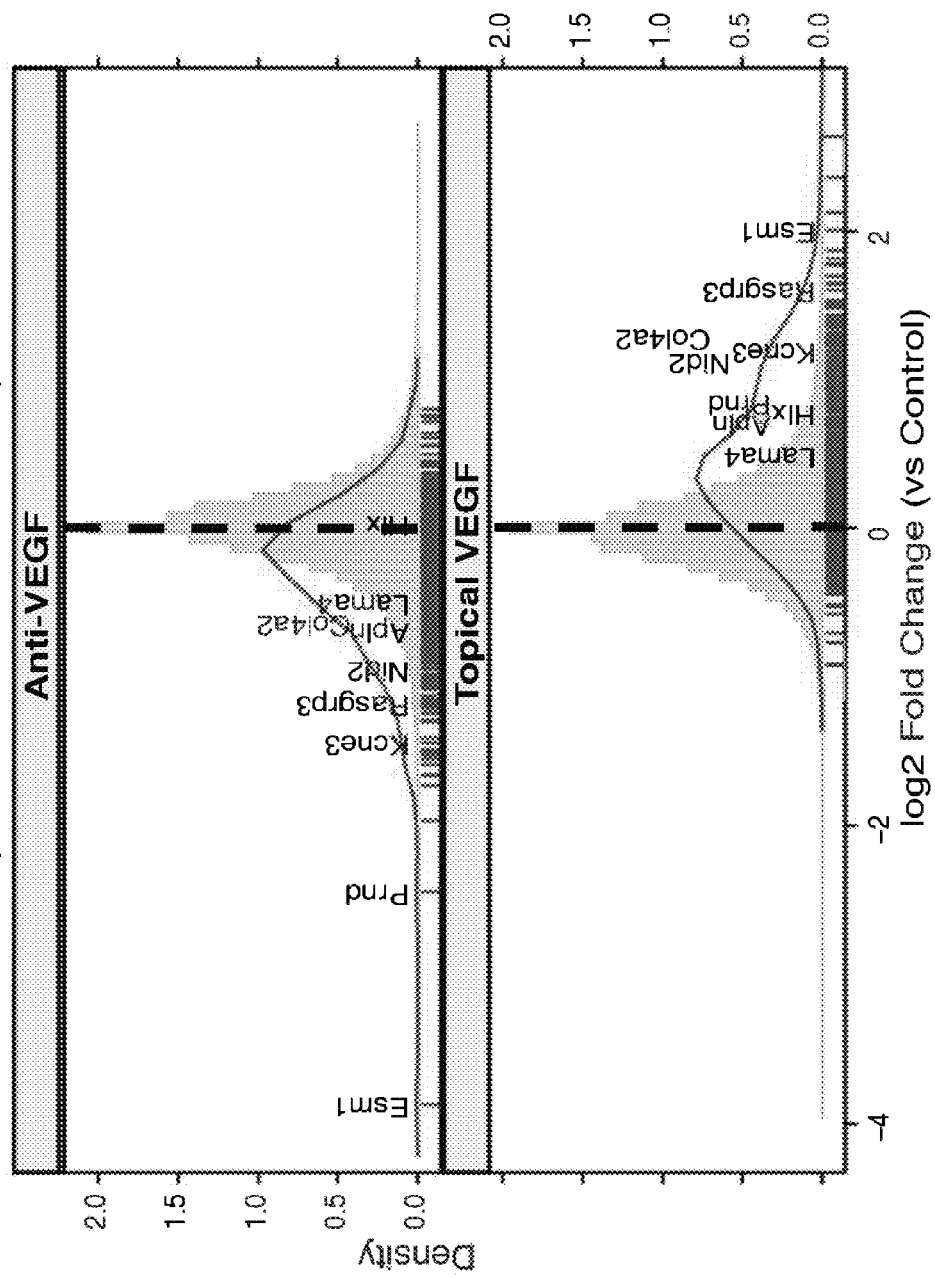

MDA-MB-231 tumor sections (72 hours post-treatment)

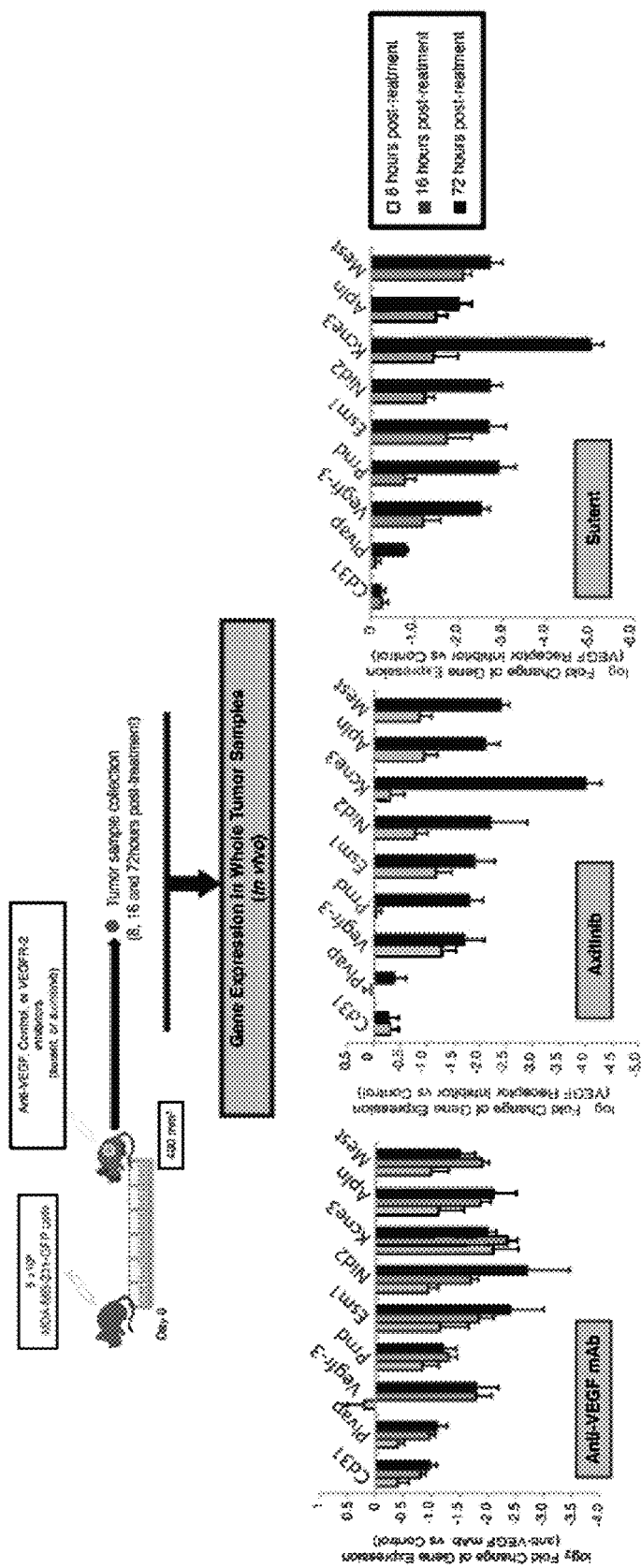

| | | HR | 95% CI | p-value |
|---|---|---|---|---|
| — XELOX<br>▬ XELOX + bev | VDV High | 0.36 | 0.17 to 0.77 | 0.0079 |
| --- XELOX<br>---- XELOX + bev | VDV Low | 0.88 | 0.47 to 1.62 | 0.67 |

| | | HR | 95% CI | p-value |
|---|---|---|---|---|
| — XELOX<br>▬ XELOX + bev | VDV High | 0.31 | 0.11 to 0.93 | 0.036 |
| --- XELOX<br>---- XELOX + bev | VDV Low | 0.58 | 0.25 to 1.33 | 0.2 |

BIOLOGICAL MARKERS FOR IDENTIFYING PATIENTS FOR TREATMENT WITH VEGF ANTAGONISTS

CROSS-REFERENCE TO RELATED APPLICATIONS

This application is a continuation-in-part of international application PCT/US2013/021306, filed Jan. 11, 2013, which claims priority from U.S. Application No. 61/586,660, filed Jan. 13, 2012, the contents of which are incorporated herein by reference.

FIELD OF THE INVENTION

The present invention is directed to methods for identifying patients that will benefit from treatment with a VEGF antagonist, e.g., an anti-VEGF antibody.

BACKGROUND OF THE INVENTION

Measuring expression levels of biomarkers (e.g., secreted proteins in plasma) can be an effective means to identify patients and patient populations that will respond to specific therapies including, e.g., treatment with VEGF antagonists, such as anti-VEGF antibodies.

There is a need for effective means for determining which patients will respond to which treatment and for incorporating such determinations into effective treatment regimens for patients with VEGF antagonist therapies, whether used as single agents or combined with other agents.

SUMMARY OF THE INVENTION

The present invention provides methods for identifying patients who will benefit from treatment with a VEGF antagonist, such as an anti-VEGF antibody. These patients are identified based on expression levels of the genes set forth in Table 1 or 2.

Accordingly, one embodiment of the invention provides methods of determining whether a patient is likely to respond to treatment with the VEGF antagonist, the methods comprising (a) detecting expression of at least one gene set forth in Table 1 or 2 in a biological sample obtained from the patient prior to any administration of a VEGF antagonist to the patient; (b) comparing the expression level of the at least one gene to a reference expression level of the at least one gene, wherein a change in the level of expression of the at least one gene in the patient sample relative to the reference level identifies a patient who is likely to respond to treatment with a VEGF antagonist; and, optionally, (c) informing the patient that they have an increased likelihood of being responsive to treatment with a VEGF antagonist. In some embodiments, the methods can instead optionally include (c) informing the patient that they do not have an increased likelihood of being responsive to treatment with a VEGF antagonist if, for example, no change in the level of expression of the at least one gene is detected in the patient sample relative to the reference level.

A further embodiment of the invention provides methods of optimizing therapeutic efficacy of a VEGF antagonist for a patient, the methods comprising (a) detecting expression of at least one gene set forth in Table 1 or 2 in a biological sample obtained from the patient prior to any administration of a VEGF antagonist to the patient; (b) comparing the expression level of the at least one gene to a reference expression level of the at least one gene, wherein a change in the level of expression of the at least one gene in the patient sample relative to the reference level identifies a patient who is likely to respond to treatment with a VEGF antagonist; and, optionally, (c) providing a recommendation to the patient that treatment include a VEGF antagonist. In some embodiments, the methods can instead optionally include (c) providing a recommendation to the patient that treatment is not a VEGF antagonist if, for example, no change in the level of expression of the at least one gene is detected in the patient sample relative to the reference level.

Another embodiment of the invention provides methods of monitoring patient response to a treatment (e.g., anti-angiogenic therapy, e.g., anti-cancer therapy), the method including (a) determining that a sample obtained from the patient has a level of at least one gene set forth in Table 1 or 2 above or below the level of a reference level of the at least one gene and, optionally, (b) providing a recommendation that the treatment for the patient include an effective amount of a VEGF antagonist. In some embodiments, the methods can instead optionally include (b) providing a recommendation to the patient that treatment is not a VEGF antagonist if, for example, no change in the level of expression of the at least one gene is detected in the patient sample relative to the reference level.

Yet another embodiment of the invention features a method for treating an angiogenic disorder (e.g., cancer) in a patient, the method including (a) determining that a sample obtained from the patient has a level of at least one gene set forth in Table 1 or 2 above or below the level of a reference level of the at least one gene and (b) administering an effective amount of a VEGF antagonist. Referring to the embodiments set forth above, in some further embodiments, the patient is in a population of patients being tested for responsiveness to a VEGF antagonist and the reference level is the median level of expression of the at least one gene in the population of patients. In some embodiments, the change in level of expression of the at least one gene in the patient sample is an increase relative to the reference level. In some embodiments, the change in level of expression of the at least one gene in the patient sample is a decrease relative to the reference level. In some embodiments, the at least one gene in the biological sample obtained from the patient is detected by measuring mRNA. In some embodiments, expression of the at least one gene in the biological sample obtained from the patient is detected by measuring plasma protein levels. In some embodiments, the biological sample is tumor tissue. In some embodiments, the methods further comprise detecting expression of at least a second, third, fourth, or more gene set forth in Table 1 or 2 in the biological sample from the patient. In some embodiments, the at least one gene is selected from the group consisting of: Alk1, CD34, CD105, CD144, Col4a1, Col4a2, Dll4, EFNB2, EGFL7, ESM1, LAMA4, NG2, Nid2, Notch1, NRP1, NRP2, RGS5, Sema3f, TSP1, VEGFR1, VEGFR2, VEGFR3, and VIM. In some embodiments, the VEGF antagonist is an anti-VEGF antibody, such as bevacizumab. In some embodiments, the patient has an angiogenic disorder. In some embodiments, the patient has cancer selected from the group consisting of: colorectal cancer, breast cancer, lung cancer, glioblastoma, and combinations thereof.

Also referring to the embodiments set forth above, the methods can further optionally include selecting a therapy including a VEGF antagonist for treatment of the patient when a change in the level of expression of the at least one gene in the patient sample relative to the reference level is detected. Further, the methods can optionally include administering a VEGF antagonist (e.g., an anti-VEGF antibody, such as bevacizumab) to the patient.

Another embodiment of the invention provides methods for selecting a therapy for a particular patient in a population of patients being considered for therapy, the methods comprising: (a) detecting expression of at least one gene set forth in Table 1 or 2 in a biological sample obtained from the patient prior to any administration of a VEGF antagonist to the patient; (b) comparing the expression level of the at least one gene to a reference expression level of the at least one gene, wherein a change in the level of expression of the at least one gene in the patient sample relative to the reference level identifies a patient who is likely to respond to treatment with a VEGF antagonist, and (c) selecting a therapy including a VEGF antagonist if the patient is identified as likely to respond to treatment with a VEGF antagonist and, optionally, recommending to the patient the selected therapy including a VEGF antagonist; or (d) selecting a therapy that does not include a VEGF antagonist if the patient is not identified as likely to respond to treatment with a VEGF antagonist and, optionally, recommending to the patient the selected therapy that does not include a VEGF antagonist.

In some embodiments, the reference level is the median level of expression of the at least one gene in the population of patients. In some embodiments, the change in level of expression of the at least one gene in the patient sample is an increase relative to the reference level. In some embodiments, the change in level of expression of the at least one gene in the patient sample is a decrease relative to the reference level. In some embodiments, the methods further comprise detecting expression of at least a second, third, fourth, or more gene set forth in Table 1 or 2 in the biological sample from the patient. In some embodiments, the therapy of (d) is an agent selected from the group consisting of: an anti-neoplastic agent, a chemotherapeutic agent, a growth inhibitory agent, a cytotoxic agent, and combinations thereof. In some embodiments, the methods optionally further comprise (e) administering an effective amount of a VEGF antagonist to the patient if the patient is identified as likely to respond to treatment with a VEGF antagonist. In some embodiments, the VEGF antagonist is an anti-VEGF antibody, such as bevacizumab. In some embodiments, the methods further comprising administering an effective amount of at least a second agent. In some embodiments, the second agent is selected from the group consisting of: an anti-neoplastic agent, a chemotherapeutic agent, a growth inhibitory agent, a cytotoxic agent, and combinations thereof.

A further embodiment of the invention provides methods of identifying a biomarker for determining responsiveness to a VEGF antagonist, the methods comprising: (a) detecting the expression of a candidate biomarker in a biological sample obtained from a patient prior to administration of a VEGF antagonist to the patient; and (b) comparing the expression of the candidate biomarker to a reference expression level of the candidate biomarker, wherein a change in the level of expression of the candidate biomarker in the patient sample relative to the reference level identifies the candidate biomarker as a biomarker of a patient who will likely respond to treatment with a VEGF antagonist. In some embodiments, the reference level is the median level of expression of the at least one gene in a population of patients being tested for the likelihood they will respond to a VEGF antagonist. In some embodiments, the reference level is the expression level of the at least one gene in a sample previously obtained from the patient. In some embodiments, the patient was previously treated with a VEGF antagonist and is currently experiencing metastasis. In some embodiments, the VEGF antagonist is an anti-VEGF antibody, such as bevacizumab. Further, the methods can optionally further include (c) selecting a candidate biomarker having a change in level of expression relative to the reference for use as a biomarker for determining responsiveness to VEGF antagonist treatment.

In another embodiment, the invention provides methods for diagnosing an angiogenic disorder in a patient, the methods comprising the steps of: (a) detecting the expression level of at least one gene set forth in Table 1 or 2 or a biomarker identified according to methods such as those described above in a sample obtained from the patient prior to any administration of a VEGF antagonist to the patient; (b) comparing the expression level of the at least one gene or biomarker to a reference level of the at least one gene; wherein a change in the level of expression of the at least one gene in the patient sample relative to the reference level identifies a patient having an angiogenic disorder; and, optionally, (c) informing the patient that they have an angiogenic disorder. These methods can further include (d) selecting a VEGF antagonist for treatment of the patient when a change in the level of expression of the at least one gene in the patient sample relative to the reference level is detected. In addition, the methods can further include (e) administering a VEGF antagonist to the patient. In addition, the methods described herein can include a step of obtaining a sample from a patient, as described herein. Further, the methods described herein can be carried out on patients diagnosed with cancer, as described herein, to determine an optimal treatment regimen.

In any of the embodiments set forth above, the change in the level of expression of the at least one gene or biomarker in the patient sample relative to the reference level can be determined by calculating a VDV signature score ($VDV_i$) for the patient sample according to the algorithm:

$$VDV_i = \frac{1}{\sqrt{n}} \sum_{g=1}^{n} Z_{g,i}$$

in which $Z_{g=1,i}, Z_{g=2,i}, \ldots Z_{g=n,i}$ are standardized z-scores of expression values for each gene or biomarker g, from g=1 to g=n, of the sample i, and in which a $VDV_i$ below a first defined threshold indicates a decrease relative to the reference level, and a $VDV_i$ above a second defined threshold indicates an increase relative to the reference level. In some embodiments, the expression values for each gene or biomarker g, from g=1 to g=n, are qRT-PCR values for each gene g, from g=1 to g=n. In some embodiments, the first defined threshold is from −4 to −0.5 (e.g., −4, −3.5, −3, −2.5, −2, −1.5, −1, or −0.5) and the second defined threshold is from 0.5 to 4 (e.g., 0.5, 1, 1.5, 2, 2.5, 3, 3.5, or 4). In some embodiments, the first defined threshold is from −4 to −1 (e.g., −4, −3.5, −3, −2.5, −2, −1.5, or −1) and the second defined threshold is from 1 to 4 (e.g., 1, 1.5, 2, 2.5, 3, 3.5, or 4). In some embodiments, the first defined threshold is from −4 to −1.5 (e.g., −4, −3.5, −3, −2.5, −2, or −1.5) and the second defined threshold is from 1.5 to 4 (e.g., 1.5, 2, 2.5, 3, 3.5, or 4). In other embodiments, the first defined threshold is from −4 to −2 (e.g., −4, −3.5, −3, −2.5, or −2) and the second defined threshold is from 2 to 4 (e.g., 2, 2.5, 3, 3.5, or 4).

Further, in any of the embodiments set forth above and described elsewhere herein, the methods can also include a step of providing or selecting one or more agents for use in detecting the markers described herein (see, e.g., Tables 1 and 2). Thus, the methods can include selecting PCR primers, probes, and/or antibodies specific for one or more (e.g., 2, 3, 4, 5, 6, 7, 8, 9, 10, 11, 12, 13, 14, 15, 16, 17, 18, 19, 20, 21, 22, 23, or more) of the markers from Tables 1 or 2 (e.g., Alk1, CD34, CD105, CD144, Col4a1, Col4a2, Dll4, EFNB2, EGFL7, ESM1, LAMA4, NG2, Nid2, Notch1, NRP1, NRP2, RGS5, Sema3f, TSP1, VEGFR1, VEGFR2, VEGFR3, and/or VIM).

The invention also features kits for determining whether a patient may benefit from treatment with a VEGF antagonist, the kit including (a) compounds (e.g., polypeptides or polynucleotides (e.g., PCR primers or probes)) capable of determining the expression level of at least one gene set forth in Table 1 or 2 and, optionally, (b) instructions for use of the compounds (e.g., polypeptides or polynucleotides) to determine the expression level of the at least one gene set forth in Table 1 or 2, wherein a change in the level of expression of the at least one gene relative to a reference level indicates that the patient may benefit from treatment with a VEGF antagonist. In some embodiments, the polypeptides are antibodies. Further, in some embodiments, the primers and/or probes are bound to a solid surface, such as a microchip.

In all instances of the occurrence of the phrase "one or more," as noted above or elsewhere herein with respect to detection of the markers described herein (or agents for use in detecting the markers), this phrase specifically includes 2, 3, 4, 5, 6, 7, 8, 9, 10, 11, 12, 13, 14, 15, 16, 17, 18, 19, 20, 21, 22, 23, or more.

These and other embodiments are further described by the detailed description that follows.

BRIEF DESCRIPTION OF THE DRAWINGS

The application file contains at least one drawing executed in color. Copies of this patent or patent application with color drawings will be provided by the Office upon request and payment of the necessary fee.

FIG. 1C is a graph showing changes in VDV gene expression levels in response to treatment with a VEGF antagonist. Expression levels of genes (shown as red lines) decrease significantly relative to all genes (grey histogram). The dashed red line indicates the mean change for these selected genes. The black dashed line indicates the mean fold change for the rest of the genes.

FIG. 1D is a graph showing changes in gene expression levels in a subgroup of genes in response to treatment with a VEGF antagonist as assessed by qPCR. Bars represent mean expression from three independent biological replicates. Error bars=$\log_2$ standard deviation.

FIG. 2B is a set of graphs showing changes in VDV gene response to VEGF blockade in an orthotopic (intracranial) U87 glioblastoma model. Tumor samples were collected after 13-42 days of anti-VEGF or control treatment. Genes in the VDV signature (red lines) decrease significantly relative to all genes (shown as a grey histogram) in the stroma (upper graph, mouse chip, p<0.0105), but not in the tumor cells (lower graph, human chip, no significant differences). Individual proxVDV transcript fold-changes are annotated in black letters in the microarray density plot. n=5-10 instances for each treatment cohort.

FIG. 2C is a set of graphs showing a down-modulation is observed upon topical anti-VEGF application to a skin wound (upper graph, p=0.0125) and the converse up-regulation, when recombinant VEGF was applied for 12 hours (p<0.0001). Individual proxVDV transcript fold-changes are annotated in black letters.

FIG. 5A are graphs showing the consistent proxVDV downregulation by multiple VEGF pathway inhibitors. Analysis of gene expression in MDA-MB-231 xenograft tumors collected 8, 16, or 72 hours after treatment with VEGF and VEGFR-2 inhibitors (sunitinib and axitinib). Values represent the mean of the $\log_2$ fold change in relative gene expression induced by VEGF/VEGFR-2 inhibitor compared to control treatment. Gene expression data represent the $\log_2$ mean of 8 biological replicates for each treatment. Error bars represent standard deviation.

DETAILED DESCRIPTION OF THE PREFERRED EMBODIMENTS

I. Introduction

Figure 1A:
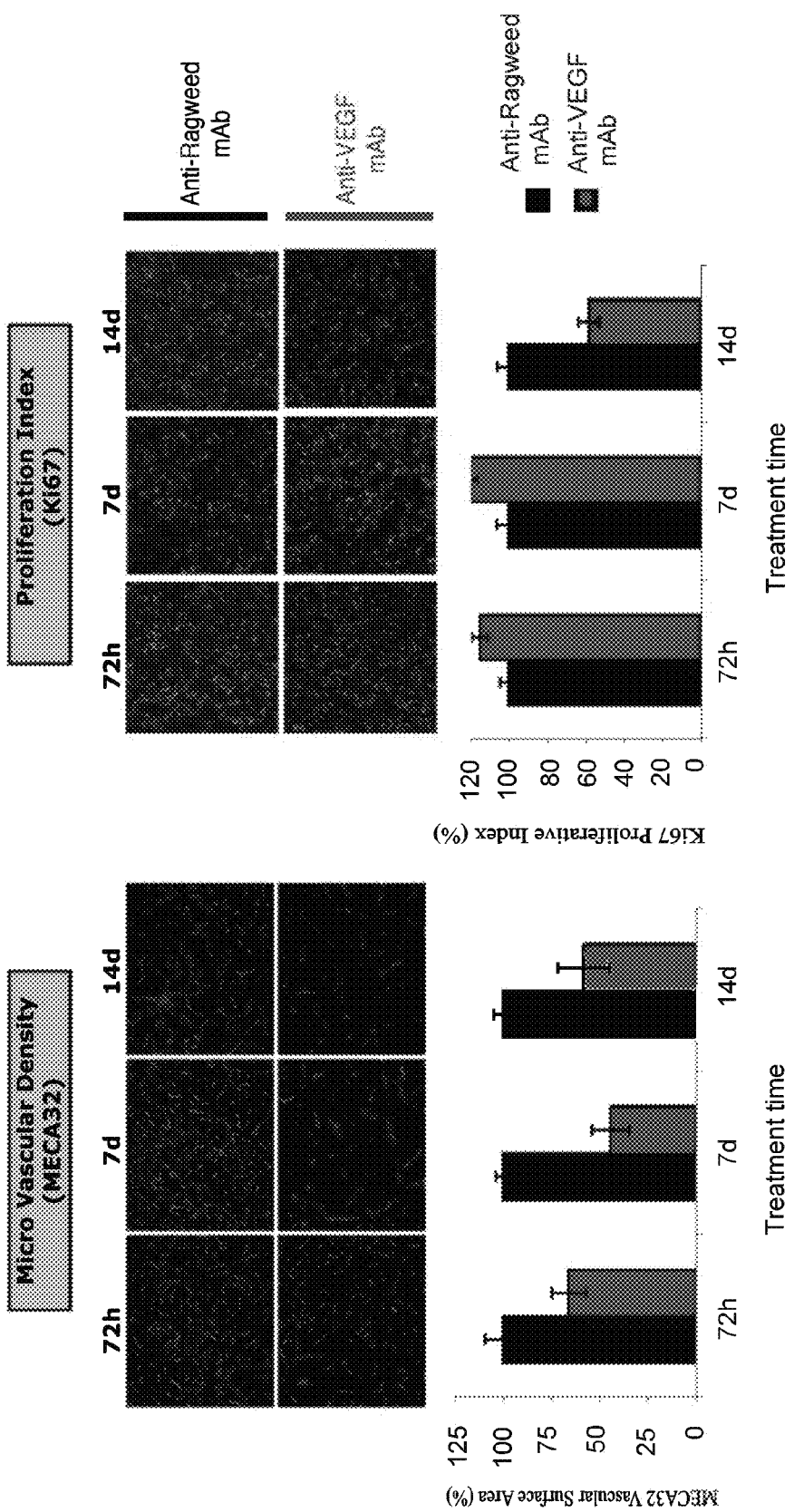
FIG. 1A shows histological and graphical analysis of micro-vascular density (MVD) and proliferation index determination of murine pancreatic neuro-endocrine tumor (PNET) cells at 72 hours, 7 days, and 14 days post-treatment with anti-VEGF mAb. Representative images from histological analysis of tumor vessel density via MECA-32 staining (left) and proliferative index via Ki67 (right) at various times following anti-VEGF treatment (20× magnification). Quantitation from 4-6 tumors in each case is shown in the bar graphs below as mean+/−SEM. *P<0.05, NS=not significant.

The present invention provides methods and compositions for monitoring and/or identifying patients sensitive or responsive to treatment with VEGF antagonists, e.g., an anti-VEGF antibody. The invention is based on the discovery that determination of expression levels of at least 1, 2, 3, 4, 5, 6, 7, 8, 9, 10, 11, 12, 13, 14, 15, 16, 17, 18, 19, 20, 21, 22, 23, or more gene(s) set forth in Table 1 or 2 before treatment with a VEGF antagonist (such as an anti-VEGF antibody) is useful for identifying patients sensitive to or responsive to treatment with a VEGF antagonist, e.g., an anti-VEGF antibody. Optionally, VEGF antagonist therapy can then be selected for the patients and, further, VEGF antagonist therapy can optionally be administered to the patients.

II. Definitions

The terms "biomarker" and "marker" are used interchangeably herein to refer to a DNA, RNA, protein, carbohydrate, or glycolipid-based molecular marker, the expression or presence of which in a subject's or patient's sample can be detected by standard methods (or methods disclosed herein) and is useful for monitoring the responsiveness or sensitivity of a mammalian subject to a VEGF antagonist. Such biomarkers include, but are not limited to, the genes set forth in Tables 1 and 2. Expression of such a biomarker may be determined to be higher or lower in a sample obtained from a patient sensitive or responsive to a VEGF antagonist than a reference level (including, e.g., the median expression level of the biomarker in a samples from a group/population of patients being tested for responsiveness to a VEGF antagonist; the level in a sample previously obtained from the individual at a prior time; or the level in a sample from a patient who received prior treatment with a VEGF antagonist (such as an anti-VEGF antibody) in a primary tumor setting, and who now may be experiencing metastasis). Individuals having an expression level that is greater than or less than the reference expression level of at least one gene, such as those set forth in Tables 1 and 2, can be identified as subjects/patients likely to respond to treatment with a VEGF antagonist. For example, such subjects/patients who exhibit gene expression levels at the most extreme 505, 45%, 40%, 35%, 30%, 25%, 20%, 15%, 10%, or 5% relative to (i.e., higher or lower than) the reference level (such as the median level, noted above), can be identified as subjects/patients likely to respond to treatment with a VEGF antagonist, such as an anti-VEGF antibody.

The terms "sample" and "biological sample" are used interchangeably to refer to any biological sample obtained from an individual including body fluids, body tissue (e.g., tumor tissue), cells, or other sources. Body fluids are, e.g., lymph, sera, whole fresh blood, peripheral blood mononuclear cells, frozen whole blood, plasma (including fresh or frozen), urine, saliva, semen, synovial fluid and spinal fluid. Samples also include breast tissue, renal tissue, colonic tissue, brain tissue, muscle tissue, synovial tissue, skin, hair follicle, bone marrow, and tumor tissue. Methods for obtaining tissue biopsies and body fluids from mammals are well known in the art.

An "effective response" of a patient or a patient's "responsiveness" or "sensitivity" to treatment with a VEGF antagonist refers to the clinical or therapeutic benefit imparted to a patient at risk for or suffering from an angiogenic disorder from or as a result of the treatment with the VEGF antagonist, such as an anti-VEGF antibody. Such benefit includes cellular or biological responses, a complete response, a partial response, a stable disease (without progression or relapse), or a response with a later relapse of the patient from or as a result of the treatment with the antagonist. For example, an effective response can be reduced tumor size or progression-free survival in a patient diagnosed as expressing one or more of the biomarkers set forth in Table 1 or 2 versus a patient not expressing one or more of the biomarkers. The expression of genetic biomarker(s) effectively predicts, or predicts with high sensitivity, such effective response.

"Antagonists" as used herein refer to compounds or agents which inhibit or reduce the biological activity of the molecule to which they bind. Antagonists include antibodies, synthetic or native-sequence peptides, immunoadhesins, and small-molecule antagonists that bind to VEGF, optionally conjugated with or fused to another molecule. A "blocking" antibody or an "antagonist" antibody is one which inhibits or reduces biological activity of the antigen it binds.

An "agonist antibody," as used herein, is an antibody which partially or fully mimics at least one of the functional activities of a polypeptide of interest.

The term "antibody" herein is used in the broadest sense and specifically covers monoclonal antibodies, polyclonal antibodies, multispecific antibodies (e.g., bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light-chain and heavy chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed. (W. B. Saunders, Co., 2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen-binding region thereof. Examples of antibody fragments include Fab, Fab', $F(ab')_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields a $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody-hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of an antibody, wherein these domains are present in a single polypeptide chain. Generally, the scFv polypeptide further comprises a polypeptide linker between the VH and VL domains that enables the scFv to form the desired structure for antigen binding. For a review of scFv, see, e.g., Pluckthün, in *The Pharmacology of Mono-clonal Antibodies*, vol. 113, Rosenburg and Moore eds. (Springer-Verlag, New York: 1994), pp 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *PNAS USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *PNAS USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *PNAS USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (e.g., U.S. Pat. No. 4,816,567 and Morrison et al., *PNAS USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all, or substantially all, of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *PNAS USA*, 103:3557-3562 (2006) regarding human antibodies generated via a human B-cell hybridoma technology.

The term "hypervariable region," "HVR," or "HV," when used herein refers to the regions of an antibody-variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. *Immunity* 13:37-45 (2000); Johnson and Wu in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are Kabat complementarity-determining regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat  | AbM    | Chothia | Contact |
|------|--------|--------|---------|---------|
| L1   | L24-L34 | L24-L34 | L26-L32 | L30-L36 |
| L2   | L50-L56 | L50-L56 | L50-L52 | L46-L55 |

-continued

| Loop | Kabat | AbM | Chothia | Contact |
|---|---|---|---|---|
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

The expression "variable-domain residue-numbering as in Kabat" or "amino acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

An "affinity-matured" antibody is one with one or more alterations in one or more HVRs thereof which result in an improvement in the affinity of the antibody for antigen, compared to a parent antibody which does not possess those alteration(s). In one embodiment, an affinity-matured antibody has nanomolar or even picomolar affinities for the target antigen. Affinity-matured antibodies are produced by procedures known in the art. For example, Marks et al., Bio/Technology 10:779-783 (1992) describes affinity maturation by VH- and VL-domain shuffling. Random mutagenesis of HVR and/or framework residues is described by, for example: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

"Growth-inhibitory" antibodies are those that prevent or reduce proliferation of a cell expressing an antigen to which the antibody binds.

Antibodies that "induce apoptosis" are those that induce programmed cell death, as determined by standard apoptosis assays, such as binding of annexin V, fragmentation of DNA, cell shrinkage, dilation of endoplasmic reticulum, cell fragmentation, and/or formation of membrane vesicles (called apoptotic bodies).

Antibody "effector functions" refer to those biological activities attributable to the Fc region (a native-sequence Fc region or amino acid-sequence-variant Fc region) of an antibody, and vary with the antibody isotype. Examples of antibody effector functions include: C1q binding and complement-dependent cytotoxicity (CDC); Fc-receptor binding; antibody-dependent cell-mediated cytotoxicity (ADCC); phagocytosis; down-regulation of cell-surface receptors (e.g., B-cell receptor); and B-cell activation.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

A "functional Fc region" possesses an "effector function" of a native-sequence Fc region. Exemplary "effector functions" include C1q binding; CDC; Fc-receptor binding; ADCC; phagocytosis; down-regulation of cell-surface receptors (e.g., B-cell receptor; BCR), etc. Such effector functions generally require the Fc region to be combined with a binding domain (e.g., an antibody-variable domain) and can be assessed using various assays as disclosed, for example, in definitions herein.

A "native-sequence Fc region" comprises an amino acid sequence identical to the amino acid sequence of an Fc region found in nature. Native-sequence human Fc regions include a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" comprises an amino acid sequence which differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

The term "Fc-region-comprising antibody" refers to an antibody that comprises an Fc region. The C-terminal lysine (residue 447 according to the EU numbering system) of the Fc region may be removed, for example, during purification of the antibody or by recombinant engineering the nucleic acid encoding the antibody. Accordingly, a composition comprising an antibody having an Fc region according to this invention can comprise an antibody with K447, with all K447 removed, or a mixture of antibodies with and without the K447 residue.

"Fc receptor" or "FcR" describes a receptor that binds to the Fc region of an antibody. In some embodiments, an FcR is a native-human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward, *Immunology Today,* 18 (12):592-8 (1997); Ghetie et al., *Nature Biotechnology,* 15 (7):637-40 (1997); Hinton et al., *J. Biol. Chem.,* 279(8):6213-6 (2004); WO 2004/92219 (Hinton et al.).

Binding to human FcRn in vivo and serum half-life of human FcRn high-affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See, also, for example, Shields et al. *J. Biol. Chem.* 9(2): 6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural-killer (NK) cells, monocytes, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g., NK cells, neutrophils, and macrophages) enables these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS (USA)* 95:652-656 (1998).

"Complement-dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551B1 and WO 1999/51642. See, also, e.g., Idusogie et al. *J. Immunol.* 164: 4178-4184 (2000).

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

In one embodiment, the "Kd" or "Kd value" according to this invention is measured by a radiolabeled antigen-binding assay (MA) performed with the Fab version of an antibody of interest and its antigen as described by the following assay. Solution-binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, microtiter plates (DYNEX Technologies, Inc.) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ surfactant in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, the Kd or Kd value is measured by using surface-plasmon resonance assays using a BIACORE®-2000 or a BIACORE®-3000 instrument (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 µg/ml (~0.2 µM) before injection at a flow rate of 5 µl/minute to achieve approximately ten response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN 20™ surfactant (PBST) at 25° C. at a flow rate of approximately 25 µl/min. Association rates ($k_{on}$) and dissociation rates ($k_{off}$) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}s^{-1}$ by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic) with a stirred cuvette.

An "on-rate," "rate of association," "association rate," or "$k_{on}$" according to this invention can also be determined as described above using a BIACORE®-2000 or a BIACORE®-3000 system (BIAcore, Inc., Piscataway, N.J.).

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

In certain embodiments, the humanized antibody useful herein further comprises amino acid alterations in the IgG Fc and exhibits increased binding affinity for human FcRn over an antibody having wild-type IgG Fc, by at least 60 fold, at least 70 fold, at least 80 fold, more preferably at least 100 fold, preferably at least 125 fold, even more preferably at least 150 fold to about 170 fold.

A "disorder" or "disease" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenic disorders.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is angiogenesis.

"Tumor", as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell proliferation. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The term "anti-neoplastic composition" or "anti-cancer composition" or "anti-cancer agent" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA VEGF, or VEGF receptor(s), TRAIL/Apo2, and other bioactive and organic chemical agents, etc. Combinations thereof are also included in the invention.

An "angiogenic factor or agent" is a growth factor which stimulates the development of blood vessels, e.g., promote angiogenesis, endothelial cell growth, stability of blood vessels, and/or vasculogenesis, etc. For example, angiogenic factors, include, but are not limited to, e.g., VEGF and members of the VEGF family, PlGF, PDGF family, fibroblast growth factor family (FGFs), TIE ligands (Angiopoietins), ephrins, Del-1, fibroblast growth factors: acidic (aFGF) and basic (bFGF), Follistatin, Granulocyte colony-stimulating factor (G-CSF), Hepatocyte growth factor (HGF)/scatter factor (SF), Interleukin-8 (IL-8), Leptin, Midkine, Placental growth factor, Platelet-derived endothelial cell growth factor (PD-ECGF), Platelet-derived growth factor, especially PDGF-BB or PDGFR-beta, Pleiotrophin (PTN), Progranulin, Proliferin, Transforming growth factor-alpha (TGF-alpha), Transforming growth factor-beta (TGF-beta), Tumor necrosis factor-alpha (TNF-alpha), Vascular endothelial growth factor (VEGF)/vascular permeability factor (VPF), etc. It would also include factors that accelerate wound healing, such as growth hormone, insulin-like growth factor-I (IGF-I), VIGF, epidermal growth factor (EGF), CTGF and members of its family, and TGF-alpha and TGF-beta. See, e.g., Klagsbrun and D'Amore, *Annu. Rev. Physiol.*, 53:217-39 (1991); Streit and Detmar, *Oncogene*, 22:3172-3179 (2003); Ferrara & Alitalo, *Nature Medicine* 5(12):1359-1364 (1999); Tonini et al., *Oncogene*, 22:6549-6556 (2003) (e.g., Table 1 listing known angiogenic factors); and, Sato *Int. J. Clin. Oncol.*, 8:200-206 (2003).

The term "VEGF" as used herein refers to the 165-amino acid human vascular endothelial cell growth factor and related 121-, 189-, and 206-amino acid human vascular endothelial cell growth factors, as described by Leung et al. *Science*, 246:1306 (1989), and Houck et al. *Mol. Endocrin.*, 5:1806 (1991), together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF. According to a preferred embodiment, the VEGF is a human VEGF.

A "VEGF antagonist" refers to a molecule capable of neutralizing, blocking, inhibiting, abrogating, reducing or interfering with VEGF activities including its binding to VEGF or one or more VEGF receptors or the nucleic acid encoding them. Preferably, the VEGF antagonist binds VEGF or a VEGF receptor. VEGF antagonists include anti-VEGF antibodies and antigen-binding fragments thereof, polypeptides that bind VEGF and VEGF receptors and block ligand-receptor interaction (e.g., immunoadhesins, peptibodies), anti-VEGF receptor antibodies and VEGF receptor antagonists such as small molecule inhibitors of the VEGFR tyrosine kinases, aptamers that bind VEGF and nucleic acids that hybridize under stringent conditions to nucleic acid sequences that encode VEGF or VEGF receptor (e.g., RNAi). According to one preferred embodiment, the VEGF antagonist binds to VEGF and inhibits VEGF-induced endothelial cell proliferation in vitro. According to one preferred embodiment, the VEGF antagonist binds to VEGF or a VEGF receptor with greater affinity than a non-VEGF or non-VEGF receptor. According to one preferred embodiment, the VEG antagonist binds to VEGF or a VEGF receptor with a Kd of between 1 uM and 1 pM. According to another preferred embodiment, the VEGF antagonist binds to VEGF or a VEGF receptor between 500 nM and 1 pM.

According to a preferred embodiment, the VEGF antagonist is selected from a polypeptide such as an antibody, a peptibody, an immunoadhesin, a small molecule or an aptamer. In a preferred embodiment, the antibody is an anti-VEGF antibody such as the AVASTIN® antibody or an anti-VEGF receptor antibody such as an anti-VEGFR2 or an anti-VEGFR3 antibody. Other examples of VEGF antagonists include: VEGF-Trap, Mucagen, PTK787, SU11248, AG-013736, Bay 439006 (sorafenib), ZD-6474, CP632, CP-547632, AZD-2171, CDP-171, SU-14813, CHIR-258, AEE-788, SB786034, BAY579352, CDP-791, EG-3306, GW-786034, RWJ-417975/CT6758 and KRN-633.

An "anti-VEGF antibody" is an antibody that binds to VEGF with sufficient affinity and specificity. Preferably, the anti-VEGF antibody of the invention can be used as a therapeutic agent in targeting and interfering with diseases or conditions wherein the VEGF activity is involved. An anti-VEGF antibody will usually not bind to other VEGF homologues such as VEGF-B or VEGF-C, nor other growth factors such as PlGF, PDGF or bFGF. A preferred anti-VEGF antibody is a monoclonal antibody that binds to the same epitope as the monoclonal anti-VEGF antibody A4.6.1 produced by hybridoma ATCC HB 10709. More preferably the anti-VEGF antibody is a recombinant humanized anti-VEGF monoclonal antibody generated according to Presta et al. (1997) Cancer Res. 57:4593-4599, including but not limited to the antibody known as bevacizumab (BV; Avastin®). According to another embodiment, anti-VEGF antibodies that can be used include, but are not limited to the antibodies disclosed in WO 2005/012359. According to one embodiment, the anti-VEGF antibody comprises the variable heavy and variable light region of any one of the antibodies disclosed in FIGS. 24, 25, 26, 27 and 29 of WO 2005/012359 (e.g., G6, G6-23, G6-31, G6-23.1, G6-23.2, B20, B20-4 and B20.4.1). In another preferred embodiment, the anti-VEGF antibody known as ranibizumab is the VEGF antagonist administered for ocular disease such as diabetic neuropathy and AMD.

The anti-VEGF antibody "Bevacizumab (By)", also known as "rhuMAb VEGF" or "Avastin®", is a recombinant humanized anti-VEGF monoclonal antibody generated according to Presta et al. (1997) *Cancer Res.* 57:4593-4599. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 daltons and is glycosylated. Other anti-VEGF antibodies include the antibodies described in U.S. Pat. No. 6,884,879 and WO 2005/044853.

The anti-VEGF antibody Ranibizumab or the LUCENTIS® antibody or rhuFab V2 is a humanized, affinity-matured anti-human VEGF Fab fragment. Ranibizumab is produced by standard recombinant technology methods in *Escherichia coli* expression vector and bacterial fermentation. Ranibizumab is not glycosylated and has a molecular mass of ~48,000 daltons. See WO98/45331 and US20030190317.

Dysregulation of angiogenesis can lead to abnormal angiogenesis, i.e., when excessive, insufficient, or otherwise inappropriate growth of new blood vessels (e.g., the location, timing or onset of the angiogenesis being undesired from a medical standpoint) in a diseased state or such that it causes a diseased state, i.e., an angiogenic disorder. Excessive, inappropriate or uncontrolled angiogenesis occurs when there is new blood vessel growth that contributes to the worsening of the diseased state or causes a diseased state. The new blood vessels can feed the diseased tissues, destroy normal tissues, and in the case of cancer, the new vessels can allow tumor cells to escape into the circulation and lodge in other organs (tumor metastases). Disease states involving abnormal angiogenesis (i.e., angiogenic disorders) include both non-neoplastic and neoplastic conditions including, e.g., cancer, especially vascularized solid tumors and metastatic tumors (including colon cancer, breast cancer, lung cancer (especially small-cell lung cancer), brain cancer (especially glioblastoma) or prostate cancer), undesired or aberrant hypertrophy, arthritis, rheumatoid arthritis (RA), inflammatory bowel disease or IBD (Crohn's disease and ulcerative colitis), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the anterior surface of the iris (rubeosis), ocular neovascular disease, vascular restenosis, arteriovenous malformations (AVM), meningioma, hemangioma, angiofibroma, thyroid hyperplasias (including Grave's disease), chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, myositis ossificans, hypertrophic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD, renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. The term "therapeutically effective amount" refers to an amount of an antibody, polypeptide or antagonist of this invention effective to "treat" a disease or disorder in a mammal (aka patient). In the case of cancer, the therapeutically effective amount of the drug can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug can prevent growth and/or kill existing cancer cells, it can be cytostatic and/or cytotoxic. In one embodiment, the therapeutically effective amount is a growth inhibitory amount. In another embodiment, the therapeutically effective amount is an amount that extends the survival of a patient. In another embodiment, the therapeutically effective amount is an amount that improves progression free survival of a patient.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount is less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$ $Sm^{153}$, $Bi^{212}$, $P^{32}$ and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin. Additional chemotherapeutic agents include the cytotoxic agents useful as antibody drug conjugates, such as maytansinoids (DM1, for example) and the auristatins MMAE and MMAF, for example.

"Chemotherapeutic agents" also include "anti-hormonal agents" that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth and/or proliferation of a cell (e.g., a cell expressing Robo4) either in vitro or in vivo. Thus, the growth inhibitory agent may be one which significantly reduces the percentage of Robo4-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as the anthracycline antibiotic doxorubicin ((8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione), epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

As used herein, the term "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human.

A "subject" herein is any single human subject, including a patient, eligible for treatment who is experiencing or has experienced one or more signs, symptoms, or other indicators of an angiogenic disorder. Intended to be included as a subject are any subjects involved in clinical research trials not showing any clinical sign of disease, or subjects involved in epidemiological studies, or subjects once used as controls. The subject may have been previously treated with a VEGF antagonist, or not so treated. The subject may be naïve to a second medicament being used when the treatment herein is started, i.e., the subject may not have been previously treated with, for example, an anti-neoplastic agent, a chemotherapeutic agent, a growth inhibitory agent, a cytotoxic agent at "baseline" (i.e., at a set point in time before the administration of a first dose of antagonist in the treatment method herein, such as the day of screening the subject before treatment is commenced). Such "naïve" subjects are generally considered to be candidates for treatment with such second medicament.

The expression "effective amount" refers to an amount of a medicament that is effective for treating angiogenesis disorders.

The term "pharmaceutical formulation" refers to a sterile preparation that is in such form as to permit the biological activity of the medicament to be effective, and which contains no additional components that are unacceptably toxic to a subject to which the formulation would be administered.

A "sterile" formulation is aseptic or free from all living microorganisms and their spores.

A "package insert" is used to refer to instructions customarily included in commercial packages of therapeutic products or medicaments, that contain information about the indications, usage, dosage, administration, contraindications, other therapeutic products to be combined with the packaged product, and/or warnings concerning the use of such therapeutic products or medicaments, etc.

A "kit" is any manufacture (e.g., a package or container) comprising at least one reagent, e.g., a medicament for treatment of an angiogenic disorder, or a probe for specifically detecting a biomarker gene or protein of the invention. The manufacture is preferably promoted, distributed, or sold as a unit for performing the methods of the present invention.

For purposes of non-response to medicament(s), a subject who experiences "a clinically unacceptably high level of toxicity" from previous or current treatment with one or more medicaments experiences one or more negative side-effects or adverse events associated therewith that are considered by an experienced clinician to be significant, such as, for example, serious infections, congestive heart failure, demyelination (leading to multiple sclerosis), significant hypersensitivity, neuropathological events, high degrees of autoimmunity, a cancer such as endometrial cancer, non-Hodgkin's lymphoma, breast cancer, prostate cancer, lung cancer, ovarian cancer, or melanoma, tuberculosis (TB), etc.

By "reducing the risk of a negative side effect" is meant reducing the risk of a side effect resulting from treatment with the antagonist herein to a lower extent than the risk observed resulting from treatment of the same patient or another patient with a previously administered medicament. Such side effects include those set forth above regarding toxicity, and are preferably infection, cancer, heart failure, or demyelination.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to various embodiments herein, one may use the results of an analytical assay to determine whether a specific therapeutic regimen using a VEGF antagonist, such as anti-VEGF antibody, should be performed.

The word "label" when used herein refers to a compound or composition that is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable. The term is intended to encompass direct labeling of a probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The terms "level of expression" or "expression level" are used interchangeably and generally refer to the amount of a polynucleotide or an amino acid product or protein in a biological sample. "Expression" generally refers to the process by which gene-encoded information is converted into the structures present and operating in the cell. Therefore, according to the invention "expression" of a gene may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis. "Expressed genes" include those that are transcribed into a polynucleotide as mRNA and then translated into a protein, and also those that are transcribed into RNA but not translated into a protein (for example, transfer and ribosomal RNAs).

As used herein, the term "covariate" refers to certain variables or information relating to a patient. The clinical endpoints are frequently considered in regression models, where the endpoints represent the dependent variable and the biomarkers represent the main or target independent variables (regressors). If additional variables from the clinical data pool are considered, they are denoted as (clinical) covariates.

The term "clinical covariate" is used herein to describe all clinical information about the patient, which is in general available at baseline. These clinical covariates comprise demographic information like sex, age, etc., other anamnestic information, concomitant diseases, concomitant therapies, results of physical examinations, common laboratory parameters obtained, known properties of the angiogenic disorders, clinical disease staging, timing and result of pretreatments, disease history, as well as all similar information that may be associated with the clinical response to treatment.

As used herein, the term "raw analysis" or "unadjusted analysis" refers to regression analyses, wherein besides the considered biomarkers, no additional clinical covariates are used in the regression model, neither as independent factors nor as stratifying covariate.

As used herein, the term "adjusted by covariates" refers to regression analyses, wherein besides the considered biomarkers, additional clinical covariates are used in the regression model, either as independent factors or as stratifying covariate.

As used herein, the term "univariate" refers to regression models or graphical approaches wherein, as an independent variable, only one of the target biomarkers is part of the model. These univariate models can be considered with and without additional clinical covariates.

As used herein, the term "multivariate" refers to regression models or graphical approaches wherein, as independent variables, more than one of the target biomarkers is part of the model. These multivariate models can be considered with and without additional clinical covariates.

III. Methods to Identify Patients Responsive to VEGF Antagonists

The present invention provides methods for identifying and/or monitoring patients likely to be responsive to VEGF antagonist (e.g., anti-VEGF antibody) therapy. The methods are useful, inter alia, for increasing the likelihood that administration of a VEGF antagonist (e.g., an anti-VEGF antibody) to a patient will be efficacious. The methods comprise detecting expression of one or more genetic biomarkers in a biological sample from a patient, wherein the expression of one or more such biomarkers is indicative of whether the patient will be sensitive or responsive to VEGF antagonists, such as anti-VEGF antibodies. More particularly, the expression of at least 1, 2, 3, 4, 5, 6, 7, 8, 9, 10, 11, 12, 13, 14, 15, 16, 17, 18, 19, 20, 21, 22, or 23 genes set forth in Table 1 or 2 in a sample from a patient is useful for monitoring whether the patient will be responsive or sensitive to a VEGF antagonist, such as an anti-VEGF antibody.

In some embodiments, expression of at least one gene selected from the following group: Alk1, CD34, CD105, CD144, Col4a1, Col4a2, Dll4, EFNB2, EGFL7, ESM1, LAMA4, NG2, Nid2, Notch1, NRP1, NRP2, RGS5, Sema3f, TSP1, VEGFR1, VEGFR2, VEGFR3, and VIM, is useful for monitoring whether the patient will be responsive or sensitive to a VEGF antagonist, such as an anti-VEGF antibody. The methods further can, optionally, include selection of a VEGF antagonist (e.g., an anti-VEGF antibody, such as bevacizumab) for administration to the patient and further include, optionally, administration of a VEGF antagonist (e.g., an anti-VEGF antibody, such as bevacizumab) to the patient.

The disclosed methods and assays provide for convenient, efficient, and potentially cost-effective means to obtain data and information useful in assessing appropriate or effective therapies for treating patients. For example, a patient could provide a tissue sample (e.g., a tumor biopsy or a blood sample) before treatment with a VEGF antagonist and the sample could be examined by way of various in vitro assays to determine whether the patient's cells would be sensitive to a VEGF antagonist, such as an anti-VEGF antibody.

The invention provides methods for monitoring the sensitivity or responsiveness of a patient to a VEGF antagonist, such as an anti-VEGF antibody. The methods may be conducted in a variety of assay formats, including assays detecting genetic or protein expression (such as PCR and enzyme immunoassays) and biochemical assays detecting appropriate activity. Determination of expression or the presence of such biomarkers in the samples is predictive that the patient providing the sample will be sensitive to the biological effects of a VEGF antagonist, such as an anti-VEGF antibody. Applicants' invention herein is that a change (i.e., an increase or decrease) in the expression at least 1, 2, 3, 4, 5, 6, 7, 8, 9, 10, 11, 12, 13, 14, 15, 16, 17, 18, 19, 20, 21, 22, 23, or more gene(s) set forth in Table 1 or 2 in a sample from a patient correlates with the observed treatment efficacy of such a patient to a VEGF antagonist, such as an anti-VEGF antibody. Example 1 shows that increased levels of the genes in Table 2 correlate with such treatment efficacy, and thus in various embodiments detection of such levels in the methods described herein are included in the invention. In other embodiments, the invention includes a test panel for analysis of expression of the genes of Table 1 or Table 2, e.g., a test panel including probes specific for these genes or a subset thereof (e.g., at least 1, 2, 3, 4, 5, 6, 7, 8, 9, 10, 11, 12, 13, 14, 15, 16, 17, 18, 19, 20, 21, 22, 23, or more gene(s) set forth in Table 1 or 2). Such a test panel may comprise, for example, probes on a microchip array for use in this analysis.

According to the methods of the invention, the likelihood that a particular individual (e.g., a patient) is likely to respond to treatment with a VEGF antagonist can be determined by detecting the expression level of at least one gene set forth in Table 1 or 2 and comparing the expression level of the gene to a reference expression level. For example, the reference expression level may be the median expression level of the at least one gene in a group/population of patients being tested for responsiveness to a VEGF antagonist. In some embodiments, the reference expression level is the expression level of the at least one gene in a sample previously obtained from the individual at a prior time. In other embodiments, the individuals are patients who received prior treatment with a VEGF antagonist in a primary tumor setting. In some embodiments, the individuals are patients who are experiencing metastasis. Individuals who have an expression level that is greater than or less than the reference expression level of at least one gene set forth in Table 1 or 2 are identified as subjects/patients likely to respond to treatment with a VEGF antagonist. Subjects/patients who exhibit gene expression levels at the most extreme 50%, 45%, 40%, 35%, 30%, 25%, 20%, 15%, 10%, or 5% relative to (i.e., higher or lower than) the median are identified as patients likely to respond to treatment with a VEGF antagonist. The subjects/patients may be informed that they have an increased likelihood of being responsive to treatment with a VEGF antagonist and/or provided a recommendation that treatment include a VEGF antagonist. The gene expression level can be determined using at least one of the genes set forth in Table 1 or 2 or any linear combination of genes set forth in Table 1 or 2 (e.g., mean, weighted mean, or median) using methods known in the art and described in, e.g., Sokal R. R. and Rholf, F. J. (1995) "Biometry: the principles and practice of statistics in biological research," W.H. Freeman and Co. New York, N.Y. As noted above, the methods further can, optionally, include selection of a VEGF antagonist (e.g., an anti-VEGF antibody, such as bevacizumab) for administration to the patient and further include, optionally, administration of a VEGF antagonist (e.g., an anti-VEGF antibody, such as bevacizumab) to the patient.

In any of the methods described above, a VDV signature score ($VDV_i$) can be calculated that provides quantitative information regarding the extent to which the expression of a particular set of genes is collectively overexpressed or underexpressed relative to a centered mean. For example, a $VDV_i$ can be calculated for each sample i for which all of the VDV genes (see, e.g., Table 1 or 2) were analyzed, which represents a weighted average of z-scores across the analyzed VDV genes and is given by the algorithm:

$$VDV_i = \frac{1}{\sqrt{n}} \sum_{g=1}^{n} Z_{g,i}$$

in which $Z_{g=1,i}, Z_{g=2,i}, \ldots Z_{g=n,i}$ are standardized z-scores of expression values for each gene or biomarker g, from g=1 to g=n, of the sample i, and for which a $VDV_i$ below a first defined threshold indicates a decrease relative to the reference level (e.g., collective underexpression), and a $VDV_i$ above a second defined threshold indicates an increase relative to the reference level (e.g., collective overexpression). The expression values for each gene or biomarker g, from g=1 to g=n, may be, for example, qRT-PCR values for each gene g or biomarker, from g=1 to g=n. The first defined threshold may be from −4 to −0.5 (e.g., −4, −3.5, −3, −2.5, −2, −1.5, −1, or −0.5) and the second defined threshold may be from 0.5 to 4 (e.g., 0.5, 1, 1.5, 2, 2.5, 3, 3.5, or 4). In some instances, the first defined threshold may be from −4 to −1 (e.g., −4, −3.5, −3, −2.5, −2, −1.5, or −1) and the second defined threshold may be from 1 to 4 (e.g., 1, 1.5, 2, 2.5, 3, 3.5, or 4). In other instances, the first defined threshold may be from −4 to −1.5 (e.g., −4, −3.5, −3, −2.5, −2, or −1.5) and the second defined threshold may be from 1.5 to 4 (e.g., 1.5, 2, 2.5, 3, 3.5, or 4). Alternatively, the first defined threshold may be from −4 to −2 (e.g., −4, −3.5, −3, −2.5, or −2) and the second defined threshold may be from 2 to 4 (e.g., 2, 2.5, 3, 3.5, or 4).

In one aspect, this invention provides a method of monitoring whether a patient with an angiogenic disorder will respond to treatment with a VEGF antagonist, such as an anti-VEGF antibody, comprising assessing, as a biomarker, expression of at least one gene set forth in Table 1 or 2 (e.g., at least one of Alk1, CD34, CD105, CD144, Col4a1, Col4a2, Dll4, EFNB2, EGFL7, ESM1, LAMA4, NG2, Nid2, Notch1, NRP1, NRP2, RGS5, Sema3f, TSP1, VEGFR1, VEGFR2, VEGFR3, and VIM) in a sample from the patient; obtained before any VEGF antagonist has been administered to the patient. A change (i.e., increase or decrease) in the expression of the at least one gene set forth in Table 1 or 2 relative to a reference level (see above) indicates that the patient will respond to treatment with a VEGF antagonist, such as an anti-VEGF antibody. The subjects/patients may be informed that they have an increased likelihood of being responsive to treatment with a VEGF antagonist and/or provided a recommendation that treatment include a VEGF antagonist.

In another embodiment, the present invention provides a method of monitoring the sensitivity or responsiveness of a patient to a VEGF antagonist, such as an anti-VEGF antibody. This method comprises assessing gene expression of at least 1, 2, 3, 4, 5, 6, 7, 8, 9, 10, 11, 12, 13, 14, 15, 16, 17, 18, 19, 20, 21, 22, 23, or more gene(s) set forth in Table 1 or 2 from a patient sample and predicting the sensitivity or responsiveness of the patient to the VEGF antagonist, such as an anti-VEGF antibody, wherein a change (i.e., increase or decrease) in the expression of at least 1, 2, 3, 4, 5, 6, 7, 8, 9, 10, 11, 12, 13, 14, 15, 16, 17, 18, 19, 20, 21, 22, 23, or more gene(s) set forth in Table 1 or 2 correlates with sensitivity or responsiveness of the patient to effective treatment with the VEGF antagonist. According to this method, a biological sample is obtained from the patient before administration of any VEGF antagonist and subjected to an assay to evaluate whether the expression products of at least 1, 2, 3, 4, 5, 6, 7, 8, 9, 10, 11, 12, 13, 14, 15, 16, 17, 18, 19, 20, 21, 22, 23, or more gene(s) set forth in Table 1 or 2 are present in the sample. If expression of 1, 2, 3, 4, 5, 6, 7, 8, 9, 10, 11, 12, 13, 14, 15, 16, 17, 18, 19, 20, 21, 22, 23, or more gene(s) set forth in Table 1 or 2 is changed (i.e., increased or decreased) relative to a reference level (e.g., see above), the patient is determined to be sensitive or responsive to treatment with a VEGF antagonist, such as an anti-VEGF antibody. The patient may be informed that they have an increased likelihood of being sensitive or responsive to treatment with a VEGF antagonist and/or provided a recommendation that anti-cancer therapy include a VEGF antagonist. As noted above, the methods further can, optionally, include selection of a VEGF antagonist (e.g., an anti-VEGF antibody, such as bevacizumab) for administration to the patient and further include, optionally, administration of a VEGF antagonist (e.g., an anti-VEGF antibody, such as bevacizumab) to the patient.

Further, any of the methods described herein can also include a step of providing or selecting one or more agents for use in detecting the markers described herein (see, e.g., Tables 1 and 2). Thus, the methods can include selecting PCR primers, probes, and/or antibodies specific for one or more (e.g., 2, 3, 4, 5, 6, 7, 8, 9, 10, 11, 12, 13, 14, 15, 16, 17, 18, 19, 20, 21, 22, 23, or more) of the markers from Tables 1 or 2 (e.g., Alk1, CD34, CD105, CD144, Col4a1, Col4a2, Dll4, EFNB2, EGFL7, ESM1, LAMA4, NG2, Nid2, Notch1, NRP1, NRP2, RGS5, Sema3f, TSP1, VEGFR1, VEGFR2, VEGFR3, and/or VIM).

One of skill in the medical arts, particularly pertaining to the application of diagnostic tests and treatment with therapeutics, will recognize that biological systems are somewhat variable and not always entirely predictable, and thus many good diagnostic tests or therapeutics are occasionally ineffective. Thus, it is ultimately up to the judgment of the attending physician to determine the most appropriate course of treatment for an individual patient, based upon test results, patient condition and history, and his or her own experience. There may even be occasions, for example, when a physician will choose to treat a patient with a VEGF antagonist, such as an anti-VEGF antibody, even when a patient is not predicted to be particularly sensitive to VEGF antagonists, based on data from diagnostic tests or from other criteria, particularly if all or most of the other obvious treatment options have failed, or if some synergy is anticipated when given with another treatment.

In further expressed embodiments, the present invention provides a method of predicting the sensitivity of a patient to treatment with a VEGF antagonist, such as an anti-VEGF antibody, or predicting whether a patient will respond effectively to treatment with a VEGF antagonist, comprising assessing the level of one or more of the genetic biomarkers identified herein expressed in the sample; and predicting the sensitivity of the patient to inhibition by a VEGF antagonist, wherein expression levels of one or more of these genetic biomarkers correlates with high sensitivity of the patient to effective response to treatment with a VEGF antagonist.

The present invention further provides a method of identifying a biomarker whose expression level is predictive of the sensitivity or responsiveness of a particular patient to a VEGF antagonist, such as an anti-VEGF antibody, comprising: (a) measuring the expression level of a candidate biomarker in a panel of cells that displays a range of sensitivities to a VEGF antagonist, and (b) identifying a correlation between the expression level of, seropositivity for, or presence of said candidate biomarker in the cells and the sensitivity or responsiveness of the patient to the VEGF antagonist, wherein the correlation indicates that the expression level, seropositivity, or presence of said biomarker is predictive of the responsiveness of the patient to treatment by a VEGF antagonist. In one embodiment of this method the panel of cells is a panel of samples prepared from samples derived from patients or experimental animal models. In an additional embodiment the panel of cells is a panel of cell lines in mouse xenografts, wherein responsiveness can, for example, be determined by monitoring a molecular marker of responsiveness, e.g., at least one of Alk1, CD34, CD105, CD144, Col4a1, Col4a2, Dll4, EFNB2, EGFL7, ESM1, LAMA4, NG2, Nid2, Notch1, NRP1, NRP2, RGS5, Sema3f, TSP1, VEGFR1, VEGFR2, VEGFR3, and VIM.

The present invention also provides a method of identifying a biomarker that is useful for monitoring sensitivity or responsiveness to a VEGF antagonist, such as an anti-VEGF antibody, the method comprising: (a) measuring the level of a candidate biomarker in samples from patients with angiogenic disorders obtained before any dose of a VEGF antagonist is administered to the patients, wherein an change (i.e., an increase or decrease) in the expression of the candidate biomarker relative to a control indicates that the biomarker is diagnostic for more effective treatment of the angiogenic disorder with a VEGF antagonist. In some embodiments, the biomarker is genetic and its expression is analyzed.

The sample may be taken from a patient who is suspected of having, or is diagnosed as having an angiogenic disorder, and hence is likely in need of treatment, or from a normal individual who is not suspected of having any disorder. For assessment of marker expression, patient samples, such as those containing cells, or proteins or nucleic acids produced by these cells, may be used in the methods of the present invention. In the methods of this invention, the level of a biomarker can be determined by assessing the amount (e.g., the absolute amount or concentration) of the markers in a sample, preferably a tissue sample (e.g., a tumor tissue sample, such as a biopsy). In addition, the level of a biomarker can be assessed in bodily fluids or excretions containing detectable levels of biomarkers. Bodily fluids or secretions useful as samples in the present invention include, e.g., blood, urine, saliva, stool, pleural fluid, lymphatic fluid, sputum, ascites, prostatic fluid, cerebrospinal fluid (CSF), or any other bodily secretion or derivative thereof. The word blood is meant to include whole blood, plasma, serum, or any derivative of blood. Assessment of a biomarker in such bodily fluids or excretions can sometimes be preferred in circumstances where an invasive sampling method is inappropriate or inconvenient. However, in the case of samples that are bodily fluids, the sample to be tested herein is preferably blood, synovial tissue, or synovial fluid, most preferably blood.

The sample may be frozen, fresh, fixed (e.g., formalin fixed), centrifuged, and/or embedded (e.g., paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, biopsies may also be subjected to post-collection preparative and storage techniques, e.g., fixation.

In any of the methods described herein, the individual (e.g., patient/subject) may be informed of an increased or decreased likelihood of being sensitive or responsive to treatment with a VEGF antagonist; provided a recommendation of a treatment or therapy (e.g., an anti-cancer therapy that includes or does not include a VEGF antagonist); and/or selected a suitable therapy (e.g., a VEGF antagonist and/or other anti-angiogenic agent).

As noted above, all of the methods further can, optionally, include selection of a VEGF antagonist (e.g., an anti-VEGF antibody, such as bevacizumab) for administration to the patient and further include, optionally, administration of a VEGF antagonist (e.g., an anti-VEGF antibody, such as bevacizumab) to the patient.

A. Detection of Gene Expression

The genetic biomarkers described herein can be detected using any method known in the art. For example, tissue or cell samples from mammals can be conveniently assayed for, e.g., mRNAs or DNAs from a genetic biomarker of interest using Northern, dot-blot, or polymerase chain reaction (PCR) analysis, array hybridization, RNase protection assay, or using DNA SNP chip microarrays, which are commercially available, including DNA microarray snapshots. For example, real-time PCR (RT-PCR) assays such as quantitative PCR assays are well known in the art. In an illustrative embodiment of the invention, a method for detecting mRNA from a genetic biomarker of interest in a biological sample comprises producing cDNA from the sample by reverse transcription using at least one primer; amplifying the cDNA so produced; and detecting the presence of the amplified cDNA. In addition, such methods can include one or more steps that allow one to determine the levels of mRNA in a biological sample (e.g., by simultaneously examining the levels a comparative control mRNA sequence of a "housekeeping" gene such as an actin family member). Optionally, the sequence of the amplified cDNA can be determined.

1. Detection of Nucleic Acids

In one specific embodiment, expression of the genes set forth in Table 1 or 2 can be performed by RT-PCR technology. Probes used for PCR may be labeled with a detectable marker, such as, for example, a radioisotope, fluorescent compound, bioluminescent compound, a chemiluminescent compound, metal chelator, or enzyme. Such probes and primers can be used to detect the presence of expressed genes set forth in Table 1 or 2 in a sample. As will be understood by the skilled artisan, a great many different primers and probes may be prepared based on the sequences provided in herein and used effectively to amplify, clone and/or determine the presence and/or levels of expressed genes set forth in Table 1 or 2.

Other methods include protocols that examine or detect mRNAs from at least one of the genes set forth in Table 1 or 2 (e.g., Alk1, CD34, CD105, CD144, Col4a1, Col4a2, Dll4, EFNB2, EGFL7, ESM1, LAMA4, NG2, Nid2, Notch1, NRP1, NRP2, RGS5, Sema3f, TSP1, VEGFR1, VEGFR2, VEGFR3, and VIM mRNAs), in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment (see, e.g., WO 2001/75166). See, for example, U.S. Pat. Nos. 5,700,637, 5,445,934, and 5,807,522, Lockart, *Nature Biotechnology*, 14:1675-1680 (1996); and Cheung et al., *Nature Genetics* 21(Suppl):15-19 (1999) for a discussion of array fabrication.

In addition, the DNA profiling and detection method utilizing microarrays described in EP 1753878 may be employed. This method rapidly identifies and distinguishes between different DNA sequences utilizing short tandem repeat (STR) analysis and DNA microarrays. In an embodiment, a labeled STR target sequence is hybridized to a DNA microarray carrying complementary probes. These probes vary in length to cover the range of possible STRs. The labeled single-stranded regions of the DNA hybrids are selectively removed from the microarray surface utilizing a post-hybridization enzymatic digestion. The number of repeats in the unknown target is deduced based on the pattern of target DNA that remains hybridized to the microarray.

One example of a microarray processor is the Affymetrix GENECHIP® system, which is commercially available and comprises arrays fabricated by direct synthesis of oligonucleotides on a glass surface. Other systems may be used as known to one skilled in the art.

Other methods for determining the level of the biomarker besides RT-PCR or another PCR-based method include proteomics techniques, as well as individualized genetic profiles that are necessary to treat angiogenic disorders based on patient response at a molecular level. The specialized microarrays herein, e.g., oligonucleotide microarrays or cDNA microarrays, may comprise one or more biomarkers having expression profiles that correlate with either sensitivity or resistance to one or more anti-VEGF antibodies. Other methods that can be used to detect nucleic acids, for use in the invention, involve high throughput RNA sequence expression analysis, including RNA-based genomic analysis, such as, for example, RNASeq.

Many references are available to provide guidance in applying the above techniques (Kohler et al., *Hybridoma Techniques* (Cold Spring Harbor Laboratory, New York, 1980); Tijssen, *Practice and Theory of Enzyme Immunoassays* (Elsevier, Amsterdam, 1985); Campbell, *Monoclonal Antibody Technology* (Elsevier, Amsterdam, 1984); Hurrell, *Monoclonal Hybridoma Antibodies: Techniques and Applications* (CRC Press, Boca Raton, Fla., 1982); and Zola, *Monoclonal Antibodies: A Manual of Techniques*, pp. 147-158 (CRC Press, Inc., 1987)). Northern blot analysis is a conventional technique well known in the art and is described, for example, in *Molecular Cloning, a Laboratory Manual*, second edition, 1989, Sambrook, Fritch, Maniatis, Cold Spring Harbor Press, 10 Skyline Drive, Plainview, N.Y. 11803-2500. Typical protocols for evaluating the status of genes and gene products are found, for example in Ausubel et al. eds., 1995, *Current Protocols In Molecular Biology*, Units 2 (Northern Blotting), 4 (Southern Blotting), 15 (Immunoblotting) and 18 (PCR Analysis).

2. Detection of Proteins

As to detection of protein biomarkers such as at least one of Alk1, CD34, CD105, CD144, Col4a1, Col4a2, Dll4, EFNB2, EGFL7, ESM1, LAMA4, NG2, Nid2, Notch1, NRP1, NRP2, RGS5, Sema3f, TSP1, VEGFR1, VEGFR2, VEGFR3, and VIM, for example, various protein assays are available including, for example, antibody-based methods as well as mass spectroscopy and other similar means known in the art. In the case of antibody-based methods, for example, the sample may be contacted with an antibody specific for said biomarker under conditions sufficient for an antibody-biomarker complex to form, and then detecting said complex. Detection of the presence of the protein biomarker may be accomplished in a number of ways, such as by Western blotting (with or without immunoprecipitation), 2-dimensional SDS-PAGE, immunoprecipitation, fluorescence activated cell sorting (FACS), flow cytometry, and ELISA procedures for assaying a wide variety of tissues and samples, including plasma or serum. A wide range of immunoassay techniques using such an assay format are available, see, e.g., U.S. Pat. Nos. 4,016,043, 4,424,279, and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride, or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g., 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

An alternative method involves immobilizing the target biomarkers in the sample and then exposing the immobilized target to specific antibody which may or may not be labeled with a reporter molecule. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e., radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase, and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

B. Kits

For use in detection of the biomarkers, kits or articles of manufacture are also provided by the invention. Such kits can be used to determine if a subject with an angiogenic disorder will be effectively responsive to a VEGF antagonist. These kits may comprise a carrier means being compartmentalized to receive in close confinement one or more container means such as vials, tubes, and the like, each of the container means comprising one of the separate compounds or elements to be used in the method. For example, one of the container means may comprise a probe that is or can be detectably labeled. Such probe may be a polypeptide (e.g., an antibody) or polynucleotide specific for a protein or message, respectively. Where the kit utilizes nucleic acid hybridization to detect the target nucleic acid, the kit may also have containers containing nucleotide(s) for amplification of the target nucleic acid sequence (e.g., PCR primers) and/or a container comprising a reporter-means, such as a biotin-binding protein, e.g., avidin or streptavidin, bound to a reporter molecule, such as an enzymatic, florescent, or radioisotope label.

Such kit will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific application, and may also indicate directions for either in vivo or in vitro use, such as those described above.

The kits of the invention have a number of embodiments. A typical embodiment is a kit comprising a container, a label on said container, and a composition contained within said container, wherein the composition includes a primary antibody that binds to a protein or autoantibody biomarker, and the label on said container indicates that the composition can be used to evaluate the presence of such proteins or antibodies in a sample, and wherein the kit includes instructions for using the antibody for evaluating the presence of biomarker proteins in a particular sample type. The kit can further comprise a set of instructions and materials for preparing a sample and applying antibody to the sample. The kit may include both a primary and secondary antibody, wherein the secondary antibody is conjugated to a label, e.g., an enzymatic label.

Another embodiment is a kit comprising a container, a label on said container, and a composition contained within said container, wherein the composition includes one or more polynucleotides that hybridize to a complement of a biomarker set forth in Table 1 or 2 under stringent conditions, and the label on said container indicates that the composition can be used to evaluate the presence of a biomarker set forth in Table 1 or 2 in a sample, and wherein the kit includes instructions for using the polynucleotide(s) for evaluating the presence of the biomarker RNA or DNA in a particular sample type.

Other optional components of the kit include one or more buffers (e.g., block buffer, wash buffer, substrate buffer, etc.), other reagents such as substrate (e.g., chromogen) that is chemically altered by an enzymatic label, epitope retrieval solution, control samples (positive and/or negative controls), control slide(s), etc. Kits can also include instructions for interpreting the results obtained using the kit.

In further specific embodiments, for antibody-based kits, the kit can comprise, for example: (1) a first antibody (e.g., attached to a solid support) that binds to a biomarker protein; and, optionally, (2) a second, different antibody that binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a biomarker protein or (2) a pair of primers useful for amplifying a biomarker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples that can be assayed and compared to the test sample. Each component of the kit can be enclosed within an individual container and all of the various containers can be within a single package, along with instructions for interpreting the results of the assays performed using the kit.

In one example, a kit of the invention includes agents (e.g., probes, primers, and/or antibodies) specific for one or more of the markers set forth in Table 1 or Table 2. Thus, the kit can include such agents with respect to 1, 2, 3, 4, 5, 6, 7, 8, 9, 10, 11, 12, 13, 14, 15, 16, 17, 18, 19, 20, 21, 22, 23, or more of such markers (e.g., Alk1, CD34, CD105, CD144, Col4a1, Col4a2, Dll4, EFNB2, EGFL7, ESM1, LAMA4, NG2, Nid2, Notch1, NRP1, NRP2, RGS5, Sema3f, TSP1, VEGFR1, VEGFR2, VEGFR3, and/or VIM). The agents can be present in separate containers within the kit or present as a mixture. Optionally, the agents can be immobilized on a microchip, and also optionally, controls may be included.

C. Statistics

As used herein, the general form of a prediction rule consists in the specification of a function of one or multiple biomarkers potentially including clinical covariates to predict response or non-response, or more generally, predict benefit or lack of benefit in terms of suitably defined clinical endpoints.

The simplest form of a prediction rule consists of a univariate model without covariates, wherein the prediction is determined by means of a cutoff or threshold. This can be phrased in terms of the Heaviside function for a specific cutoff c and a biomarker measurement x, where the binary prediction A or B is to be made, then if H (x−c)=0, then predict A. If H (x−c)=1, then predict B.

This is the simplest way of using univariate biomarker measurements in prediction rules. If such a simple rule is sufficient, it allows for a simple identification of the direction of the effect, i.e., whether high or low expression levels are beneficial for the patient.

The situation can be more complicated if clinical covariates need to be considered and/or if multiple biomarkers are used in multivariate prediction rules. The two hypothetical examples below illustrate the issues involved:

Covariate Adjustment (Hypothetical Example)

For a biomarker X it is found in a clinical trial population that high expression levels are associated with a worse clinical response (univariate analysis). A closer analysis shows that there are two types of clinical response in the population, a first group which possesses a worse response than the second group and at the same time the biomarker expression for the first group is generally higher following administration of at least one dose of a VEGF antagonist. An adjusted covariate analysis reveals that for each of the groups the relation of clinical benefit and clinical response is reversed, i.e., within the groups, lower expression levels are associated with better clinical response. The overall opposite effect was masked by the covariate type—and the covariate adjusted analysis as part of the prediction rule reversed the direction.

Multivariate Prediction (Hypothetical Example)

For a biomarker X it is found in a clinical trial population that high expression levels are slightly associated with a worse clinical response (univariate analysis). For a second biomarker Y a similar observation was made by univariate analysis. The combination of X and Y revealed that a good clinical response is seen if both biomarkers are low. This makes the rule to predict benefit if both biomarkers are below some cutoffs (AND—connection of a Heaviside prediction function). For the combination rule, a simple rule no longer applies in a univariate sense; for example, having low expression levels in X will not automatically predict a better clinical response.

These simple examples show that prediction rules with and without covariates cannot be judged on the univariate level of each biomarker. The combination of multiple biomarkers plus a potential adjustment by covariates does not allow assigning simple relationships to single biomarkers. Since the marker genes, in particular in serum, may be used in multiple-marker prediction models potentially including other clinical covariates, the direction of a beneficial effect of a single marker gene within such models cannot be determined in a simple way, and may contradict the direction found in univariate analyses, i.e., the situation as described for the single marker gene.

A clinician may use any of several methods known in the art to measure the effectiveness of a particular dosage scheme of a VEGF antagonist. For example, in vivo imaging (e.g., MRI) can be used to determine the tumor size and to identify any metastases to determine relative effective responsiveness to the therapy. Dosage regimens may be adjusted to provide the optimum desired response (e.g., a therapeutic response). For example, a dose may be administered, several divided doses may be administered over time or the dose may be proportionally reduced or increased as indicated by exigencies of the therapeutic situation.

A physician having ordinary skill in the art can readily determine and prescribe the effective amount of the pharmaceutical composition required, depending on such factors as the particular antagonist type. For example, the physician could start with doses of such antagonist, such as an anti-VEGF antibody, employed in the pharmaceutical composition at levels lower than that required in order to achieve the desired therapeutic effect and gradually increase the dosage until the desired effect is achieved. The effectiveness of a given dose or treatment regimen of the antagonist can be determined, for example, by assessing signs and symptoms in the patient using standard measures of efficacy.

In yet another embodiment, the subject is treated with the same antagonist, such as anti-VEGF antibody at least twice. Thus, the initial and second antagonist exposures are preferably with the same antagonist, and more preferably all antagonist exposures are with the same antagonist, i.e., treatment for the first two exposures, and preferably all exposures, is with one type of VEGF antagonist, for example, an antagonist that binds to VEGF, such as an anti-VEGF antibody, e.g., all with bevacizumab.

In all the inventive methods set forth herein, the antagonist (such as an antibody that binds to VEGF) may be unconjugated, such as a naked antibody, or may be conjugated with another molecule for further effectiveness, such as, for example, to improve half-life.

The preferred antagonist antibody herein is a chimeric, humanized, or human antibody, more preferably, an anti-VEGF antibody, and most preferably bevacizumab.

In another embodiment, the VEGF antagonist (e.g., an anti-VEGF antibody) is the only medicament administered to the subject.

In one embodiment, the antagonist is an anti-VEGF antibody that is administered at a dose of about 100 or 400 mg every 1, 2, 3, or 4 weeks or is administered a dose of about 1, 3, 5, 10, 15, or 20 mg/kg every 1, 2, 3, or 4 weeks. The dose may be administered as a single dose or as multiple doses (e.g., 2 or 3 doses), such as infusions.

In yet another aspect, the invention provides, after the diagnosis step, a method of determining whether to continue administering a VEGF antagonist (e.g., an anti-VEGF antibody) to a subject with an angiogenic disorder comprising measuring reduction in tumor size, using imaging techniques, such as radiography and/or MRI, after administration of the antagonist a first time, measuring reduction in tumor size in the subject, using imaging techniques such as radiography and/or MRI after administration of the antagonist a second time, comparing imaging findings in the subject at the first time and at the second time, and if the score is less at the second time than at the first time, continuing administration of the antagonist.

In a still further embodiment, a step is included in the treatment method to test the subject's response to treatment after the administration step to determine that the level of response is effective to treat the angiogenic disorder. For example, a step is included to test the imaging (radiographic and/or MRI) score after administration and compare it to baseline imaging results obtained before administration to determine if treatment is effective by measuring if, and by how much, it has been changed. This test may be repeated at various scheduled or unscheduled time intervals after the administration to determine maintenance of any partial or complete remission. Alternatively, the methods herein comprise a step of testing the subject, before administration, to see if one or more biomarkers or symptoms are present for angiogenic disorders, as set forth above.

In one embodiment of the invention, no other medicament than VEGF antagonist such as anti-VEGF antibody is administered to the subject to treat an angiogenic disorder.

In any of the methods herein, the VEGF antagonist may be administered in combination with an effective amount of a second medicament (where the VEGF antagonist (e.g., an anti-VEGF antibody) is a first medicament). Suitable second medicaments include, for example, an anti-neoplastic agent, a chemotherapeutic agent, a growth inhibitory agent, a cytotoxic agent, or combinations thereof.

All these second medicaments may be used in combination with each other or by themselves with the first medicament, so that the expression "second medicament" as used herein does not mean it is the only medicament in addition to the first medicament. Thus, the second medicament need not be a single medicament, but may constitute or comprise more than one such drug.

These second medicaments as set forth herein are generally used in the same dosages and with administration routes as used hereinbefore or about from 1 to 99% of the heretofore-employed dosages. If such second medicaments are used at all, preferably, they are used in lower amounts than if the first medicament were not present, especially in subsequent dosings beyond the initial dosing with the first medicament, so as to eliminate or reduce side effects caused thereby.

For the re-treatment methods described herein, where a second medicament is administered in an effective amount with an antagonist exposure, it may be administered with any exposure, for example, only with one exposure, or with more than one exposure. In one embodiment, the second medicament is administered with the initial exposure. In another embodiment, the second medicament is administered with the initial and second exposures. In a still further embodiment, the second medicament is administered with all exposures. It is preferred that after the initial exposure, such as of steroid, the amount of such second medicament is reduced or eliminated so as to reduce the exposure of the subject to an agent with side effects such as prednisone, prednisolone, methylprednisolone, and cyclophosphamide.

The combined administration of a second medicament includes co-administration (concurrent administration), using separate formulations or a single pharmaceutical formulation, and consecutive administration in either order, wherein preferably there is a time period while both (or all) active agents (medicaments) simultaneously exert their biological activities.

The antagonist herein is administered by any suitable means, including parenteral, topical, subcutaneous, intraperitoneal, intrapulmonary, intranasal, and/or intralesional administration. Parenteral infusions include intramuscular, intravenous (i.v.), intraarterial, intraperitoneal, or subcutaneous administration. Intrathecal administration is also contemplated. In addition, the antagonist may suitably be administered by pulse infusion, e.g., with declining doses of the antagonist. Preferably, the dosing is given intravenously or subcutaneously, and more preferably by intravenous infusion(s).

If multiple exposures of antagonist are provided, each exposure may be provided using the same or a different administration means. In one embodiment, each exposure is by intravenous administration. In another embodiment, each exposure is given by subcutaneous administration. In yet another embodiment, the exposures are given by both intravenous and subcutaneous administration.

In one embodiment, the antagonist such as an anti-VEGF antibody is administered as a slow intravenous infusion rather than an intravenous push or bolus. For example, a steroid such as prednisolone or methylprednisolone (e.g., about 80-120 mg i.v., more specifically about 100 mg i.v.) is administered about 30 minutes prior to any infusion of the anti-VEGF antibody. The anti-VEGF antibody is, for example, infused through a dedicated line.

For the initial dose of a multi-dose exposure to anti-VEGF antibody, or for the single dose if the exposure involves only one dose, such infusion is preferably commenced at a rate of about 50 mg/hour. This may be escalated, e.g., at a rate of about 50 mg/hour increments every about 30 minutes to a maximum of about 400 mg/hour. However, if the subject is experiencing an infusion-related reaction, the infusion rate is preferably reduced, e.g., to half the current rate, e.g., from 100 mg/hour to 50 mg/hour. Preferably, the infusion of such dose of anti-VEGF antibody (e.g., an about 1000-mg total dose) is completed at about 255 minutes (4 hours 15 min.). Optionally, the subjects receive a prophylactic treatment of acetaminophen/paracetamol (e.g., about 1 g) and diphenhydramine HCl (e.g., about 50 mg or equivalent dose of similar agent) by mouth about 30 to 60 minutes prior to the start of an infusion.

If more than one infusion (dose) of anti-VEGF antibody is given to achieve the total exposure, the second or subsequent anti-VEGF antibody infusions in this infusion embodiment are preferably commenced at a higher rate than the initial infusion, e.g., at about 100 mg/hour. This rate may be escalated, e.g., at a rate of about 100 mg/hour increments every about 30 minutes to a maximum of about 400 mg/hour. Subjects who experience an infusion-related reaction preferably have the infusion rate reduced to half that rate, e.g., from 100 mg/hour to 50 mg/hour. Preferably, the infusion of such second or subsequent dose of anti-VEGF antibody (e.g., an about 1000-mg total dose) is completed by about 195 minutes (3 hours 15 minutes).

In a preferred embodiment, the antagonist is an anti-VEGF antibody and is administered in a dose of about 0.4 to 4 grams, and more preferably the antibody is administered in a dose of about 0.4 to 1.3 grams at a frequency of one to four doses within a period of about one month. Still more preferably, the dose is about 500 mg to 1.2 grams, and in other embodiments is about 750 mg to 1.1 grams. In such aspects, the antagonist is preferably administered in two to three doses, and/or is administered within a period of about 2 to 3 weeks.

In one embodiment, the subject has never been previously administered any drug(s) to treat the angiogenic disorder. In another embodiment, the subject or patient has been previously administered one or more medicaments(s) to treat the angiogenic disorder. In a further embodiment, the subject or patient was not responsive to one or more of the medicaments that had been previously administered. Such drugs to which the subject may be non-responsive include, for example, anti-neoplastic agents, chemotherapeutic agents, cytotoxic agents, and/or growth inhibitory agents. More particularly, the drugs to which the subject may be non-responsive include VEGF antagonists such as anti-VEGF antibodies. In a further aspect, such antagonists include an antibody or immunoadhesin, such that re-treatment is contemplated with one or more antibodies or immunoadhesins of this invention to which the subject was formerly non-responsive.

IV. Treatment with the Antagonist

Once the patient population most responsive or sensitive to treatment with the antagonist has been identified, treatment with the antagonist herein, alone or in combination with other medicaments, results in an improvement in the angiogenic disorder. For instance, such treatment may result in a reduction in tumor size or progression free survival. Moreover, treatment with the combination of an antagonist herein and at least one second medicament(s) preferably results in an additive, more preferably synergistic (or greater than additive) therapeutic benefit to the patient. Preferably, in this combination method the timing between at least one administration of the second medicament and at least one administration of the antagonist herein is about one month or less, more preferably, about two weeks or less. Administration of VEGF antagonists, as described herein, is optionally included in the invention. Thus, in a further embodiment, the invention provides a method of treating cancer (e.g., colorectal cancer, breast cancer, lung cancer, or glioblastoma) in a patient by administration of a VEGF antagonist (e.g., an anti-VEGF antibody, such as bevacizumab), wherein the patient is or has been identified as being one that will benefit from such treatment, according to the methods described herein.

It will be appreciated by one of skill in the medical arts that the exact manner of administering to said patient a therapeutically effective amount of a VEGF antagonist following a diagnosis of a patient's likely responsiveness to the antagonist will be at the discretion of the attending physician. The mode of administration, including dosage, combination with other agents, timing and frequency of administration, and the like, may be affected by the diagnosis of a patient's likely responsiveness to such antagonist, as well as the patient's condition and history. Thus, even patients diagnosed with an angiogenic disorder who are predicted to be relatively insensitive to the antagonist may still benefit from treatment therewith, particularly in combination with other agents, including agents that may alter a patient's responsiveness to the antagonist.

The composition comprising an antagonist will be formulated, dosed, and administered in a fashion consistent with good medical practice. Factors for consideration in this context include the particular type of angiogenic disorder being treated, the particular mammal being treated, the clinical condition of the individual patient, the cause of the angiogenic disorder, the site of delivery of the agent, possible side-effects, the type of antagonist, the method of administration, the scheduling of administration, and other factors known to medical practitioners. The effective amount of the antagonist to be administered will be governed by such considerations.

As a general proposition, the effective amount of the antagonist administered parenterally per dose will be in the range of about 20 mg to about 5000 mg, by one or more dosages. Exemplary dosage regimens for antibodies such as anti-VEGF antibodies include 100 or 400 mg every 1, 2, 3, or 4 weeks or is administered a dose of about 1, 3, 5, 10, 15, or 20 mg/kg every 1, 2, 3, or 4 weeks. The dose may be administered as a single dose or as multiple doses (e.g., 2 or 3 doses), such as infusions.

As noted above, however, these suggested amounts of antagonist are subject to a great deal of therapeutic discretion. The key factor in selecting an appropriate dose and scheduling is the result obtained, as indicated above. In some embodiments, the antagonist is administered as close to the first sign, diagnosis, appearance, or occurrence of the angiogenic disorder as possible.

The antagonist is administered by any suitable means, including parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated. In addition, the antagonist may suitably be administered by pulse infusion, e.g., with declining doses of the antagonist. Most preferably, the dosing is given by intravenous injections.

One may administer a second medicament, as noted above, with the antagonists herein. The combined administration includes co-administration, using separate formulations or a single pharmaceutical formulation, and consecutive administration in either order, wherein preferably there is a time period while both (or all) active agents simultaneously exert their biological activities.

Aside from administration of antagonists to the patient by traditional routes as noted above, the present invention includes administration by gene therapy. Such administration of nucleic acids encoding the antagonist is encompassed by the expression "administering an effective amount of an antagonist". See, for example, WO 1996/07321 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antagonist is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent specific for the target cells, such as an antibody specific for a cell-surface membrane protein on the target cell, a ligand for a receptor on the target cell, etc. Where liposomes are employed, proteins that bind to a cell-surface membrane protein associated with endocytosis may be used for targeting and/or to facilitate uptake, e.g., capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.* 262: 4429-4432 (1987); and Wagner et al., *PNAS USA* 87:3410-3414 (1990). Gene-marking and gene-therapy protocols are described, for example, in Anderson et al., *Science* 256:808-813 (1992) and WO 1993/25673.

A VEGF antagonist may be combined in a pharmaceutical combination formulation, or dosing regimen as combination therapy, with at least one additional compound having anti-cancer properties. The at least one additional compound of the pharmaceutical combination formulation or dosing regimen preferably has complementary activities to the VEGF antagonist composition such that they do not adversely affect each other.

The at least one additional compound may be a chemotherapeutic agent, a cytotoxic agent, a cytokine, a growth inhibitory agent, an anti-hormonal agent, and combinations thereof. Such molecules are suitably present in combination in amounts that are effective for the purpose intended. A pharmaceutical composition containing an VEGF antagonist (e.g., an anti-VEGF antibody) may also comprise a therapeutically effective amount of an anti-neoplastic agent, a chemotherapeutic agent a growth inhibitory agent, a cytotoxic agent, or combinations thereof.

In one aspect, the first compound is an anti-VEGF antibody and the at least one additional compound is a therapeutic antibody other than an anti-VEGF antibody. In one embodiment, the at least one additional compound is an antibody that binds a cancer cell surface marker. In one embodiment the at least one additional compound is an anti-HER2 antibody, trastuzumab (e.g., Herceptin®, Genentech, Inc., South San Francisco, Calif.). In one embodiment the at least one additional compound is an anti-HER2 antibody, pertuzumab (Omnitarg™ Genentech, Inc., South San Francisco, Calif., see U.S. Pat. No. 6,949,245). In an embodiment, the at least one additional compound is an antibody (either a naked antibody or an ADC), and the additional antibody is a second, third, fourth, fifth, sixth antibody or more, such that a combination of such second, third, fourth, fifth, sixth, or more antibodies (either naked or as an ADC) is efficacious in treating an angiogenic disorder.

Other therapeutic regimens in accordance with this invention may include administration of a VEGF-antagonist anti-cancer agent and, including without limitation radiation therapy and/or bone marrow and peripheral blood transplants, and/or a cytotoxic agent, a chemotherapeutic agent, or a growth inhibitory agent. In one of such embodiments, a chemotherapeutic agent is an agent or a combination of agents such as, for example, cyclophosphamide, hydroxydaunorubicin, adriamycin, doxorubicin, vincristine (ONCOVIN™), prednisolone, CHOP, CVP, or COP, or immunotherapeutics such as anti-PSCA, anti-HER2 (e.g., HERCEPTIN®, OMNITARG™). The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

In one embodiment, treatment with an anti-VEGF antibody involves the combined administration of an anticancer agent identified herein, and one or more chemotherapeutic agents or growth inhibitory agents, including coadministration of cocktails of different chemotherapeutic agents. Chemotherapeutic agents include taxanes (such as paclitaxel and docetaxel) and/or anthracycline antibiotics. Preparation and dosing schedules for such chemotherapeutic agents may be used according to manufacturer's instructions or as determined empirically by the skilled practitioner. Preparation and dosing schedules for such chemotherapy are also described in "Chemotherapy Service", (1992) Ed., M. C. Perry, Williams & Wilkins, Baltimore, Md.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

For the prevention or treatment of disease, the appropriate dosage of the additional therapeutic agent will depend on the type of disease to be treated, the type of antibody, the severity and course of the disease, whether the VEGF antagonist and additional agent are administered for preventive or therapeutic purposes, previous therapy, the patient's clinical history and response to the VEGF antagonist and additional agent, and the discretion of the attending physician. The VEGF antagonist and additional agent are suitably administered to the patient at one time or over a series of treatments. The VEGF antagonist is typically administered as set forth above. Depending on the type and severity of the disease, about 20 mg/m$^2$ to 600 mg/m$^2$ of the additional agent is an initial candidate dosage for administration to the patient, whether, for example, by one or more separate administrations, or by continuous infusion. One typical daily dosage might range from about or about 20 mg/m$^2$, 85 mg/m$^2$, 90 mg/m$^2$, 125 mg/m$^2$, 200 mg/m$^2$, 400 mg/m$^2$, 500 mg/m$^2$ or more, depending on the factors mentioned above. For repeated administrations over several days or longer, depending on the condition, the treatment is sustained until a desired suppression of disease symptoms occurs. Thus, one or more doses of about 20 mg/m$^2$, 85 mg/m$^2$, 90 mg/m$^2$, 125 mg/m$^2$, 200 mg/m$^2$, 400 mg/m$^2$, 500 mg/m$^2$, 600 mg/m$^2$ (or any combination thereof) may be administered to the patient. Such doses may be administered intermittently, e.g., every week or every two, three weeks, four, five, or six (e.g., such that the patient receives from about two to about twenty, e.g. about six doses of the additional agent). An initial higher loading dose, followed by one or more lower doses may be administered. However, other dosage regimens may be useful. The progress of this therapy is easily monitored by conventional techniques and assays.

V. Pharmaceutical Formulations

Therapeutic formulations of the antagonists used in accordance with the present invention are prepared for storage by mixing the antagonist having the desired degree of purity with optional pharmaceutically acceptable carriers, excipients, or stabilizers in the form of lyophilized formulations or aqueous solutions. For general information concerning formulations, see, e.g., Gilman et al., (eds.) (1990), *The Pharmacological Bases of Therapeutics*, 8th Ed., Pergamon Press; A. Gennaro (ed.), Remington's Pharmaceutical Sciences, 18th Edition, (1990), Mack Publishing Co., Eastori, Pa.; Avis et al., (eds.) (1993) *Pharmaceutical Dosage Forms: Parenteral Medications* Dekker, New York; Lieberman et al., (eds.) (1990) *Pharmaceutical Dosage Forms Tablets* Dekker, New York; and Lieberman et al., (eds.) (1990), *Pharmaceutical Dosage Forms Disperse Systems* Dekker, New York, Kenneth A. Walters (ed.) (2002) *Dermatological and Transdermal Formulations* (Drugs and the Pharmaceutical Sciences), Vol 119, Marcel Dekker.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

Exemplary anti-VEGF antibody formulations are described in U.S. Pat. No. 6,884,879. In certain embodiments anti-VEGF antibodies are formulated at 25 mg/mL in single use vials. In certain embodiments, 100 mg of the anti-VEGF antibodies are formulated in 240 mg α,α-trehalose dihydrate, 23.2 mg sodium phosphate (monobasic, monohydrate), 4.8 mg sodium phosphate (dibasic anhydrous), 1.6 mg polysorbate 20, and water for injection, USP. In certain embodiments, 400 mg of the anti-VEGF antibodies are formulated in 960 mg α,α-trehalose dihydrate, 92.8 mg sodium phosphate (monobasic, monohydrate), 19.2 mg sodium phosphate (dibasic anhydrous), 6.4 mg polysorbate 20, and water for injection, USP.

Lyophilized formulations adapted for subcutaneous administration are described, for example, in U.S. Pat. No. 6,267,958 (Andya et al.). Such lyophilized formulations may be reconstituted with a suitable diluent to a high protein concentration and the reconstituted formulation may be administered subcutaneously to the mammal to be treated herein.

Crystallized forms of the antagonist are also contemplated. See, for example, US 2002/0136719A1.

The formulation herein may also contain more than one active compound (a second medicament as noted above), preferably those with complementary activities that do not adversely affect each other. The type and effective amounts of such medicaments depend, for example, on the amount and type of VEGF antagonist present in the formulation, and clinical parameters of the subjects. The preferred such second medicaments are noted above.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, nondegradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

TABLE 1

| | | | | | | | |
|---|---|---|---|---|---|---|---|
| ABCC9 | CD97 | DLC1 | GIMAP5 | LEPREL2 | PCDH18 | RRAS | THSD1 |
| ACVRL1 | CD105 | DLL4 | GIMAP6 | LHFP | PDGFB | S1PR1 | THY1 |
| ADAM12 | CD144 | DPYS | GJA4 | LIX1L | PDGFD | S1PR3 | TIMP3 |
| ADAMTS1 | CD276 | DUSP6 | GJC1 | LIMS2 | PDGFRB | SCARF1 | TMEM88 |
| ADAMTS2 | CARD11 | EBF2 | GPR4 | LMO2 | PHACTR2 | SEMA3F | TMEM204 |
| ADAMTS12 | CDC42EP1 | EFNB2 | GPR124 | LPAR6 | PLK2 | SEPT4 | TM4SF1 |
| AFAP1L2 | CDH11 | EGFL7 | HAPLN1 | LRP4 | PLVAP | SERPINE1 | TNFAIP2 |
| AHR | CDH5 | EHD4 | HEY2 | LRRC33 | PLXDC2 | SERPINH1 | TNNT2 |
| Alk1 | CDRT4 | ELTD1 | HEYL | LY6E | PPAP2A | SLC9A3R2 | TP53 |
| AMOTL1 | CES2 | EMCN | HIGD1B | MAPK12 | PPAP2B | SLC11A1 | TREML4 |
| ANGPT2 | CHST15 | ENG | HLX | MCAM | PPFIA4 | SLC5A2 | TRDN |
| ANXA1 | CLEC4D | ERG | HOXA3 | MECOM | PPM1F | SLC22A9 | TRIB2 |
| APLNR | CLEC6A | ESAM | HOXD8 | MED24 | PTAFR | SLC22A25 | TRIM5 |
| ARAP3 | CLEC14A | ESM1 | ICAM2 | MDFIC | PRICKLE2 | SLC43A3 | TSLP |
| ARHGAP29 | CLEC1A | ETS1 | ID1 | MEF2C | PROCR | SLFN5 | TSP1 |
| ARHGAP31 | CNN2 | F2R | IFI44 | MFGE8 | PRKCDBP | SNCG | TUSC5 |
| ART3 | COL15A1 | F2RL3 | IGFBP3 | MMRN2 | PRKCH | SOD3 | UBXN10 |
| ASB2 | COL18A1 | FAM198B | IL2RG | MYCT1 | PRND | SOX7 | USHBP1 |
| ATP1B4 | COL1A2 | FANCI | INHBB | NAALAD2 | PRR5L | SOX18 | VAMP5 |
| BGN | COL4A1 | FBLN5 | ITPRIPL2 | NFIB | PTPRB | SPARC | VEGFR1 |
| BHMT2 | COL4A2 | FBN1 | JUB | NHSL2 | PTPRG | SPIC | VEGFR2 |
| BTNL9 | COL4A3 | FKBP10 | KANK3 | NID1 | PTPRM | SRGN | VEGFR3 |
| BMPR2 | COL8A1 | FLI1 | KCNE3 | NID2 | QKI | SPRY4 | VIM |
| BPIFB1 | COMMD7 | FLT1 | KDR | NNMT | RAPGEF3 | STAT1 | WISP1 |
| BST2 | CRTAM | FMOD | KIAA1274 | NOS3 | RAPGEF5 | STEAP4 | WWTR1 |
| C3orf64 | CSPG4 | FREM1 | KIAA1462 | NOTCH1 | RASIP1 | STON1 | ZFP36L1 |
| C8orf4 | CTGF | FSTL1 | KLHL4 | NRARP | RASGRP3 | STON1-GTF2A1L | ZNF521 |
| C13orf15 | CTTNBP2NL | FXYD5 | KLHL5 | NRP1 | RBP7 | ST8SIA4 | |
| C1S | CYYR1 | GAS6 | KLHL6 | NRP2 | RBMS1 | ST8SIA6 | |
| CAV1 | DAPK2 | GAS7 | KLRB1 | NRXN3 | RGS5 | SWAP70 | |
| CCND1 | DCHS1 | GIMAP1 | KPNA7 | P2RX7 | REST | TEK | |
| CD34 | DDAH1 | GIMAP2 | LAMA4 | PBX2 | RHOJ | TFAP2C | |
| CD40 | DEF6 | GIMAP3 | LAMB1 | PCDH12 | RIN3 | THBS1 | |
| CD93 | DKK2 | GIMAP4 | LATS2 | PCDH17 | ROBO4 | THBS2 | |

TABLE 2

Alk1
CD34
CD105
CD144
Col4a1
Col4a2
Dll4
EFNB2
EGFL7
ESM1
LAMA4
NG2
Nid2
Notch1
NRP1
NRP2
RGS5
Sema3f
TSP1
VEGFR1
VEGFR2
VEGFR3
VIM

EXAMPLES

The following examples are provided to illustrate, but not to limit the presently claimed invention.

Example 1. Materials and Methods

Mouse Strains & Models

We obtained RIP-TβAg mice from Exelixis, Inc. and Beige Nude XID mice from Harlan. Animals were housed and cared for according to guidelines from the Institutional Animal Care and Use Committee (IACUC) at Genentech, Inc.

Treatment Regimens and Dosing

All dosing regimens were carried out according to IACUC guidelines. Study animals were monitored daily and body weights were measured at least twice weekly. Procedures used for intracranial tumor establishment, including monitoring of tumor growth and response to therapy by bioluminescence imaging, have previously been described (Ozawa and James. *J Vis Exp.* 41: 1-5, 2010). The anti-vasculature endothelial growth factor (VEGF) monoclonal antibody B20-4.1.1, anti-Ragweed (control) and anti-Dll4 were prepared and purified as previously described (Fuh et al. *J Biol. Chem.* 281: 6625-6631, 2006), and dosed at 5 or 10 mg/kg twice weekly by intraperitoneal (i.p.) injection for all experiments in immuno-compromised mice and once weekly (at 5 mg/kg) in RIP-TβAg mice. Sunitinib was dosed at 60 mg/kg daily by oral gavage. Wound healing assays were carried out as previously described in Bais et al. (*Cell.* 141: 166-177, 2010).

Immunofluorescent Staining & Histological Quantitation

Whole pancreata dissected from tumor-bearing RIP-TβAg mice were incubated in sucrose (30%) for 5-10 min at 4° C., followed by washing with PBS (twice 15 minutes each). Pancreata were then placed in cryomolds containing Optimum Cutting Temperature (OCT, Sakura Finetek) medium and were maintained at −70° C. Sections (6 μm) of pancreata were cut from each OCT block using a cryostat instrument (Leica Microsystems) and were maintained at −70° C. until used for staining. For immunofluorescent staining, frozen sections were air-dried at room temperature and fixed with cold acetone for 5-10 minutes. Then sections were dried again and blocked for 30-60 minutes with a buffer containing 2.5% BSA and 5% donkey serum in PBS. Staining with primary antibodies diluted in blocking buffer (dilutions as per manufacturer's guidelines) was carried out overnight at 4° C. Sections were then washed with PBS and exposed to secondary antibodies diluted 1:300 in blocking buffer for 30-60 minutes, and then washed again in PBS. Finally sections were mounted in DAKO (DAKO) containing 4',6-diamidino-2-phenylindole (DAPI, Molecular Probes) for nuclear visualization.

The following antibodies were used for immunofluorescent staining: primary rat anti-mouse MECA-32 antibody (Invitrogen, Inc.), rabbit anti-Ki67, and clone SP6 (Research Diagnostics, Inc.). Secondary antibodies included Alexa-594 conjugated donkey anti-rat and anti-rabbit and Alexa-488 conjugated donkey anti-rabbit and goat anti-chicken (Invitrogen, Inc.). Tumors on stained slides were identified microscopically and photographed using an Axioskop and Axiovision Software (Zeiss, Inc.), and histological quantification on images was performed using customized algorithms in Metamorph software (Molecular Dynamics). At each time point, the mean measurement was calculated from at least 3-5 images per islet/tumor×5 tumors from each mouse×3 mice=45-75 images/time point/treatment from 15 independent lesions. For micro-vascular density (MVD) analyses in implanted tumor models, tumors from 6 mice per treatment group were collected and embedded in O.C.T. blocks. Tissues were cryo-sectioned to 16-μm thickness on Leica CM3050S, and stained with CD31 antibody (BD Biosciences). Images were acquired with Zeiss AxioImager Z1 fluorescence microscope controlled by TissueFAXS software. Image files were loaded into the TissueStudio analysis package (v1.5, Definiens). Necrotic tissues and staining artifacts such as skin tissues and folds were automatically identified and excluded based on nuclei staining. Vessel density was calculated as the ratio of CD31-positive pixels to the total viable tumor area.

Microarray Experiments

Total RNA was extracted from control and anti-VEGF-treated RIP-TβAg tumors after 7 days of treatment as follows: mice were anesthetized using 0.25% Avertin, injected intraperitoneally according to weight. The abdominal cavity was opened to access the pancreatic duct and perfuse the pancreas via the common bile duct. The pancreas was perfused with approximately 2.5 ml of Liberase TL (Roche) diluted as per the manufacturer's instructions. The pancreas was then dissected out of the abdominal cavity and tumor further macro-dissected away from the exocrine pancreas. Tumors were suspended in fresh perfusion solution and agitated at 37° C. for 5-6 minutes and then re-examined under a dissection microscope and any remaining fragments of exocrine pancreas removed. Clean tumors were then flash-frozen in RNAlater solution (Qiagen, Inc.). For all implant experiments in immune-deficient mice, animals were euthanized at the end of the study interval and tumors dissected out and snap frozen. Total RNA was extracted and microarrays run using Agilent Whole Mouse Genome 44K arrays, Affymetrix HGU133-plus2, or Agilent Whole Human Genome arrays according to manufacturer's instructions.

Cell Culture

D551 (ATCC) skin fibroblast cells were cultured in M199 medium (Invitrogen), supplemented with fetal bovine serum (Sigma-Aldrich), penicillin (100 units/mL), streptomycin (100 μg/mL). Primary human umbilical vascular endothelial cells (HUVEC) were purchased from (Lonza Walkersville), and maintained in EGM-2 medium (Lonza Walkersville). Condition medium: D551 cells were grown to 90% confluence, changed medium to EGM-2, after 7 days of incubation, the supernatant was collected and stored at 4° C.

HUVEC Transfection and Sprouting Assay

COL4A2, NID2, and MEST gene expression silencing: cells were grown to 70% confluence, and siRNA were transfected using the DharmaFECT1 according to the manufacturer's instructions (Thermo Scientific). The final concentration of all siRNA for transfection was 12.5 nM, and mRNA downregulation for each gene was confirmed by qRT-PCR. 24 hours after transfection, cells were trypsinized and mixed with Cytodex microcarrier beads (Sigma-Aldrich) in a ratio of $1 \times 10^6$ cells per 2,500 beads. Coating was performed for four hours at 37° C. and mixtures shaken by hand every 20 minutes. Coated beads were then transferred to a 6-well dish, and left for 18-20 hours in EGM-2 at 37° C. and 5% $CO_2$. The following day, coated beads were washed with EGM-2, and dissolved in a solution of fibrinogen (2 mg ml-1; Sigma-Aldrich) in EGM-2. The solution with about 200 HUVEC coated beads was added to 0.625 U $ml^{-1}$ of thrombin (Sigma) in one well of a 24-well tissue culture plate. $8 \times 10^4$ skin fibroblast cells (D551) were plated on top of the clot and incubated with 2 ml D551 condition medium/EGM-2 (1:3) containing 20 ug/ml of antibodies. The medium was replaced every 2 days and assays were terminated at day 4. HUVEC sprouts were visualized by immunostaining in fibrin gels fixed in 4% paraformaldehyde (PFA) for 2 hrs at RT, then blocked with block buffer (DAKO) for 4 hrs at RT, incubated with Alexa Fluor 488 phalloidin (1:100) and Hoecsht 33258 (1:1000) (Invitrogen) overnight at 4° C. followed by imaging. Image Xpress Micro was used for capturing images and HUVEC sprouting was analyzed in MetaXpress software. Three components of vessel growth were measured. The total outgrowth represents the cumulative length of all sprouts per bead, the mean outgrowth represents the number of sprout bifurcations per bead, and the total processes per beads were determined by counting the number of sprouts originating directly from the cells lining the surface of the bead. For statistical analysis, 4 wells were assessed for each condition and each experiment was repeated 3 times.

Quantitative Gene Expression Analyses

RNA was prepared with RNeasy Mini kit (Qiagen) according to the manufacturer's protocol. 500 ng total RNA was subjected to reverse transcription using the High Capacity cDNA reverse transcription kit (Applied Biosystems). The real-time PCR was run on the Applied Biosystems 7500 machine. Taqman probes for all gene tested were acquired from Applied Biosystems. Relative expression levels of each gene were normalized to actin.

Determination of Signature Gene Expression in Clinical Samples

Sections from archival tumor samples from patients enrolled in the XELOX treatment arms of NO 16966 were evaluated by a pathologist and high tumor content area macro-dissected for subsequent RNA isolation using the FFPE RNA isolation kit (Roche; 7-10 sections per patient). RNA levels were assessed after cDNA synthesis following standard techniques, with the qPCR protocol on the Fluidigm Biomark platform according to the manufacturer's protocol.

Gene Signature Derivation and Application

The log$_2$ ratio intensity values from Agilent WMG microarrays and the Robust Multi-array Average (RMA) normalized intensities (also on the logarithmic scale) from Affymetrix Mouse430.2 microarrays were imported into R as expression sets using the package "Biobase," and a linear model was fitted to each feature using the functions "lmFit" and "eBayes" in the "limma" package. Features that were significantly (p<0.05) down-regulated in anti-VEGF treated samples (as compared to anti-ragweed control treated samples) were retained and translated to EntrezGene identifiers. The union of these genes was taken as representative of the VEGF-responsive vasculature. The extent to which this VDV gene expression signature varied in other experiments was determined by fitting a linear model to the microarray data using the "limma" package (as above) and calculating the mean of the t-statistics from gene in the signature according to the method of Falcon and Gentleman (*Bioinformatics*. 23: 257-258, 2007).

Statistical Methods of Biomarker Selection

The statistical tasks can comprise the following steps:
1. Pre-selection of candidate biomarkers
2. Pre-selection of relevant clinical efficacy response predictive covariates
3. Selection of biomarker prediction functions at a univariate level
4. Selection of biomarker prediction functions including clinical covariates at a univariate level
5. Selection of biomarker prediction functions at a multivariate level
6. Selection of biomarker prediction functions including clinical covariates at a multivariate level The following text details the different steps:

1: Pre-Selection of Candidate Biomarkers

The statistical pre-selection of candidate biomarkers is oriented towards the strength of association with measures of clinical benefit. For this purpose the different clinical endpoints may be transformed in derived surrogate scores, as, e.g., an ordinal assignment of the degree of clinical benefit scores regarding TTP that avoid censored observations. These surrogate transformed measures can be easily used for simple correlation analysis, e.g. by the non-parametric Spearman rank correlation approach. An alternative is to use the biomarker measurements as metric covariates in time-to-event regression models, as, e.g., Cox proportional hazard regression. Depending on the statistical distribution of the biomarker values, this step may require some pre-processing, as, for example, variance-stabilizing transformations and the use of suitable scales or, alternatively, a standardization step such as using percentiles instead of raw measurements. A further approach is inspection of bivariate scatter plots, for example, by displaying the scatter of x-axis=biomarker value, y-axis=measure of clinical benefit) on a single-patient basis. Some non-parametric regression line as achieved, for example, by smoothing splines can be useful to visualize the association of biomarker and clinical benefit.

The goal of these different approaches is the pre-selection of biomarker candidates that show some association with clinical benefit in at least one of the benefit measures employed, while results for other measures are not contradictory. When there are available control groups, then differences in association of biomarkers with clinical benefit in the different arms could be a sign of differential prediction that makes the biomarker(s) eligible for further consideration.

2: Pre-Selection of Relevant Clinical Efficacy Response Predictive Covariates

The statistical pre-selection of clinical covariates as defined herein parallels the approaches for pre-selecting biomarkers and is also oriented towards the strength of association with measures of clinical benefit. So in principle the same methods apply as considered under 1 above. In addition to statistical criteria, criteria from clinical experience and theoretical knowledge may apply to pre-select relevant clinical covariates.

The predictive value of clinical covariates could interact with the predictive value of the biomarkers. They will be considered for refined prediction rules, if necessary.

3: Selection of Biomarker Prediction Functions at a Univariate Level

The term "prediction function" will be used in a general sense to mean a numerical function of a biomarker measurement that results in a number scaled to imply the target prediction.

A simple example is the choice of the Heaviside function for a specific cutoff c and a biomarker measurement x, where the binary prediction A or B is to be made, then if H (x−c)=0, then predict A. If H (x−c)=1, then predict B.

This is probably the most common way of using univariate biomarker measurements in prediction rules. The definition of "prediction function" as noted above includes referral to an existing training data set that can be used to explore the prediction possibilities. Different routes can be taken to achieve a suitable cutoff c from the training set. First, the scatterplot with smoothing spline mentioned under 1 can be used to define the cutoff. Alternatively, some percentile of the distribution could be chosen, e.g., the median or a quartile. Cutoffs can also be systematically extracted by investigating all possible cutoffs according to their prediction potential with regard to the measures of clinical benefit. Then, these results can be plotted to allow for an either manual selection or to employ some search algorithm for optimality. This can be realized based on certain clinical endpoints using a Cox model, wherein at each test cutoff the biomarker is used as a binary covariate. Then the results for the clinical endpoints can be considered together to chose a cutoff that shows prediction in line with both endpoints.

Another uncommon approach for choosing a prediction function can be based on a fixed-parameter Cox regression model obtained from the training set with biomarker values (possibly transformed) as covariate. A further possibility is to base the decision on some likelihood ratio (or monotonic transform of it), where the target probability densities are pre-determined in the training set for separation of the prediction states. Then the biomarker would be plugged into some function of predictive criteria.

4: Selection of Biomarker Prediction Functions Including Clinical Covariates at a Univariate Level Univariate refers to using only one biomarker—with regard to clinical covariates, this can be a multivariate model. This approach parallels the search without clinical covariates, except that the methods should allow for incorporating the relevant covariate information. The scatterplot method of choosing a cutoff allows only a limited use of covariates, e.g., a binary covariate could be color coded within the plot. If the analysis relies on some regression approach, then the use of covariates (also many of them at a time) is usually facilitated. The cutoff search based on the Cox model described under 3 above allows for an easy incorporation of covariates and thereby leads to a covariate adjusted univariate cutoff search. The adjustment by covariates may be done as covariates in the model or via the inclusion in a stratified analysis.

Also the other choices of prediction functions allow for the incorporation of covariates.

This is straightforward for the Cox model choice as prediction function. This includes the option to estimate the influence of covariates on an interaction level, which means that, e.g., for different age groups different predictive criteria apply.

For the likelihood ratio type of prediction functions, the prediction densities must be estimated including covariates. For this purpose, the methodology of multivariate pattern recognition can be used or the biomarker values can be adjusted by multiple regression on the covariates (prior to density estimation).

The CART technology (*Classification and Regression Trees*; Breiman et al. (Wadsworth, Inc.: New York, 1984) can be used for this purpose, employing a biomarker (raw measurement level) plus clinical covariates and utilizing a clinical benefit measure as response. Cutoffs are searched and a decision-tree type of function will be found involving the covariates for prediction. The cutoffs and algorithms chosen by CART are frequently close to optimal and may be combined and unified by considering different clinical benefit measures.

5: Selection of Biomarker Prediction Functions at a Multivariate Level

When there are several biomarker candidates that maintain their prediction potential within the different univariate prediction function choices, then a further improvement may be achieved by combinations of biomarkers, i.e., considering multivariate prediction functions.

Based on the simple Heaviside function model, combinations of biomarkers may be evaluated, e.g., by considering bivariate scatterplots of biomarker values where optimal cutoffs are indicated. Then a combination of biomarkers can be achieved by combining different Heaviside function by the logical "AND" and "OR" operators to achieve an improved prediction.

The CART technology can be used for this purpose, employing multiple biomarkers (raw measurement level) and a clinical benefit measure as response, to achieve cutoffs for biomarkers and decision-tree type of functions for prediction. The cutoffs and algorithms chosen by CART are frequently close to optimal and may be combined and unified by considering different clinical benefit measures.

The Cox-regression can be employed on different levels. A first way is to incorporate the multiple biomarkers in a binary way (i.e., based on Heaviside functions with some cutoffs). The other option is to employ biomarkers in a metric way (after suitable transformations), or a mixture of the binary and metric approach. The evolving multivariate prediction function is of the Cox type as described under 3 above.

The multivariate likelihood ratio approach is difficult to implement, but presents another option for multivariate prediction functions.

6: Selection of Biomarker Prediction Functions Including Clinical Covariates at a Multivariate Level When there are relevant clinical covariates, then a further improvement may be achieved by combining multiple biomarkers with multiple clinical covariates. The different prediction function choices will be evaluated with respect to the possibilities to include clinical covariates.

Based on the simple logical combinations of Heaviside functions for the biomarkers, further covariates may be included to the prediction function based on the logistic regression model obtained in the training set.

The CART technology and the evolving decision trees can be easily used with additional covariates, which would include these in the prediction algorithm.

All prediction functions based on the Cox-regression can use further clinical covariates. The option exists to estimate the influence of covariates on an interaction level, which means that, e.g., for different age groups different predictive criteria apply.

The multivariate likelihood ratio approach is not directly extendible to the use of additional covariates.

Statistical Methods of Histological and Clinical Data Analysis

Quantitative histological data from various animal experiments were plotted using Microsoft Excel software. Student's t test was applied to compare data sets of interest and differences with p values <0.05 were considered significant. 103 biopsies out of 1017 patients from the XELOX (capecitabine and oxaliplatin)-containing arm in the NO16966 trial were analyzed for the gene expression of VDV genes. qRT-PCR values were normalized by the housekeeping genes and relative to a universal reference sample to derive delta-delta Ct values. Subsequently, the delta-delta Ct value of each of the 22 VDV genes was mean centered and variance scaled to a Z-score.

For each sample i for which all of the VDV genes were analyzed, a VDV signature score $(VDV_i)$ was calculated. The $VDV_i$ represents a weighted average of z-scores across the analyzed VDV genes and is given by the algorithm:

$$VDV_i = \frac{1}{\sqrt{n}} \sum_{g=1}^{n} Z_{g,i}$$

wherein $Z_{g,i}$ is the standardized z-score of the qRT-PCR value for gene g of sample i and n, in this instance, is 22. The $VDV_i$ value provides quantitative information regarding the extent to which the expression of a particular set of genes is collectively overexpressed or underexpressed relative to a centered mean.

To compare the clinical outcomes (PFS and OS) between marker and/or treatment subgroups, log-rank tests and Cox regression were used, with median time calculated by the Kaplan-Meier analysis. All statistical tests were two-sided.

Figure 1B:
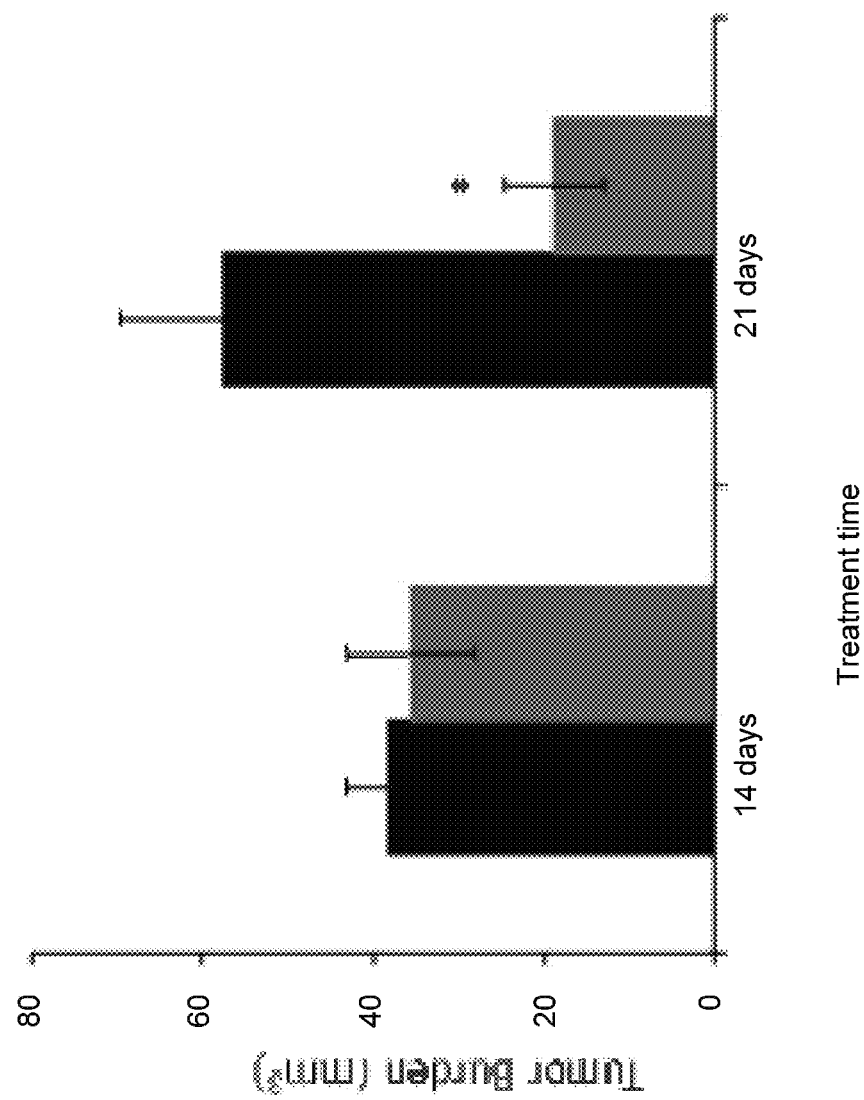
FIG. 1B is a graph showing the kinetics of anti-VEGF effects on tumor burden in the RIP-TβAg model. Tumor burden in anti-VEGF-treated mice (red bars) is significantly lower than control-treated mice (black bars) at 21 days, but not at 14 days on the study. *=p<0.05 (t-test), n=5-8 mice/group/time point.

Example 2. Identification of Genes Expressed in the Tumor Vascular Compartment Targeted by Anti-VEGF As a first step towards identification of direct in vivo biomarkers of VEGF pathway inhibition activity, we characterized the biological consequences of VEGF neutralization in an established transgenic murine model of pancreatic neuroendocrine tumors (PNETs). In the highly vascularized RIP-TβAg genetically engineered tumor mouse model (GEMM), anti-VEGF monoclonal antibody (mAb) treatment has previously been shown to have anti-tumor efficacy and to increase overall survival (Singh et al. *J. Pathology* 227(4): 417-430, 2012). Histological analyses of RIP-TβAg late-stage tumors showed that anti-VEGF treatment caused a rapid reduction in micro-vascular density (MVD), detectable at 72 hours post-treatment, and reaching a plateau of approximately 50% at day 7 (FIG. 1A, left). The anti-VEGF induced pruning of this fraction of the tumor vasculature (hereinafter referred to as "VEGF-dependent vasculature" or VDV) is not significantly reversed nor increased at later treatment time points (FIG. 1A, left). In these experiments, tumor vessel density and proliferative index was assessed histologically via MECA-32 staining (red, left) and Ki67 staining (red, right), respectively. Nuclei were counter-stained with DAPI (blue). In contrast to the observed rapid anti-vascular effects, the indirect anti-tumor effects of VEGF neutralization progressed more slowly: a reduction in the tumor proliferative index in the anti-VEGF treated group compared to the control (anti-ragweed) treated group was not observed at day 7 but obvious at day 14 (FIG. 1A, right), and a consequent reduction in tumor burden was only evident at day 21 (FIG. 1B). This suggests that at early time-points, the biological consequences of VEGF blockade in this model are primarily vascular specific.

Expression microarray analysis of whole tumors from animals treated for seven days with anti-VEGF showed that the vast majority of genes were unchanged in expression, as compared to tumors from animals treated with a control antibody. However, a small population of genes responded to anti-VEGF treatment with a significant (adjusted $p<0.01$) decrease in transcript abundance (Table 3). Interestingly, we observed no corresponding up-regulation of gene expression, suggesting that gene expression changes were primarily driven by physical elimination of VEGF-dependent tumor-associated endothelial cells (FIG. 1C and Table 3). As depicted in Table 3 below, the genes in the VDV signature were ordered by the extent of anti-VEGF response in the human IBC trial. Orthologs between human and mouse were mapped using the Ensembl Biomart, where "Log 2FC" represents the log(2) fold-change of the gene's expression post-Avastin treatment as compared to pre-treatment. The 19 paired patient samples and the murine PNETs were analyzed on Agilent microarrays. A small number of the VDV genes did not have human probes on the Agilent microarrays and are denoted by NA at the end of the table. In addition, probes for some murine VDV genes were not present on the Agilent platform; for these genes, Log 2Fc is shown from the repeat experiment on the murine Affymetrix array platform and marked with an asterisk*.

Characterization of the genes within this set having differential (decreased) expression revealed enrichment for known endothelial specific genes (Table 3) implicated in blood vessel development (Table 4). In addition, the median fold-change in expression for this gene set was similar to that seen in the pan-vascular markers CD31 and PLVAP, and was also consistent with the extent of MVD decrease as measured by immunohistochemistry of the pan-vascular marker PLVAP (FIGS. 1A and 1C).

Quantitative PCR (qRT-PCR) of whole tumors confirmed the microarray results, verifying that markers specific to: tumor (insulin); epithelial (E-Cad and Epcam); pan-hematopoietic (CD45); or macrophage (CD68) cells are not significantly changed by anti-VEGF treatment. Also confirming microarray data, qRT-PCR showed that while VEGF transcript levels are not significantly changed, multiple known endothelial markers are downregulated by this treatment (FIG. 1D).

Both microarray and qRT-PCR data identified a subset of genes whose downregulation in response to anti-VEGF was more pronounced than other genes in the signature (FIG. 1D), suggesting that some of the signature genes might be more selectively expressed in the vessels that are sensitive to anti-VEGF treatment. In contrast to low- and intermediate-responding genes (FIG. 1D, yellow and red bars, respectively), this set of extra-responsive genes (FIG. 1D, purple bars) include tip-cell markers and, in the context of developmental retinal angiogenesis, known VEGF targets (Toro et al. *Blood*. 116: 4025-4033, 2010; Roberts et al. *Mol Cell Biol*. 24: 10515-10528, 2004; Testori et al. *Blood*. 117: 2735-2744, 2011; Lobov et al. *Blood*. 117: 6728-6737, 2011). Thus, we postulated that these later genes are candidate proximal biomarkers of VEGF pathway inhibitor activity (proxVDV genes), and are likely to be VEGF targets that are more selectively expressed in the VEGF-dependent tumor vasculature. Taken together, these results suggest that VDV gene expression signature reflects at least two related biological processes: (i) direct VEGF downstream signaling inhibition, and (ii) the subsequent loss of vessels that are dependent on VEGF signaling for survival. According to this working hypothesis, VDV endothelial genes are likely to include proximal (proxVDV) as well as more distal (dist-VDV) downstream surrogate markers of VEGF signaling inhibition in tumor-associated endothelial cells.

TABLE 3

Genes in the VDV signature, ordered by extent of anti-VEGF response in human IBC trial.

| Human Inflammatory Breast Cancer | | | Murine Pancreatic Neuroendocrine Tumors | | |
|---|---|---|---|---|---|
| Entrezgene | Symbol | Log2FC | Entrezgene | Symbol | Log2FC |
| 11082 | ESM1 | −1.928 | 71690 | Esm1 | −3.625 |
| 25780 | RASGRP3 | −1.278 | 240168 | Rasgrp3 | −1.777 |
| 10060 | ABCC9 | −1.229 | 20928 | Abcc9 | −1.232 |
| 3910 | LAMA4 | −1.219 | 16775 | Lama4 | −2.712 |
| 22795 | NID2 | −1.094 | 18074 | Nid2 | −3.818 |
| 4162 | MCAM | −1.005 | 84004 | Mcam | −1.731 |
| 8828 | NRP2 | −0.897 | 18187 | Nrp2 | −1.842 |
| 7127 | TNFAIP2 | −0.854 | 21928 | Tnfaip2 | −0.367 |
| 6678 | SPARC | −0.843 | 20692 | Sparc | −1.746 |
| 27253 | PCDH17 | −0.829 | 219228 | Pcdh17 | −1.909 |
| 23743 | BHMT2 | −0.808 | 64918 | Bhmt2 | −0.163 |
| 51313 | FAM198B | −0.794 | 68659 | Fam198b | −0.26 |
| 9444 | QKI | −0.763 | 19317 | Qk | −0.652 |
| 1306 | COL15A1 | −0.736 | 12819 | Col15a1 | −2.274 |
| 23627 | PRND | −0.732 | 26434 | Prnd | −2.48 |
| 6772 | STAT1 | −0.709 | 20846 | Stat1 | −0.227 |
| 8829 | NRP1 | −0.707 | 18186 | Nrp1 | −1.434 |
| 2200 | FBN1 | −0.701 | 14118 | Fbn1 | −1.139 |
| 28984 | C13orf15 | −0.698 | 66214 | 1190002H23Rik | −2.238 |
| 285 | ANGPT2 | −0.685 | 11601 | Angpt2 | −0.85 |
| 419 | ART3 | −0.675 | 109979 | Art3 | −0.643 |

TABLE 3-continued

Genes in the VDV signature, ordered by extent of anti-VEGF response in human IBC trial.

| Human Inflammatory Breast Cancer | | | Murine Pancreatic Neuroendocrine Tumors | | |
|---|---|---|---|---|---|
| Entrezgene | Symbol | Log2FC | Entrezgene | Symbol | Log2FC |
| 85480 | TSLP | −0.646 | 53603 | Tslp | 0.108 |
| 4208 | MEF2C | −0.644 | 17260 | Mef2c | −1.316 |
| 10008 | KCNE3 | −0.643 | 57442 | Kcne3 | −1.938 |
| 10395 | DLC1 | −0.64 | 50768 | Dlc1 | −0.745* |
| 22918 | CD93 | −0.636 | 17064 | Cd93 | −2.406 |
| 25937 | WWTR1 | −0.631 | 97064 | Wwtr1 | −1.261 |
| 1848 | DUSP6 | −0.614 | 67603 | Dusp6 | −1.427 |
| 6649 | SOD3 | −0.578 | 20657 | Sod3 | 0.144 |
| 4005 | LMO2 | −0.572 | 16909 | Lmo2 | −0.057 |
| 29969 | MDFIC | −0.569 | 16543 | Mdfic | −0.183 |
| 51088 | KLHL5 | −0.557 | 71778 | Klhl5 | −0.489* |
| 83595 | SOX7 | −0.553 | 20680 | Sox7 | −0.765* |
| 5414 | SEPT4 | −0.531 | 18952 | Sept4 | −0.814 |
| 55917 | CTTNBP2NL | −0.531 | 80281 | Cttnbp2nl | −0.501 |
| 1282 | COL4A1 | −0.501 | 12826 | Col4a1 | −1.998 |
| 301 | ANXA1 | −0.5 | 16952 | Anxa1 | −1.31 |
| 1284 | COL4A2 | −0.499 | 12827 | Col4a2 | −1.742 |
| 7431 | VIM | −0.493 | 22352 | Vim | −1.321 |
| 8613 | PPAP2B | −0.488 | 67916 | Ppap2b | −2.638 |
| 112464 | PRKCDBP | −0.487 | 109042 | Prkcdbp | −1.395 |
| 1009 | CDH11 | −0.487 | 12552 | Cdh11 | −1.326 |
| 1295 | COL8A1 | −0.483 | 12837 | Col8a1 | −1.433 |
| 23493 | HEY2 | −0.481 | 15214 | Hey2 | −0.327 |
| 10186 | LHFP | −0.467 | 108927 | Lhfp | −0.481 |
| 2331 | FMOD | −0.462 | 14264 | Fmod | 0.007 |
| 7057 | THBS1 | −0.46 | 21825 | Thbs1 | −0.743 |
| 659 | BMPR2 | −0.442 | 12168 | Bmpr2 | −0.346* |
| 10544 | PROCR | −0.441 | 19124 | Procr | −0.743 |
| 7070 | THY1 | −0.435 | 21838 | Thy1 | −0.757 |
| 5027 | P2RX7 | −0.431 | 18439 | P2rx7 | −0.227 |
| 5159 | PDGFRB | −0.43 | 18596 | Pdgfrb | −1.35 |
| 871 | SERPINH1 | −0.419 | 12406 | Serpinh1 | −2.022 |
| 8490 | RGS5 | −0.419 | 19737 | Rgs5 | −1.002 |
| 54510 | PCDH18 | −0.418 | 73173 | Pcdh18 | −0.074 |
| 5787 | PTPRB | −0.409 | 19263 | Ptprb | −2.028 |
| 857 | CAV1 | −0.404 | 12389 | Cav1 | −0.826 |
| 54538 | ROBO4 | −0.386 | 74144 | Robo4 | −1.605 |
| 8611 | PPAP2A | −0.385 | 19012 | Ppap2a | −0.933 |
| 10791 | VAMP5 | −0.378 | 53620 | Vamp5 | −0.815 |
| 5552 | SRGN | −0.378 | 19073 | Srgn | −0.902 |
| 162073 | ITPRIPL2 | −0.378 | 319622 | Itpripl2 | −0.707* |
| 51294 | PCDH12 | −0.362 | 53601 | Pcdh12 | −1.515 |
| 4781 | NFIB | −0.362 | 18028 | Nfib | −0.945 |
| 716 | C1S | −0.357 | 50908 | C1s | −0.122 |
| 595 | CCND1 | −0.355 | 12443 | Ccnd1 | −1.116 |
| 1464 | CSPG4 | −0.355 | 121021 | Cspg4 | −1.713 |
| 54922 | RASIP1 | −0.348 | 69903 | Rasip1 | −1.423 |
| 3384 | ICAM2 | −0.347 | 15896 | Icam2 | −2.346 |
| 80781 | COL18A1 | −0.342 | 12822 | Col18a1 | −1.659 |
| 2828 | GPR4 | −0.341 | 319197 | Gpr4 | −0.14 |
| 2313 | FLI1 | −0.334 | 14247 | Fli1 | −1.218 |
| 57381 | RHOJ | −0.33 | 80837 | Rhoj | −1.463 |
| 79890 | RIN3 | −0.329 | 217835 | Rin3 | −0.137 |
| 51705 | EMCN | −0.328 | 59308 | Emcn | −2.347 |
| 11167 | FSTL1 | −0.324 | 14314 | Fstl1 | −1.146 |
| 79689 | STEAP4 | −0.321 | 117167 | Steap4 | 0.26 |
| 3200 | HOXA3 | −0.319 | 15400 | Hoxa3 | 0.271 |
| 25925 | ZNF521 | −0.319 | 225207 | Zfp521 | −0.482 |
| 5797 | PTPRM | −0.308 | 19274 | Ptprm | −0.479 |
| 8642 | DCHS1 | −0.301 | 233651 | Dchs1 | −0.367* |
| 29015 | SLC43A3 | −0.301 | 58207 | Slc43a3 | −0.647 |
| 116362 | RBP7 | −0.299 | 63954 | Rbp7 | −2.883 |
| 1404 | HAPLN1 | −0.294 | 12950 | Hapln1 | 0.2 |
| 1490 | CTGF | −0.286 | 14219 | Ctgf | −2.002 |
| 5937 | RBMS1 | −0.282 | 56878 | Rbms1 | −0.663 |
| 158326 | FREM1 | −0.281 | 329872 | Frem1 | −0.307* |
| 56892 | C8orf4 | −0.279 | 69068 | 1810011O10Rik | −2.026 |
| 161198 | CLEC14A | −0.273 | 66864 | Clec14a | −0.563 |
| 10769 | PLK2 | −0.27 | 20620 | Plk2 | −1.322 |
| 51751 | HIGD1B | −0.264 | 75689 | Higd1b | −0.913 |
| 8038 | ADAM12 | −0.264 | 11489 | Adam12 | 0.019 |
| 55901 | THSD1 | −0.261 | 56229 | Thsd1 | −1.379 |
| 51162 | EGFL7 | −0.259 | 353156 | Egfl7 | −0.934 |
| 25960 | GPR124 | −0.248 | 78560 | Gpr124 | −0.78 |

TABLE 3-continued

Genes in the VDV signature, ordered by extent of anti-VEGF response in human IBC trial.

| Human Inflammatory Breast Cancer | | | Murine Pancreatic Neuroendocrine Tumors | | |
|---|---|---|---|---|---|
| Entrezgene | Symbol | Log2FC | Entrezgene | Symbol | Log2FC |
| 26524 | LATS2 | −0.247 | 50523 | Lats2 | −0.33 |
| 90952 | ESAM | −0.244 | 69524 | Esam | −1.027 |
| 1265 | CNN2 | −0.243 | 12798 | Cnn2 | −0.726 |
| 51676 | ASB2 | −0.243 | 65256 | Asb2 | −0.012 |
| 10536 | LEPREL2 | −0.242 | 14789 | Leprel2 | −0.925 |
| 2022 | ENG | −0.235 | 13805 | Eng | −2.167 |
| 28951 | TRIB2 | −0.235 | 217410 | Trib2 | −0.782* |
| 64411 | ARAP3 | −0.232 | 106952 | Arap3 | −2.098 |
| 196 | AHR | −0.228 | 11622 | Ahr | −0.693 |
| 10003 | NAALAD2 | −0.227 | 72560 | Naalad2 | −0.356 |
| 256949 | KANK3 | −0.226 | 80880 | Kank3 | −0.888 |
| 81848 | SPRY4 | −0.225 | 24066 | Spry4 | −1.589 |
| 2122 | MECOM | −0.223 | 14013 | Mecom | −0.175 |
| 51363 | CHST15 | −0.221 | 77590 | Chst15 | −0.101 |
| 6623 | SNCG | −0.215 | 20618 | Sncg | −0.7 |
| 4071 | TM4SF1 | −0.215 | 17112 | Tm4sf1 | −0.752 |
| 116159 | CYYR1 | −0.211 | 224405 | Cyyr1 | 0.114 |
| 2149 | F2R | −0.21 | 14062 | F2r | −0.815 |
| 79899 | PRR5L | −0.209 | 72446 | Prr5l | −0.617 |
| 84898 | PLXDC2 | −0.209 | 67448 | Plxdc2 | −1.16 |
| 53827 | FXYD5 | −0.206 | 18301 | Fxyd5 | −0.728 |
| 10561 | IFI44 | −0.203 | 99899 | Ifi44 | −1.481 |
| 166336 | PRICKLE2 | −0.203 | 243548 | Prickle2 | −0.003 |
| 80310 | PDGFD | −0.2 | 71785 | Pdgfd | −0.386 |
| 2321 | FLT1 | −0.2 | 14254 | Flt1 | −2.762 |
| 2621 | GAS6 | −0.198 | 14456 | Gas6 | −0.895 |
| 83878 | USHBP1 | −0.191 | 234395 | Ushbp1 | −2.261 |
| 3625 | INHBB | −0.19 | 16324 | Inhbb | −1.283 |
| 677 | ZFP36L1 | −0.187 | 12192 | Zfp36l1 | −1.117 |
| 84632 | AFAP1L2 | −0.186 | 226250 | Afap1l2 | −1.297 |
| 10516 | FBLN5 | −0.186 | 23876 | Fbln5 | −0.457* |
| 23075 | SWAP70 | −0.184 | 20947 | Swap70 | −0.19 |
| 5724 | PTAFR | −0.18 | 19204 | Ptafr | −0.639* |
| 84962 | JUB | −0.178 | 16475 | Jub | −0.318 |
| 92747 | BPIFB1 | −0.175 | 228801 | Bpifb1 | 0.146 |
| 2078 | ERG | −0.163 | 13876 | Erg | −1.816 |
| 27123 | DKK2 | −0.159 | 56811 | Dkk2 | −2.214 |
| 26508 | HEYL | −0.153 | 56198 | Heyl | −0.699 |
| 51267 | CLEC1A | −0.151 | 243653 | Clec1a | −0.636 |
| 5793 | PTPRG | −0.151 | 19270 | Ptprg | −1.015 |
| 10161 | LPAR6 | −0.148 | 67168 | Lpar6 | −0.587 |
| 154810 | AMOTL1 | −0.147 | 75723 | Amotl1 | −0.114 |
| 286753 | TUSC5 | −0.146 | 237858 | Tusc5 | −0.358 |
| 9411 | ARHGAP29 | −0.145 | 214137 | Arhgap29 | −0.42 |
| 6237 | RRAS | −0.143 | 20130 | Rras | −0.164 |
| 57514 | ARHGAP31 | −0.141 | 12549 | Arhgap31 | −0.98 |
| 81792 | ADAMTS12 | −0.139 | 239337 | Adamts12 | −0.352* |
| 947 | CD34 | −0.136 | 12490 | Cd34 | −2.707 |
| 149951 | COMMD7 | −0.135 | 99311 | Commd7 | 0.073 |
| 9509 | ADAMTS2 | −0.13 | 216725 | Adamts2 | −1.263 |
| 7010 | TEK | −0.13 | 21687 | Tek | −0.57 |
| 9369 | NRXN3 | −0.128 | 18191 | Nrxn3 | 0.422 |
| 94 | ACVRL1 | −0.123 | 11482 | Acvrl1 | −0.364 |
| 5978 | REST | −0.123 | 19712 | Rest | −0.851 |
| 64123 | ELTD1 | −0.122 | 170757 | Eltd1 | −1.681 |
| 128077 | LIX1L | −0.12 | 280411 | Lix1l | −0.488* |
| 684 | BST2 | −0.119 | 69550 | Bst2 | −0.637 |
| 3397 | ID1 | −0.113 | 15901 | Id1 | −2.744 |
| 958 | CD40 | −0.109 | 21939 | Cd40 | −0.623* |
| 4811 | NID1 | −0.103 | 18073 | Nid1 | −2.257 |
| 3486 | IGFBP3 | −0.101 | 16009 | Igfbp3 | −1.989 |
| 10345 | TRDN | −0.1 | 76757 | Trdn | −0.338* |
| 114571 | SLC22A9 | −0.099 | 319800 | Slc22a30 | 0.088 |
| 4837 | NNMT | −0.097 | 18113 | Nnmt | −0.29* |
| 57608 | KIAA1462 | −0.091 | 240185 | 9430020K01Rik | −1.869 |
| 9749 | PHACTR2 | −0.09 | 215789 | Phactr2 | −0.597* |
| 7078 | TIMP3 | −0.084 | 21859 | Timp3 | −1.573 |
| 2113 | ETS1 | −0.079 | 23871 | Ets1 | −1.224 |
| 80381 | CD276 | −0.078 | 102657 | Cd276 | −0.282* |
| 30844 | EHD4 | −0.07 | 98878 | Ehd4 | −0.483 |
| 2701 | GJA4 | −0.068 | 14612 | Gja4 | −0.431 |
| 170575 | GIMAP1 | −0.066 | 16205 | Gimap1 | −1.332 |
| 285203 | C3orf64 | −0.06 | 101351 | A130022J15Rik | −0.485 |
| 4240 | MFGE8 | −0.06 | 17304 | Mfge8 | −1.199 |

TABLE 3-continued

Genes in the VDV signature, ordered by extent of anti-VEGF response in human IBC trial.

| Human Inflammatory Breast Cancer | | | Murine Pancreatic Neuroendocrine Tumors | | |
|---|---|---|---|---|---|
| Entrezgene | Symbol | Log2FC | Entrezgene | Symbol | Log2FC |
| 5089 | PBX2 | −0.057 | 18515 | Pbx2 | −0.127 |
| 3234 | HOXD8 | −0.052 | 15437 | Hoxd8 | 0.089 |
| 9647 | PPM1F | −0.052 | 68606 | Ppm1f | −0.385 |
| 474344 | GIMAP6 | −0.052 | 231931 | Gimap6 | −1.191 |
| 83483 | PLVAP | −0.051 | 84094 | Plvap | −0.983 |
| 5155 | PDGFB | −0.05 | 18591 | Pdgfb | −0.884* |
| 55340 | GIMAP5 | −0.049 | 317757 | Gimap5 | −1.194 |
| 7157 | TP53 | −0.045 | 22059 | Trp53 | −0.207* |
| 4061 | LY6E | −0.042 | 17069 | Ly6e | −0.375 |
| 79812 | MMRN2 | −0.04 | 105450 | Mmrn2 | −2.415 |
| 23576 | DDAH1 | −0.031 | 69219 | Ddah1 | −0.14 |
| 153579 | BTNL9 | −0.031 | 237754 | Btnl9 | −0.913 |
| 633 | BGN | −0.029 | 12111 | Bgn | −0.797* |
| 27143 | KIAA1274 | −0.027 | 27355 | X99384 | −0.52 |
| 375387 | LRRC33 | −0.025 | 224109 | Lrrc33 | −0.333 |
| 127733 | UBXN10 | −0.023 | 212190 | Ubxn10 | −0.293* |
| 3820 | KLRB1 | −0.017 | 80782 | Klrb1b | −0.301* |
| 80177 | MYCT1 | −0.015 | 68632 | Myct1 | −1.574 |
| 3791 | KDR | −0.014 | 16542 | Kdr | −1.778 |
| 9862 | MED24 | −0.012 | 23989 | Med24 | −0.242* |
| 8522 | GAS7 | −0.011 | 14457 | Gas7 | −0.122 |
| 56062 | KLHL4 | −0.011 | 237010 | Klhl4 | −0.462 |
| 54345 | SOX18 | −0.008 | 20672 | Sox18 | −1.532 |
| 85363 | TRIM5 | −0.008 | 20128 | Trim30a | −0.837 |
| 285852 | TREML4 | −0.006 | 224840 | Treml4 | −0.134 |
| 9510 | ADAMTS1 | −0.005 | 11504 | Adamts1 | −0.491 |
| 8840 | WISP1 | −0.005 | 22402 | Wisp1 | −0.866 |
| 10411 | RAPGEF3 | −0.004 | 223864 | Rapgef3 | −1.67 |
| 7903 | ST8SIA4 | −0.003 | 20452 | St8sia4 | −0.286 |
| 55303 | GIMAP4 | 0.002 | 107526 | Gimap4 | −1.127 |
| 8824 | CES2 | 0.003 | 234673 | Ces2e | −2.514 |
| 89857 | KLHL6 | 0.009 | 239743 | Klhl6 | −0.442 |
| 10052 | GJC1 | 0.009 | 14615 | Gjc1 | −0.894 |
| 3561 | IL2RG | 0.01 | 16186 | Il2rg | −0.028 |
| 56253 | CRTAM | 0.02 | 54698 | Crtam | −0.022 |
| 5583 | PRKCH | 0.026 | 18755 | Prkch | −0.104 |
| 6300 | MAPK12 | 0.026 | 29857 | Mapk12 | −0.182 |
| 162394 | SLFN5 | 0.029 | 327978 | Slfn5 | −0.515* |
| 1807 | DPYS | 0.029 | 64705 | Dpys | −0.085 |
| 4038 | LRP4 | 0.029 | 228357 | Lrp4 | −1.971 |
| 387601 | SLC22A25 | 0.038 | 319800 | Slc22a30 | 0.088 |
| 3142 | HLX | 0.041 | 15284 | Hlx | −0.189 |
| 6556 | SLC11A1 | 0.044 | 18173 | Slc11a1 | −0.133 |
| 6524 | SLC5A2 | 0.046 | 246787 | Slc5a2 | −0.306* |
| 92162 | TMEM88 | 0.048 | 67020 | Tmem88 | −1.771 |
| 64641 | EBF2 | 0.048 | 13592 | Ebf2 | −0.12 |
| 6405 | SEMA3F | 0.048 | 20350 | Sema3f | −0.581 |
| 9351 | SLC9A3R2 | 0.054 | 65962 | Slc9a3r2 | −0.611 |
| 7022 | TFAP2C | 0.054 | 21420 | Tcfap2c | −0.159 |
| 187 | APLNR | 0.055 | 23796 | Aplnr | −0.024 |
| 7139 | TNNT2 | 0.058 | 21956 | Tnnt2 | −1.175 |
| 55679 | LIMS2 | 0.059 | 225341 | Lims2 | −0.69 |
| 11135 | CDC42EP1 | 0.062 | 104445 | Cdc42ep1 | −1.568 |
| 976 | CD97 | 0.067 | 26364 | Cd97 | −1.036 |
| 121599 | SPIC | 0.07 | 20728 | Spic | −0.668 |
| 23604 | DAPK2 | 0.072 | 13143 | Dapk2 | −1.32 |
| 1903 | S1PR3 | 0.073 | 13610 | S1pr3 | 0.028 |
| 23439 | ATP1B4 | 0.083 | 67821 | Atp1b4 | 0.141 |
| 338339 | CLEC4D | 0.091 | 17474 | Clec4d | −0.149 |
| 9002 | F2RL3 | 0.093 | 14065 | F2rl3 | −0.122 |
| 4846 | NOS3 | 0.112 | 18127 | Nos3 | −0.819 |
| 1901 | S1PR1 | 0.127 | 13609 | S1pr1 | −0.315 |
| 11037 | STON1 | 0.144 | 77057 | Ston1 | −0.387* |
| 50619 | DEF6 | 0.146 | 23853 | Def6 | −0.068 |
| 1003 | CDH5 | 0.149 | 12562 | Cdh5 | −2.001 |
| 55215 | FANCI | 0.15 | 208836 | Fanci | 0.342 |
| 84433 | CARD11 | 0.15 | 108723 | Card11 | −0.205* |
| 8497 | PPFIA4 | 0.155 | 68507 | Ppfia4 | −0.241* |
| 3912 | LAMB1 | 0.181 | 16777 | Lamb1 | −2.313 |
| 5054 | SERPINE1 | 0.194 | 18787 | Serpine1 | −1.055 |
| 286749 | STON1-GTF2A1L | 0.217 | 77057 | Ston1 | −0.387* |
| 1285 | COL4A3 | 0.223 | 12828 | Col4a3 | 0.038 |
| 9771 | RAPGEF5 | 0.269 | 217944 | Rapgef5 | −0.991 |
| 93978 | CLEC6A | NA | 56620 | Clec4n | −0.421 |

TABLE 3-continued

Genes in the VDV signature, ordered by extent of anti-VEGF response in human IBC trial.

| Human Inflammatory Breast Cancer | | | Murine Pancreatic Neuroendocrine Tumors | | |
|---|---|---|---|---|---|
| Entrezgene | Symbol | Log2FC | Entrezgene | Symbol | Log2FC |
| 284040 | CDRT4 | NA | 66338 | Cdrt4 | −0.306 |
| 79652 | TMEM204 | NA | 407831 | Tmem204 | −0.708 |
| 100527949 | GIMAP1-GIMAP5 | NA | 317757 | Gimap5 | −1.194 |
| 7058 | THBS2 | NA | 21826 | Thbs2 | −0.18 |
| 338596 | ST8SIA6 | NA | 241230 | St8sia6 | −0.569 |
| 340527 | NHSL2 | NA | 100042480 | Nhsl2 | 0.383 |
| 8578 | SCARF1 | NA | 380713 | Scarf1 | −1.018 |
| 402569 | KPNA7 | NA | 381686 | Kpna7 | −0.362* |
| 441478 | NRARP | NA | 67122 | Nrarp | −0.218 |
| 60681 | FKBP10 | NA | 14230 | Fkbp10 | −0.893 |

TABLE 4

Gene ontology terms over-represented in VDV signature.

a. Biological Process Ontology

| GOBPID | P value | Odds Ratio | Exp Count | Count | Size | Term |
|---|---|---|---|---|---|---|
| GO:0001568 | 1.659e−30 | 10.57 | 6.785 | 51 | 385 | blood vessel development |
| GO:0072358 | 9.829e−27 | 11.35 | 5.111 | 42 | 307 | cardiovascular system development |
| GO:0032501 | 8.002e−20 | 3.465 | 78.43 | 145 | 4610 | multicellular organismal process |
| GO:0001525 | 6.98e−17 | 9.984 | 3.435 | 27 | 205 | angiogenesis |
| GO:0009653 | 7.513e−14 | 4.884 | 10.34 | 40 | 698 | anatomical structure morphogenesis |
| GO:2000145 | 1.642e−12 | 6.281 | 5.146 | 27 | 292 | regulation of cell motility |
| GO:2000026 | 3.997e−12 | 3.818 | 14.26 | 45 | 809 | regulation of multicellular organismal development |
| GO:0009888 | 5.801e−12 | 3.667 | 15.58 | 47 | 901 | tissue development |
| GO:0023052 | 7.066e−12 | 2.478 | 70.26 | 120 | 3987 | signaling |
| GO:0007166 | 1.25e−10 | 2.676 | 33.91 | 72 | 1924 | cell surface receptor linked signaling pathway |
| GO:0032879 | 1.428e−10 | 3.256 | 17.69 | 48 | 1004 | regulation of localization |
| GO:0007155 | 4.022e−10 | 4.398 | 8.01 | 30 | 486 | cell adhesion |
| GO:0000902 | 6.839e−10 | 3.51 | 13.06 | 39 | 741 | cell morphogenesis |
| GO:0051716 | 1.061e−09 | 2.433 | 52.42 | 92 | 3224 | cellular response to stimulus |
| GO:0022603 | 1.467e−09 | 4.37 | 7.419 | 28 | 421 | regulation of anatomical structure morphogenesis |
| GO:0001570 | 8.696e−09 | 15.27 | 0.8459 | 10 | 48 | vasculogenesis |
| GO:0048869 | 1.529e−08 | 3.118 | 15.44 | 40 | 1031 | cellular developmental process |
| GO:0040013 | 1.842e−08 | 8.857 | 1.745 | 13 | 99 | negative regulation of locomotion |
| GO:0048468 | 1.947e−08 | 2.812 | 19.23 | 46 | 1115 | cell development |
| GO:0048731 | 2.693e−08 | 2.53 | 31.52 | 62 | 2288 | system development |
| GO:0030336 | 3.752e−08 | 9.341 | 1.533 | 12 | 87 | negative regulation of cell migration |
| GO:0042330 | 6.307e−08 | 3.522 | 9.376 | 29 | 532 | taxis |
| GO:0009893 | 1.02e−07 | 2.496 | 24.48 | 52 | 1389 | positive regulation of metabolic process |
| GO:0051271 | 1.021e−07 | 8.436 | 1.674 | 12 | 95 | negative regulation of cellular component movement |
| GO:0044093 | 1.213e−07 | 2.808 | 16.41 | 40 | 931 | positive regulation of molecular function |
| GO:0007411 | 3.51e−07 | 4.087 | 5.78 | 21 | 328 | axon guidance |
| GO:0048812 | 3.608e−07 | 3.374 | 9.023 | 27 | 512 | neuron projection morphogenesis |
| GO:0030182 | 3.819e−07 | 2.824 | 14.52 | 36 | 824 | neuron differentiation |

TABLE 4-continued

Gene ontology terms over-represented in VDV signature.

| GO ID | p-value | Fold | % | Count | Total | Description |
|---|---|---|---|---|---|---|
| GO:0007154 | 5.952e−07 | 2.121 | 47.13 | 78 | 2982 | cell communication |
| GO:0040017 | 6.315e−07 | 5.375 | 3.155 | 15 | 179 | positive regulation of locomotion |
| GO:0016310 | 6.357e−07 | 2.528 | 19.53 | 43 | 1108 | phosphorylation |
| GO:0051272 | 6.783e−07 | 5.342 | 3.172 | 15 | 180 | positive regulation of cellular component movement |
| GO:0042221 | 7.279e−07 | 2.602 | 18.43 | 41 | 1141 | response to chemical stimulus |
| GO:0048667 | 9.499e−07 | 3.275 | 8.9 | 26 | 505 | cell morphogenesis involved in neuron differentiation |
| GO:0050789 | 1.172e−06 | 2.17 | 74.81 | 105 | 5270 | regulation of biological process |
| GO:0032990 | 1.185e−06 | 3.084 | 10.19 | 28 | 578 | cell part morphogenesis |
| GO:0006793 | 1.34e−06 | 2.38 | 22.21 | 46 | 1260 | phosphorus metabolic process |
| GO:0030030 | 1.641e−06 | 2.758 | 13.48 | 33 | 765 | cell projection organization |
| GO:0010646 | 1.784e−06 | 2.444 | 19.6 | 42 | 1112 | regulation of cell communication |
| GO:0009966 | 2.756e−06 | 2.621 | 15.19 | 35 | 923 | regulation of signal transduction |
| GO:0022008 | 3.002e−06 | 2.528 | 16.53 | 37 | 938 | neurogenesis |
| GO:0048870 | 3.186e−06 | 3.659 | 6.098 | 20 | 382 | cell motility |
| GO:0009887 | 4.196e−06 | 2.871 | 10.87 | 28 | 617 | organ morphogenesis |
| GO:0007507 | 4.451e−06 | 3.866 | 5.164 | 18 | 293 | heart development |
| GO:0045446 | 4.495e−06 | 17.35 | 0.4527 | 6 | 26 | endothelial cell differentiation |
| GO:0001569 | 4.818e−06 | 17.13 | 0.4582 | 6 | 26 | patterning of blood vessels |
| GO:0048584 | 4.947e−06 | 2.568 | 14.86 | 34 | 843 | positive regulation of response to stimulus |
| GO:0043549 | 7.131e−06 | 3.048 | 8.724 | 24 | 495 | regulation of kinase activity |
| GO:0045937 | 7.801e−06 | 4.308 | 3.86 | 15 | 219 | positive regulation of phosphate metabolic process |
| GO:0001936 | 1.231e−05 | 8.512 | 1.093 | 8 | 62 | regulation of endothelial cell proliferation |
| GO:0008284 | 1.364e−05 | 3.179 | 7.289 | 21 | 425 | positive regulation of cell proliferation |
| GO:0030198 | 1.997e−05 | 5.91 | 1.898 | 10 | 109 | extracellular matrix organization |
| GO:0008015 | 2.281e−05 | 3.708 | 4.741 | 16 | 269 | blood circulation |
| GO:0009725 | 2.406e−05 | 2.638 | 11.3 | 27 | 641 | response to hormone stimulus |
| GO:0048534 | 2.486e−05 | 3.138 | 6.997 | 20 | 397 | hemopoietic or lymphoid organ development |
| GO:0019220 | 2.551e−05 | 2.954 | 8.206 | 22 | 489 | regulation of phosphate metabolic process |
| GO:0010595 | 2.975e−05 | 11.81 | 0.6168 | 6 | 35 | positive regulation of endothelial cell migration |
| GO:0010810 | 3.38e−05 | 7.291 | 1.251 | 8 | 71 | regulation of cell-substrate adhesion |
| GO:0042698 | 3.434e−05 | 6.244 | 1.621 | 9 | 92 | ovulation cycle |
| GO:0001934 | 3.78e−05 | 4.201 | 3.401 | 13 | 193 | positive regulation of protein phosphorylation |
| GO:0048010 | 4.137e−05 | 11.04 | 0.6521 | 6 | 37 | vascular endothelial growth factor receptor signaling pathway |
| GO:0006950 | 5.219e−05 | 1.815 | 44.18 | 69 | 2507 | response to stress |
| GO:0032101 | 5.353e−05 | 3.606 | 4.547 | 15 | 258 | regulation of response to external stimulus |
| GO:0061041 | 5.373e−05 | 8.175 | 0.9869 | 7 | 56 | regulation of wound healing |
| GO:0032268 | 5.635e−05 | 2.661 | 9.924 | 24 | 594 | regulation of cellular protein metabolic process |
| GO:0001945 | 5.934e−05 | 25.18 | 0.2291 | 4 | 13 | lymph vessel development |
| GO:0007162 | 6.034e−05 | 8.011 | 1.005 | 7 | 57 | negative regulation of cell adhesion |

TABLE 4-continued

Gene ontology terms over-represented in VDV signature.

| GO ID | p-value | col3 | col4 | col5 | col6 | Description |
|---|---|---|---|---|---|---|
| GO:0045766 | 6.761e−05 | 7.853 | 1.022 | 7 | 58 | positive regulation of angiogenesis |
| GO:0008285 | 6.909e−05 | 2.899 | 7.525 | 20 | 427 | negative regulation of cell proliferation |
| GO:0043627 | 6.995e−05 | 4.577 | 2.644 | 11 | 150 | response to estrogen stimulus |
| GO:0050900 | 7.404e−05 | 3.915 | 3.63 | 13 | 206 | leukocyte migration |
| GO:0021700 | 7.715e−05 | 4.973 | 2.221 | 10 | 126 | developmental maturation |
| GO:0001974 | 7.921e−05 | 13.54 | 0.4582 | 5 | 26 | blood vessel remodeling |
| GO:0032835 | 7.921e−05 | 13.54 | 0.4582 | 5 | 26 | glomerulus development |
| GO:0032270 | 8.472e−05 | 2.943 | 7.032 | 19 | 399 | positive regulation of cellular protein metabolic process |
| GO:0035556 | 9.397e−05 | 1.921 | 29.33 | 50 | 1664 | intracellular signal transduction |
| GO:0001932 | 9.729e−05 | 3.013 | 6.515 | 18 | 391 | regulation of protein phosphorylation |
| GO:0042060 | 9.976e−05 | 2.741 | 8.357 | 21 | 492 | wound healing |
| GO:0016337 | 0.0001106 | 3.214 | 5.41 | 16 | 307 | cell-cell adhesion |
| GO:0071363 | 0.0001128 | 5.282 | 1.886 | 9 | 107 | cellular response to growth factor stimulus |
| GO:0010628 | 0.0001161 | 2.276 | 14.47 | 30 | 821 | positive regulation of gene expression |
| GO:0050790 | 0.0001167 | 2.351 | 13.11 | 28 | 783 | regulation of catalytic activity |
| GO:0051093 | 0.0001208 | 7.078 | 1.117 | 7 | 67 | negative regulation of developmental process |
| GO:0045165 | 0.0001249 | 4.267 | 2.82 | 11 | 160 | cell fate commitment |
| GO:0007220 | 0.0001449 | 18.88 | 0.282 | 4 | 16 | Notch receptor processing |
| GO:0051345 | 0.000164 | 2.876 | 6.785 | 18 | 385 | positive regulation of hydrolase activity |
| GO:0018212 | 0.0001647 | 4.503 | 2.432 | 10 | 138 | peptidyl-tyrosine modification |
| GO:0070887 | 0.0001692 | 2.072 | 19.16 | 36 | 1087 | cellular response to chemical stimulus |
| GO:0001886 | 0.0001795 | 42.33 | 0.1234 | 3 | 7 | endothelial cell morphogenesis |
| GO:0001541 | 0.0001858 | 8.144 | 0.8459 | 6 | 48 | ovarian follicle development |
| GO:0010557 | 0.0002096 | 2.164 | 15.68 | 31 | 890 | positive regulation of macromolecule biosynthetic process |
| GO:0043086 | 0.0002104 | 2.728 | 7.543 | 19 | 428 | negative regulation of catalytic activity |
| GO:0030195 | 0.0002225 | 10.52 | 0.564 | 5 | 32 | negative regulation of blood coagulation |
| GO:0034446 | 0.0002369 | 16.18 | 0.3172 | 4 | 18 | substrate adhesion-dependent cell spreading |
| GO:0006897 | 0.0002547 | 3.098 | 5.234 | 15 | 297 | endocytosis |
| GO:0050679 | 0.0002688 | 5.27 | 1.674 | 8 | 95 | positive regulation of epithelial cell proliferation |
| GO:0030168 | 0.0002748 | 3.396 | 4.142 | 13 | 235 | platelet activation |
| GO:0065008 | 0.0002799 | 1.783 | 34.8 | 55 | 2016 | regulation of biological quality |
| GO:0070168 | 0.0002835 | 33.86 | 0.141 | 3 | 8 | negative regulation of biomineral tissue development |
| GO:0051128 | 0.0002838 | 2.469 | 9.684 | 22 | 574 | regulation of cellular component organization |
| GO:0007178 | 0.0002866 | 6.079 | 1.281 | 7 | 75 | transmembrane receptor protein serine/threonine kinase signaling pathway |
| GO:0090101 | 0.0002906 | 7.434 | 0.9164 | 6 | 52 | negative regulation of transmembrane receptor protein serine/threonine kinase signaling pathway |
| GO:0045596 | 0.0002939 | 3.054 | 5.305 | 15 | 301 | negative regulation of cell differentiation |
| GO:0042246 | 0.0002987 | 9.796 | 0.5992 | 5 | 34 | tissue regeneration |

TABLE 4-continued

Gene ontology terms over-represented in VDV signature.

| GO:0002682 | 0.0003018 | 2.271 | 12.44 | 26 | 706 | regulation of immune system process |
|---|---|---|---|---|---|---|
| GO:0070482 | 0.0003078 | 3.56 | 3.648 | 12 | 207 | response to oxygen levels |
| GO:0001300 | 0.0003093 | Inf | 0.03525 | 2 | 2 | chronological cell aging |
| GO:0007521 | 0.0003093 | Inf | 0.03525 | 2 | 2 | muscle cell fate determination |
| GO:0048522 | 0.0003187 | 1.841 | 30.24 | 49 | 1922 | positive regulation of cellular process |
| GO:0050818 | 0.000323 | 7.275 | 0.934 | 6 | 53 | regulation of coagulation |
| GO:0045860 | 0.0003382 | 3.01 | 5.375 | 15 | 305 | positive regulation of protein kinase activity |
| GO:0007599 | 0.0003383 | 2.549 | 8.477 | 20 | 481 | hemostasis |
| GO:0001933 | 0.0003581 | 7.123 | 0.9517 | 6 | 54 | negative regulation of protein phosphorylation |
| GO:0034329 | 0.0003606 | 4.054 | 2.679 | 10 | 152 | cell junction assembly |
| GO:0014706 | 0.0003664 | 3.487 | 3.719 | 12 | 211 | striated muscle tissue development |
| GO:0035239 | 0.0003664 | 3.487 | 3.719 | 12 | 211 | tube morphogenesis |
| GO:0071841 | 0.0003674 | 1.663 | 49.66 | 72 | 2818 | cellular component organization or biogenesis at cellular level |
| GO:0030509 | 0.0003759 | 5.797 | 1.339 | 7 | 76 | BMP signaling pathway |
| GO:0051384 | 0.000388 | 4.418 | 2.221 | 9 | 126 | response to glucocorticoid stimulus |
| GO:0008354 | 0.0004197 | 28.22 | 0.1586 | 3 | 9 | germ cell migration |
| GO:0022617 | 0.0004197 | 28.22 | 0.1586 | 3 | 9 | extracellular matrix disassembly |
| GO:0045601 | 0.0004197 | 28.22 | 0.1586 | 3 | 9 | regulation of endothelial cell differentiation |
| GO:0051918 | 0.0004197 | 28.22 | 0.1586 | 3 | 9 | negative regulation of fibrinolysis |
| GO:0060627 | 0.0004433 | 3.942 | 2.749 | 10 | 156 | regulation of vesicle-mediated transport |
| GO:0009968 | 0.0004471 | 2.717 | 6.742 | 17 | 391 | negative regulation of signal transduction |
| GO:0048732 | 0.0004527 | 3.401 | 3.807 | 12 | 216 | gland development |
| GO:0002009 | 0.0004607 | 3.205 | 4.371 | 13 | 248 | morphogenesis of an epithelium |
| GO:0051130 | 0.0004695 | 2.8 | 6.151 | 16 | 349 | positive regulation of cellular component organization |
| GO:0002576 | 0.0004767 | 5.554 | 1.392 | 7 | 79 | platelet degranulation |
| GO:0002064 | 0.0004815 | 6.702 | 1.005 | 6 | 57 | epithelial cell development |
| GO:0017015 | 0.0004815 | 6.702 | 1.005 | 6 | 57 | regulation of transforming growth factor beta receptor signaling pathway |
| GO:0030855 | 0.0005169 | 4.232 | 2.308 | 9 | 136 | epithelial cell differentiation |
| GO:0009612 | 0.0005305 | 4.723 | 1.85 | 8 | 105 | response to mechanical stimulus |
| GO:0048762 | 0.0005305 | 4.723 | 1.85 | 8 | 105 | mesenchymal cell differentiation |
| GO:0050730 | 0.0005305 | 4.723 | 1.85 | 8 | 105 | regulation of peptidyl-tyrosine phosphorylation |
| GO:0061061 | 0.0005315 | 2.766 | 6.221 | 16 | 353 | muscle structure development |
| GO:0030335 | 0.0005443 | 4.201 | 2.325 | 9 | 135 | positive regulation of cell migration |
| GO:0002274 | 0.000555 | 5.403 | 1.427 | 7 | 81 | myeloid leukocyte activation |
| GO:0001503 | 0.0005782 | 3.302 | 3.912 | 12 | 222 | ossification |
| GO:0006936 | 0.0005782 | 3.302 | 3.912 | 12 | 222 | muscle contraction |
| GO:0048660 | 0.0005806 | 6.448 | 1.04 | 6 | 59 | regulation of smooth muscle cell proliferation |
| GO:0008585 | 0.0005979 | 5.331 | 1.445 | 7 | 82 | female gonad development |
| GO:0014910 | 0.0006398 | 11.92 | 0.4053 | 4 | 23 | regulation of smooth muscle cell migration |

TABLE 4-continued

Gene ontology terms over-represented in VDV signature.

| GO:2000379 | 0.0006398 | 11.92 | 0.4053 | 4 | 23 | positive regulation of reactive oxygen species metabolic process |
| GO:0019538 | 0.0006644 | 1.598 | 56.89 | 79 | 3228 | protein metabolic process |
| GO:0071900 | 0.0006835 | 2.921 | 5.146 | 14 | 292 | regulation of protein serine/threonine kinase activity |
| GO:0051347 | 0.0006995 | 2.793 | 5.763 | 15 | 327 | positive regulation of transferase activity |
| GO:0016044 | 0.0007038 | 2.34 | 9.658 | 21 | 548 | cellular membrane organization |
| GO:0051704 | 0.0007045 | 2.023 | 16.09 | 30 | 913 | multi-organism process |
| GO:0009790 | 0.0007198 | 2.202 | 11.75 | 24 | 667 | embryo development |
| GO:0033002 | 0.0007424 | 5.124 | 1.498 | 7 | 85 | muscle cell proliferation |
| GO:0045944 | 0.0007803 | 2.432 | 8.389 | 19 | 476 | positive regulation of transcription from RNA polymerase II promoter |
| GO:0032496 | 0.0007913 | 3.639 | 2.961 | 10 | 168 | response to lipopolysaccharide |
| GO:0001775 | 0.0007992 | 2.571 | 7.103 | 17 | 419 | cell activation |
| GO:0001953 | 0.0008032 | 21.16 | 0.1939 | 3 | 11 | negative regulation of cell-matrix adhesion |
| GO:0017187 | 0.0008032 | 21.16 | 0.1939 | 3 | 11 | peptidyl-glutamic acid carboxylation |
| GO:0080090 | 0.0008098 | 1.558 | 67.27 | 90 | 3817 | regulation of primary metabolic process |
| GO:0050673 | 0.0008897 | 4.954 | 1.543 | 7 | 90 | epithelial cell proliferation |
| GO:0010757 | 0.0009171 | 112.4 | 0.05287 | 2 | 3 | negative regulation of plasminogen activation |
| GO:0001819 | 0.0009233 | 3.881 | 2.503 | 9 | 142 | positive regulation of cytokine production |
| GO:0031328 | 0.0009347 | 1.962 | 17.13 | 31 | 972 | positive regulation of cellular biosynthetic process |
| GO:0008360 | 0.000975 | 5.79 | 1.146 | 6 | 65 | regulation of cell shape |
| GO:0030099 | 0.0009911 | 3.526 | 3.049 | 10 | 173 | myeloid cell differentiation | b. Cellular Component Ontology

| GOCCID | Pvalue | OddsRatio | ExpCount | Count | Size | Term |
|---|---|---|---|---|---|---|
| GO:0044421 | 6.134e−11 | 6.593 | 3.923 | 22 | 252 | extracellular region part |
| GO:0005581 | 1.2e−08 | 10.43 | 1.384 | 12 | 81 | collagen |
| GO:0005615 | 6.927e−08 | 3.082 | 12.87 | 35 | 753 | extracellular space |
| GO:0005886 | 2.337e−07 | 2.486 | 24.72 | 51 | 1707 | plasma membrane |
| GO:0044459 | 3.383e−07 | 2.294 | 28.98 | 57 | 1748 | plasma membrane part |
| GO:0005604 | 3.837e−07 | 11.44 | 0.9494 | 9 | 57 | basement membrane |
| GO:0030141 | 7.723e−06 | 4.297 | 3.846 | 15 | 225 | stored secretory granule |
| GO:0005887 | 1.712e−05 | 2.235 | 19.92 | 40 | 1174 | integral to plasma membrane |
| GO:0005796 | 5.637e−05 | 14.64 | 0.4273 | 5 | 25 | Golgi lumen |
| GO:0009897 | 6.485e−05 | 5.071 | 2.171 | 10 | 127 | external side of plasma membrane |
| GO:0005587 | 9.504e−05 | 58.16 | 0.1026 | 3 | 6 | collagen type IV |
| GO:0031093 | 0.0001243 | 8.805 | 0.7862 | 6 | 46 | platelet alpha granule lumen |
| GO:0005605 | 0.0001291 | 19.45 | 0.2735 | 4 | 16 | basal lamina |
| GO:0005606 | 0.0001642 | 43.62 | 0.1196 | 3 | 7 | laminin-1 complex |
| GO:0060205 | 0.0001778 | 8.189 | 0.8375 | 6 | 49 | cytoplasmic membrane-bounded vesicle lumen |

TABLE 4-continued

Gene ontology terms over-represented in VDV signature.

| GO:0045121 | 0.0004315 | 3.947 | 2.735 | 10 | 160 | membrane raft |
| GO:0005788 | 0.0005969 | 4.621 | 1.88 | 8 | 110 | endoplasmic reticulum lumen |
| GO:0005912 | 0.0006938 | 3.697 | 2.906 | 10 | 170 | adherens junction |
| GO:0043259 | 0.0008633 | 115.9 | 0.05128 | 2 | 3 | laminin-10 complex |
| GO:0070022 | 0.0008633 | 115.9 | 0.05128 | 2 | 3 | transforming growth factor beta receptor complex |
| GO:0005578 | 0.0009301 | 3.548 | 3.018 | 10 | 191 | proteinaceous extracellular matrix | c. Molecular Function Ontology

| GOMFID | Pvalue | OddsRatio | ExpCount | Count | Size | Term |
|---|---|---|---|---|---|---|
| GO:0005201 | 4.706e−11 | 13.3 | 1.329 | 14 | 80 | extracellular matrix structural constituent |
| GO:0005021 | 5.369e−10 | 182.3 | 0.1329 | 6 | 8 | vascular endothelial growth factor-activated receptor activity |
| GO:0005509 | 1.059e−08 | 3.583 | 10.28 | 32 | 619 | calcium ion binding |
| GO:0005178 | 3.02e−08 | 10.98 | 1.213 | 11 | 73 | integrin binding |
| GO:0019199 | 1.52e−07 | 9.187 | 1.412 | 11 | 85 | transmembrane receptor protein kinase activity |
| GO:0050431 | 5.162e−07 | 50.39 | 0.1827 | 5 | 11 | transforming growth factor beta binding |
| GO:0060089 | 2.742e−06 | 2.354 | 21.36 | 44 | 1286 | molecular transducer activity |
| GO:0005518 | 8.458e−06 | 11.21 | 0.7476 | 7 | 45 | collagen binding |
| GO:0038023 | 6.846e−05 | 2.287 | 15.45 | 32 | 930 | signaling receptor activity |
| GO:0017154 | 8.724e−05 | 59.96 | 0.09968 | 3 | 6 | semaphorin receptor activity |
| GO:0005024 | 0.000149 | 18.52 | 0.2824 | 4 | 17 | transforming growth factor beta-activated receptor activity |
| GO:0008289 | 0.0001585 | 2.793 | 7.376 | 19 | 444 | lipid binding |
| GO:0030246 | 0.0001911 | 2.937 | 6.263 | 17 | 377 | carbohydrate binding |
| GO:0005539 | 0.0002787 | 4.192 | 2.592 | 10 | 156 | glycosaminoglycan binding |
| GO:0019899 | 0.0003593 | 2.176 | 14 | 28 | 843 | enzyme binding |
| GO:0001871 | 0.0005776 | 3.797 | 2.841 | 10 | 171 | pattern binding |
| GO:0005520 | 0.0006073 | 12.03 | 0.3987 | 4 | 24 | insulin-like growth factor binding |
| GO:0048407 | 0.0006767 | 22.48 | 0.1827 | 3 | 11 | platelet-derived growth factor binding |
| GO:0019834 | 0.0008154 | 119.4 | 0.04984 | 2 | 3 | phospholipase A2 inhibitor activity |

Example 3. Vascular Responses to VEGF Signaling Blockade are Conserved Across Multiple Tumor Models VDV Responses to VEGF Signaling Blockade are Stromal Specific and Conserved Across Multiple Tumor Models We sought to determine whether the VDV transcriptional signature identified in the murine late-stage PNET model is also detectable in other tumor models.

Figure 2A:
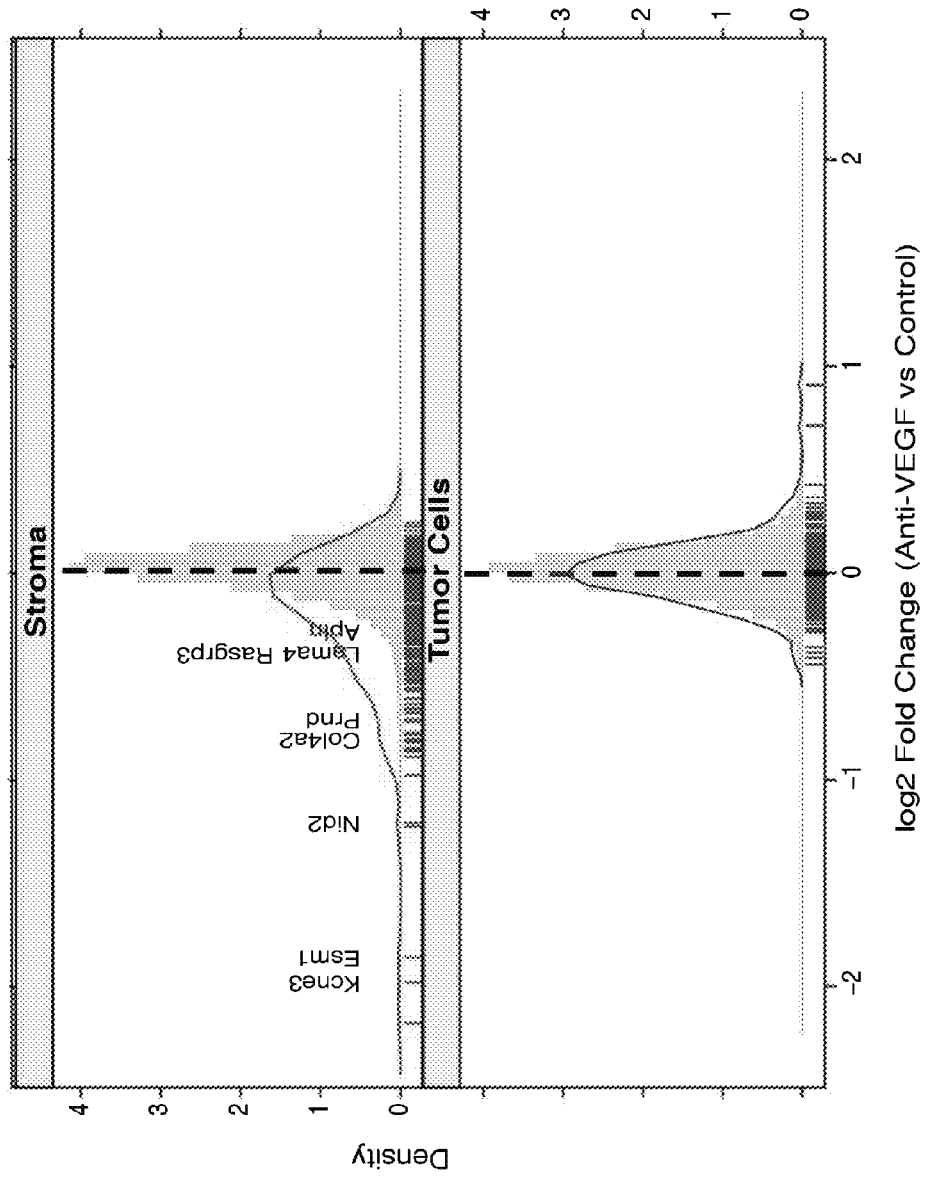
FIG. 2A is a set of graphs showing changes in VDV gene response to VEGF blockade in an established subcutaneous breast carcinoma tumor model (MDA-MB-231). Tumor samples were collected 24 hours after anti-VEGF or control treatment. Genes in the VDV signature (red lines) decrease significantly relative to all genes (shown as a grey histogram) in the stroma (upper graph, mouse chip, p<0.0001), but not in the tumor cells (lower graph, human chip, no significant differences). Individual proxVDV transcript fold-changes are annotated in black letters in the microarray density plot. n=5-10 instances for each treatment cohort.

First, we analyzed whole-tumor responses to anti-VEGF treatment in samples from an established (400 mm$^3$) subcutaneous human breast carcinoma tumor model (MDA-MB-231). While unsupervised expression analysis failed to distinguish between anti-VEGF and control treatment samples, short-term (i.e., 24 hours) anti-VEGF treatment was sufficient to induce a significant downward shift in expression of the vast majority of the VDV genes relative to all other genes (p<0.0001; FIG. 2A, upper panel). Consistent with the hypothesis that VDV genes are endothelial specific, expression changes in these genes were detected only by probes on the murine, but not the human microarrays, corresponding to the distinction between stromal and tumor cells (FIG. 2A). Also, in agreement with the data from the RIP-TβAg GEMM, treatment of the MDA-MB231 subcutaneous xenograft breast cancer tumors with anti-VEGF induced a steeper downregulation of candidate proxVDV gene candidates, relative to pan-vascular markers and other VDV genes.

We found that the effects of long-term anti-VEGF treatment in a third model, an orthotopic, intracranial U87 glioblastoma, resulted also in a pattern of decreased VDV gene expression, with exclusive detection by the mouse-specific probes; and with more marked downregulation of candidate proxVDV genes (FIG. 2B). Comparable VDV patterns of response to anti-VEGF antibody were also consistently observed across multiple anti-VEGF treated human xenograft and murine tumor models tested.

Thus, regardless of the tumor model and implantation site, and independent of the length of antibody treatment, the VDV signature (comprised by proxVDV and distVDV genes) enables consistent detection of gene expression changes that reflect vascular downstream biological consequences of VEGF pathway inhibition in whole tumor mRNA samples.

VEGF Signaling Induces VDV Gene Expression

Next we assessed the extent to which VEGF stimulation could, by reciprocally increasing endothelial VDV gene expression, mark the formation of immature neo-vasculature in two different pathological contexts: wound healing and increased tumor angiogenesis in response to blockade of the Dll4/Notch1 signaling pathway.

In an in vivo mouse skin-wounding assay, topical addition of recombinant VEGF (rVEGF) for 12 hours increased the expression of a majority of VDV genes at the skin wound site, while anti-VEGF treatment had the expected opposite effect (FIG. 2C). Consistent with the response seen in tumors, the effects of VEGF blockade and topical VEGF were most marked in the proxVDV gene candidates.

Figure 2D:
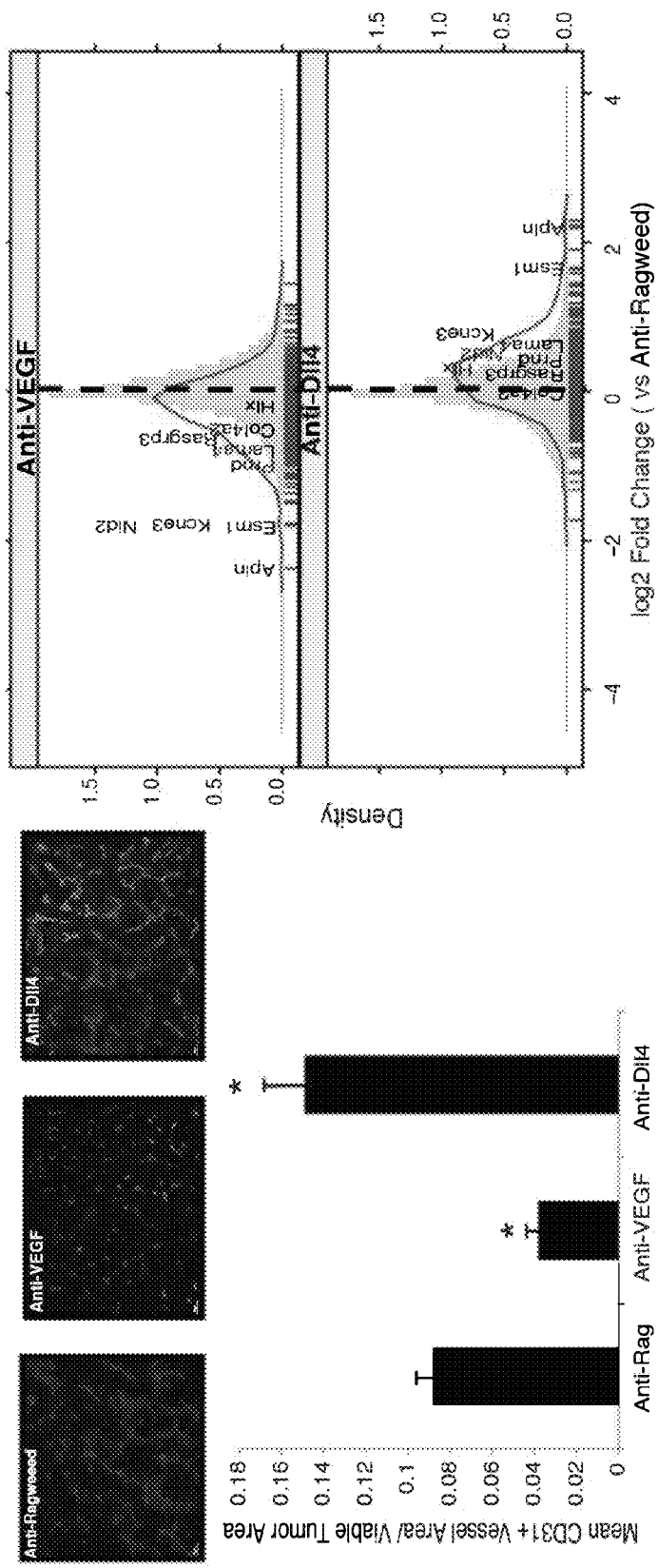
FIG. 2D presents histological data and graphs showing VEGF signaling induces VDV gene expression. In contrast to anti-VEGF downregulation of the VDV gene signature (right, upper graph, p<0.0001), anti-Dll4 treatment causes a upregulation of a majority of VDV genes (right, lower graph, p<0.0001) after 48 hours in an MDA-MB-231 model consistent with hypervascularization evident by immunofluorescent staining for CD31/PECAM as compared to control treatment (left). Individual proxVDV transcript fold-changes are annotated in black letters. n=5-10 instances for each treatment cohort.

The consequences of inducing neo-vascularization through inhibition of the Dll4/Notch1 signaling pathway were assessed by treating MDA-MB-231 tumor bearing mice with anti-Dll4, anti-VEGF, or control anti-ragweed antibody for 48 hours. The Dll4/Notch1 pathway increases nonproductive angiogenesis partly via enhancement of VEGF signaling (Jakobsson et al. *Biochem Soc Trans.* 37: 1233-1236, 2009; Ridgway et al. *Nature.* 444: 1083-1087, 2006; Jakobsson et al. *Nat. Cell Biol.* 12(10): 943-953, 2010). Histological analysis showed that, as expected, anti-VEGF treatment induced vascular pruning of tumor vasculature, while tumors treated with anti-Dll4 showed increased MVD when compared to controls (FIG. 2D, left). The expression of VDV genes changed concordantly, decreasing upon anti-VEGF treatment and increasing in response to blockade of Dll4 (FIG. 2D, right). Again, as seen in other models, the change in expression of the proxVDV gene candidates is more pronounced than of the other VDV genes.

Overall, these data suggest that most VDV genes are expressed in VEGF-driven neo-vasculature, and that their collective expression likely reflects VEGF biological activity as well as the relative abundance of VEGF-dependent vasculature.

Figure 3:
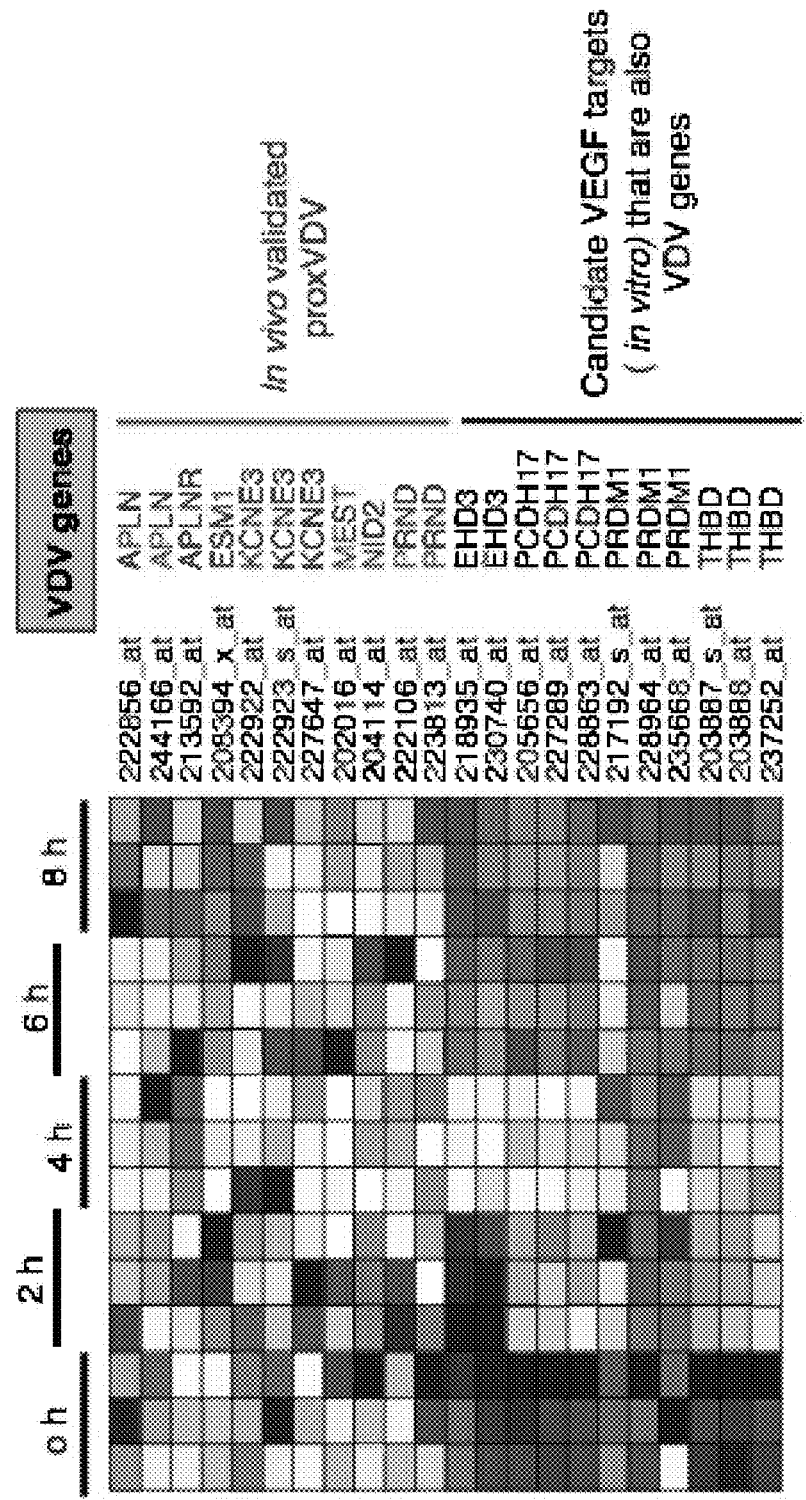
FIG. 3 is a heat map showing that most proxVDV genes are not obviously up-regulated by rVEGF in vitro. Gene expression analyses of rVEGF stimulation of HUVECs. H (hours) indicates length of rVEGF stimulation. The heat map shown here highlights the results of microarray expression analyses for selected VDV probes. Dark blue represents maximal relative down-regulation and dark red the maximal degree of transcript up-regulation. ProxVDV genes are not markedly regulated by rVEGF in vitro. However, a yet uncharacterized small group of VDV genes (EHD3, PCHD17, and THBD) seem to be strongly up-regulated upon rVEGF stimulation of HUVECs. Expression data for each time-point is from three independent replicates.

Of note, the transcriptional effects of VEGF pathway activation have been previously investigated, in both in vitro and in vivo systems. However, the transcriptional consequences of rVEGF stimulation in endothelial cells in vitro does not provide sufficient information to determine if a gene is indeed a bona-fide VEGF in vivo target. Indeed, we have found under many conditions that rVEGF stimulation of HUVECs in vitro does not induce transcription of most of the proxVDV genes we have identified (FIG. 3). This discrepancy should not be surprising, considering the systemic role of the vasculature as an integrator of many stimuli, including blood flow and mechanical forces, and that VEGF responses are dose as well as context dependent.

On the other hand, some of the genes identified here (including ESM1) as well as genes that we did not identify as likely targets (including Pcdh17, EHD3, PRDM1, and THBD among others; see FIG. 3) are reliably upregulated by VEGF stimulation in vitro. Thus, the list of proxVDV genes presented here is unlikely to be comprehensive, and we are currently integrating in vivo and in vitro data-sets in an effort to identify additional in vivo VEGF targets.

Figure 4A:
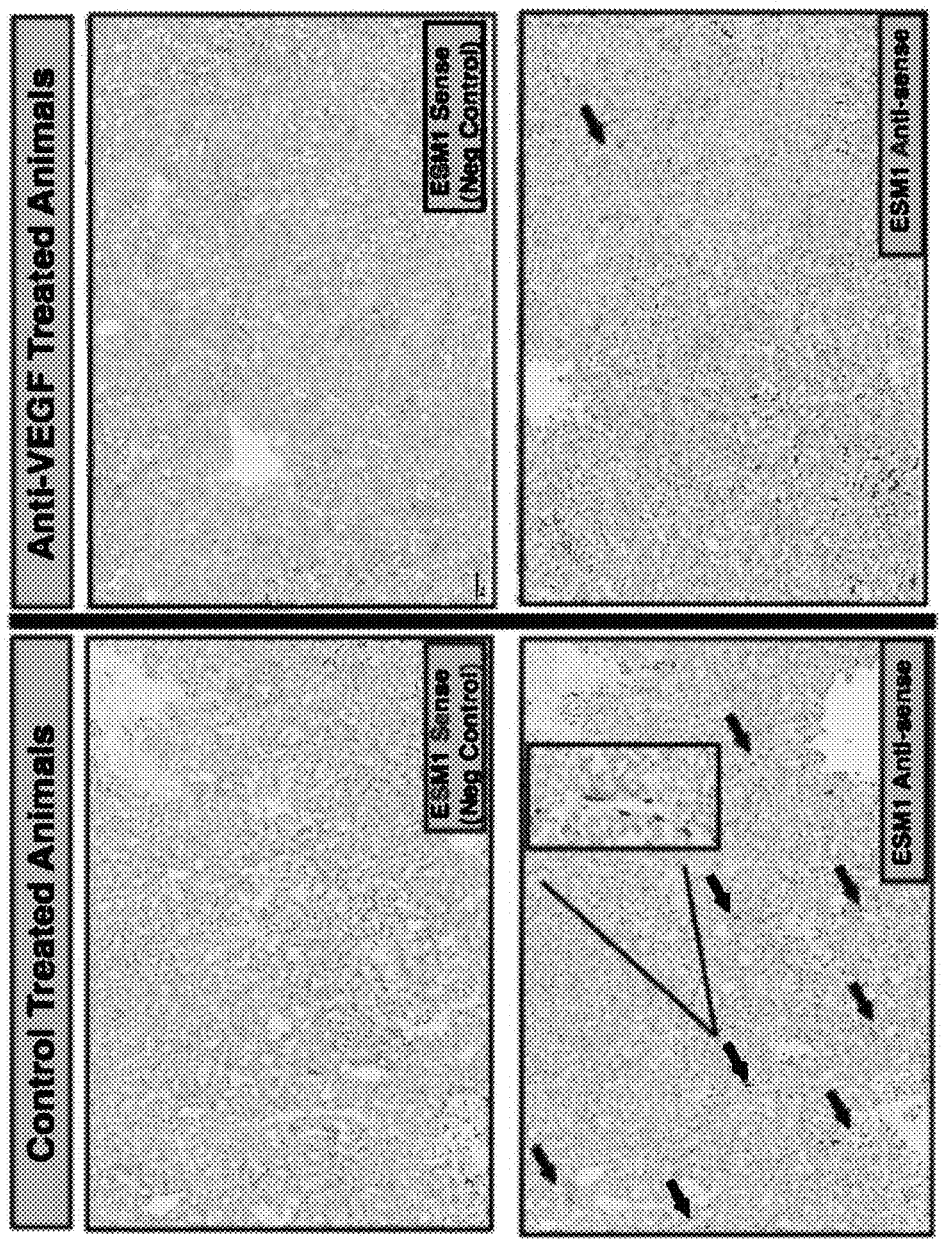
FIG. 4A is a in situ hybridization (ISH) images showing that the proxVDV gene ESM1 is an in vivo VEGF target specifically expressed in tumor-associated vasculature. Top pictures (left and right): ISH negative controls with sense oligos show no significant background (non-specific staining). Bottom pictures show ESM1 mRNA expression (by ISH with anti-sense oligos) in HM7 tumor sections from anti-VEGF or control treated animals. Black arrows indicate several areas of strong ESM1 mRNA vascular expression (brown staining) in control treated tumor slides (bottom picture slide left). In contrast, ESM1 was almost undetectable in tumor slides from anti-VEGF treated animals (bottom picture, right). All slides were also counter stained with Haematoxylin Eosin (H&E).
Figures 4B, 4C:
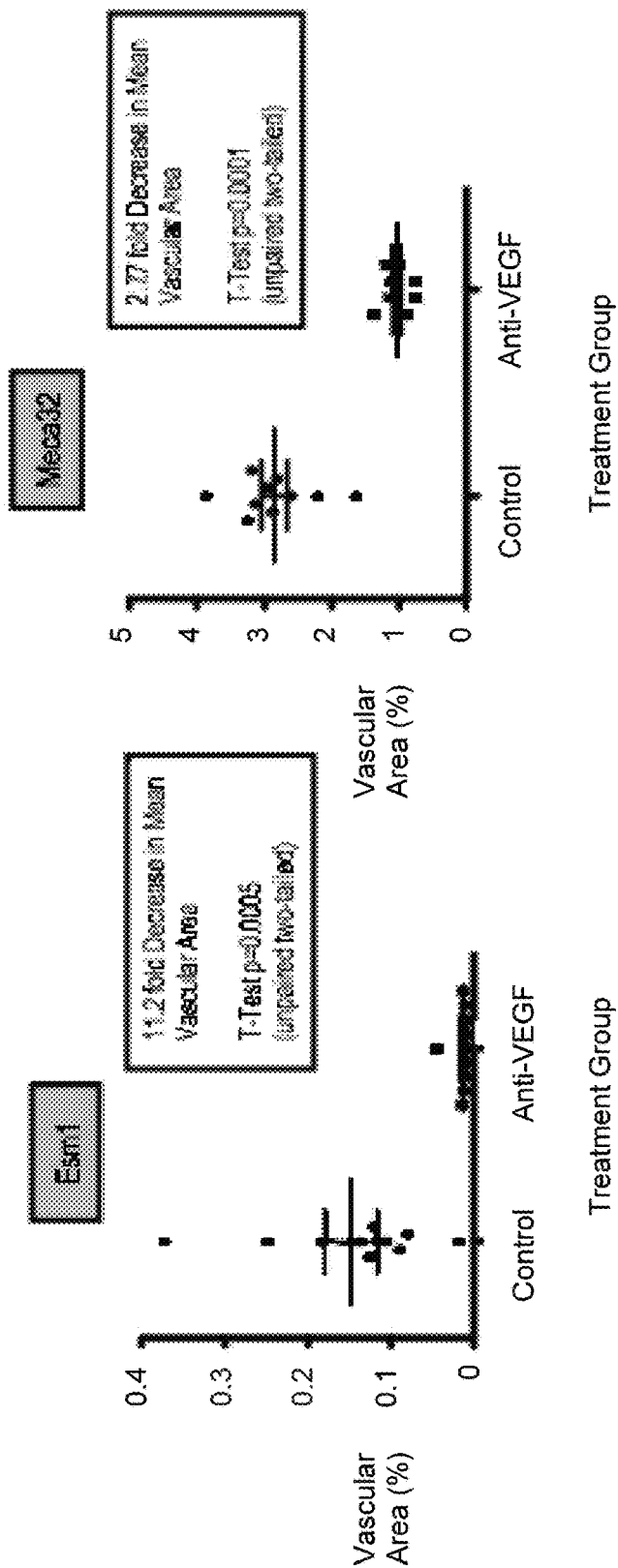
FIG. 4B is a graph showing quantification of ESM1 (ISH) staining in tumor slides from control and anti-VEGF-treated animals. n=10.
FIG. 4C is a graph showing quantification of MECA32 (PLVAP) staining in tumor slides from control and anti-VEGF-treated animals. n=10.
Figure 4D:
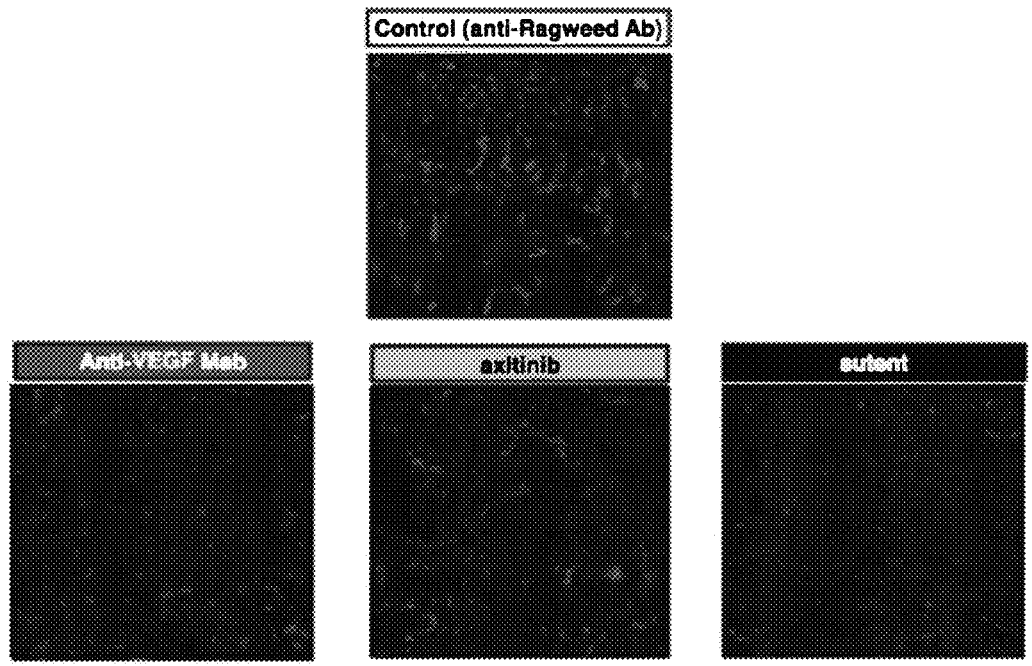
FIG. 4D is a set of histological images and corresponding quantitative graph showing evidence for the in vivo activity of VEGF pathway inhibitors in MDA-MB-231 tumors. Anti-VEGF mAb, sunitinib, or axitinib in vivo treatment efficiently reduces MVD in tumors 72 hour post-treatment. Animals bearing MDA-MB-231 tumors were treated as indicated in materials and methods for 72 hours and then tumors were collected for histological and gene expression analyses. Top images: tumor vessel density via MECA-32 (PLVAP) and CD31 staining (red). Nuclei were counter-stained with DAPI (blue). Images were taken at 20× magnification. Bottom graph shows quantification (as mean+/−SEM) from 8 tumors in each treatment group. *P<0.05.
Figure 4D:
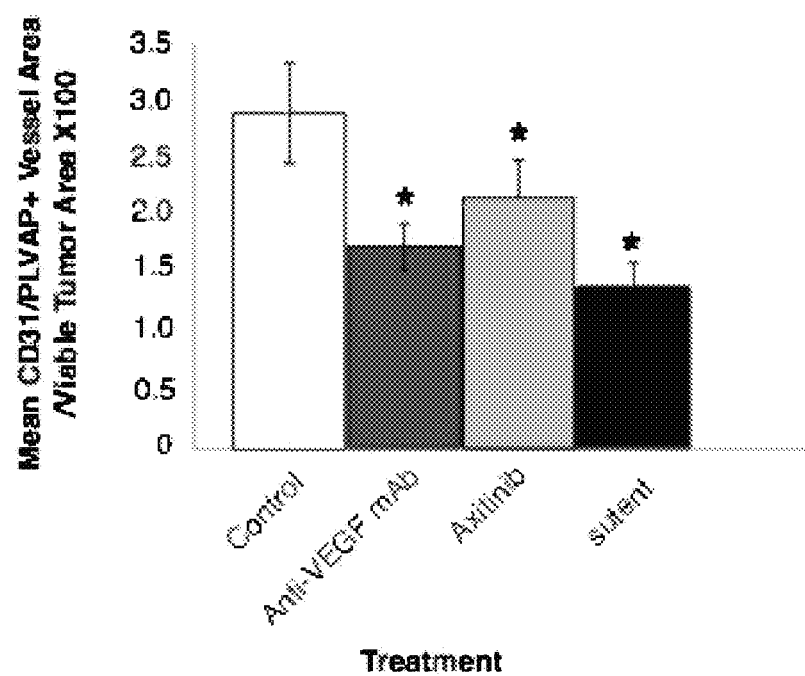
Figure 4E:
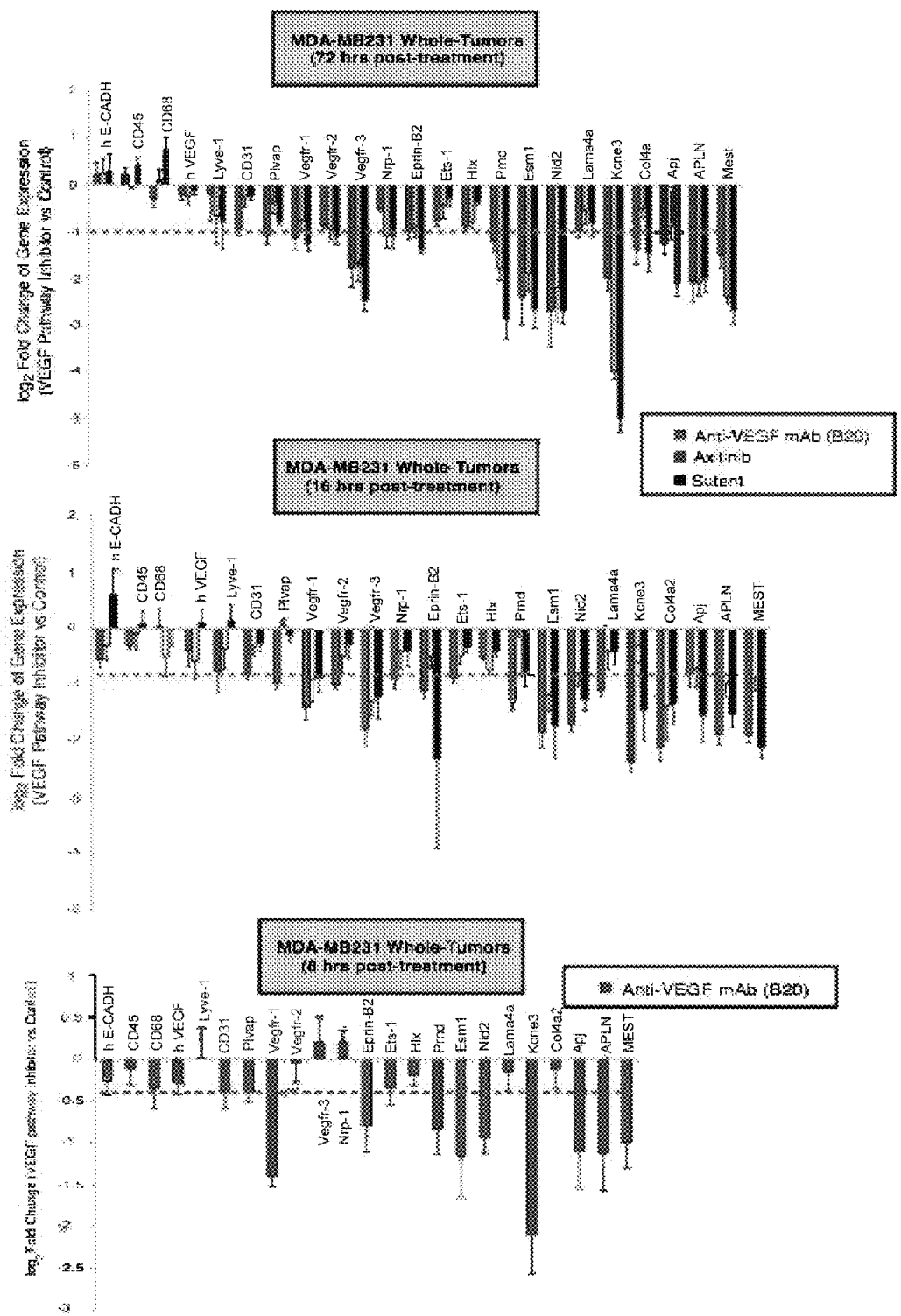
FIG. 4E is a set of graphs showing that in vivo VEGF blockade or VEGFR-2 downstream signaling inhibition induces consistent downregulation of proxVDV genes. qRT-PCR analysis of gene expression in 400 mm³ MDA-MB-231 xenograft tumors collected 8 (bottom panel), 16 (middle panel), or 72 hours (top panel) after treatment with VEGF and VEGFR-2 inhibitors (sunitinib and axitinib). Values represent the mean $\log_2$ fold change in relative gene expression induced by VEGF/VEGFR-2 inhibitor when compared to control treatment mean gene expression. Non-vascular markers such as E-cadh and CD45 do not change significantly in response to these inhibitors. Bottom panel (8 hours post-treatment) shows only anti-VEGF treatment because Axitinib and sunitinib did not have evident activity at this particular time point. Gene expression data represent mean of 8 biological replicates for each treatment. Error bars represent standard deviation.

Example 4. proxVDV Genes are In Vivo Proximal Markers of VEGF/VEGFR-2 Downstream Bioactivity Data from in situ hybridization (ISH) indicated that Esm1 is highly expressed in a significant fraction of vessels from HM7 colon xenograft tumors, while being nearly undetectable in vessels from anti-VEGF treated tumors (FIG. 4A-4C). This is consistent with Esm1 being a bona fide proxVDV gene. However, because ESM1 is regulated by other stimuli besides VEGF (Scherpereel et al. *Crit. Care Med.* 34(2): 532-537, 2006) and since ESM1 may also be occasionally expressed in tumor cells, we wanted to validate additional proxVDV gene candidates as a collective and more specific mean to gauge, in vivo, VEGF downstream signaling bioactivity in response to FDA approved VEGF/VEGFR-2 inhibitors. Thus, in these experiments mice bearing established MDA-MB-231 tumors with treated with a control mAb, anti-VEGF mAb (as a surrogate for bevacizumab), sunitinib (Sutent®; Escudier. *Expert Rev. Anticancer Ther.* 10(3): 305-317, 2010), a small-molecule TKI that targets VEGFR-2 among other RTKs, or with axitinib (Kindler et al. *Lancet Oncol.* 12(3): 256-262, 2011; Grunwald et al. *Onco. Targets Ther.* 5:111-117, 2012), a more specific VEGFR-2 inhibitor. Subsequently, tumors were collected at 8, 16, or 72 hours after treatment for analyses (FIG. 5A, upper panel). Consistent with prior observations, all three inhibitors induced a significant reduction of MVD in tumors collected 72 hours after treatment (FIG. 4D). At the gene expression level, we found that in all cases, the proxVDV genes showed a greater downregulation than that seen for the pan-vascular markers Cd31 and Plvap (FIG. 5A). Importantly, the expression of Vegfa and of the non-vascular markers, E-cad (epithelial) and Cd45 (hematopoietic), was not markedly affected by any of the VEGF pathway inhibitors tested (FIG. 4E), suggesting that the changes in proxVDV gene expression are likely "on-target" and endothelial specific. At 72 hours, sunitinib seems to be the strongest VEGF pathway inhibitor (FIG. 5A).

The dynamics of the transcriptional response differed between small molecule inhibitor and anti-VEGF antibody treatment. No significant changes in gene expression were induced by sunitinib or axitinib after 8 hours of treatment. Only at 16 hours post-treatment were the effects of the two SMIs on downregulating proxVDV gene expression apparent, and this effect increased at 72 hours after treatment (FIG. 5A). In contrast, downregulation of proxVDV (but not distVDV) genes by anti-VEGF mAb (intraperitoneal administration) is obvious at 8 hours after dosing, reaching its peak by 16 hours post treatment.

Figure 5B:
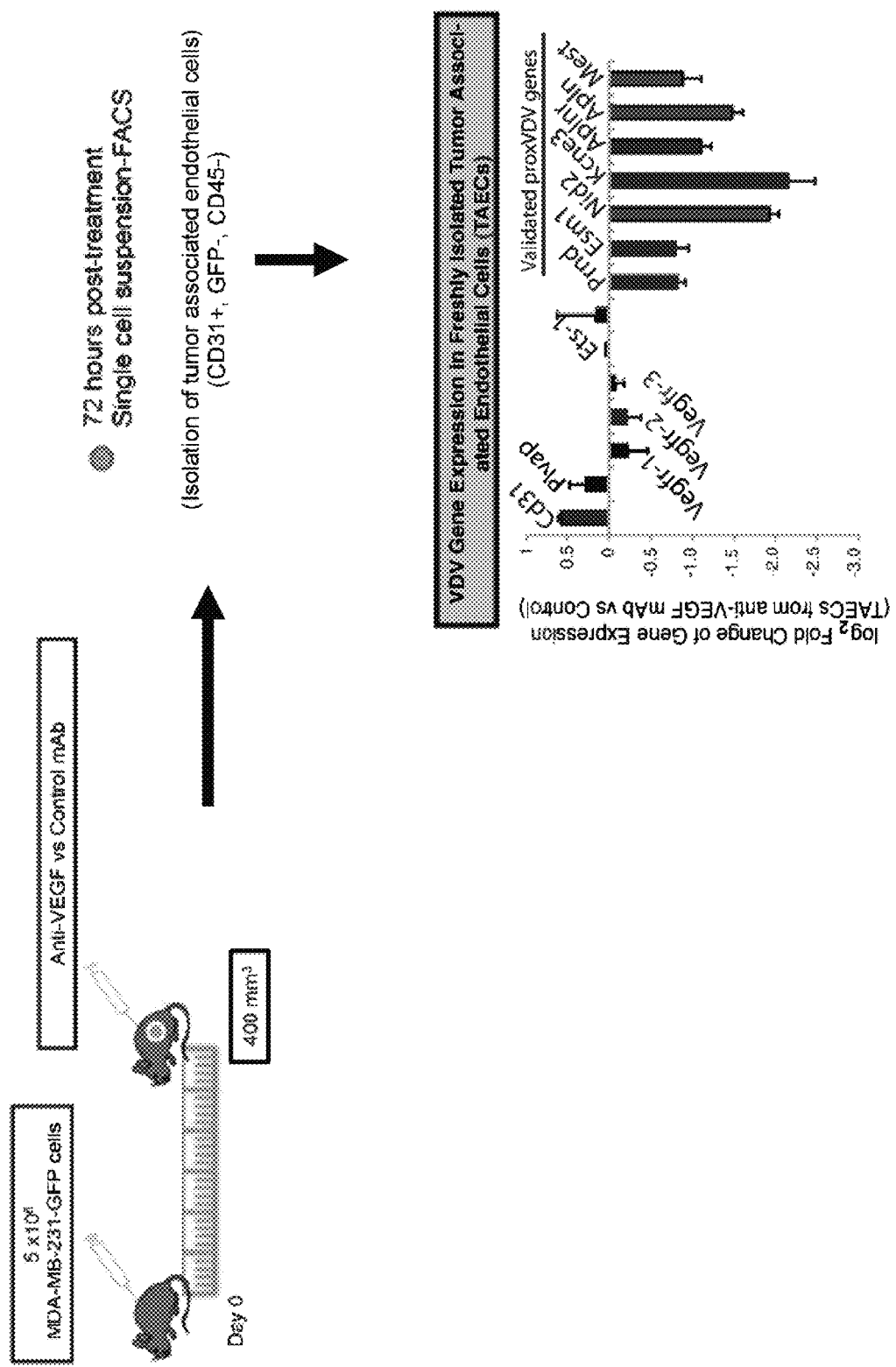
FIG. 5B is a graph showing the quantification of proxVDV gene expression by qRT-PCR in endothelial cells sorted from MDA-MB-231 xenograft tumors treated with ragweed or anti-VEGF mAb. Values represent the mean of the $\log_2$ fold change of 3 replicates. Error bars represent standard deviation.
Figure 6:
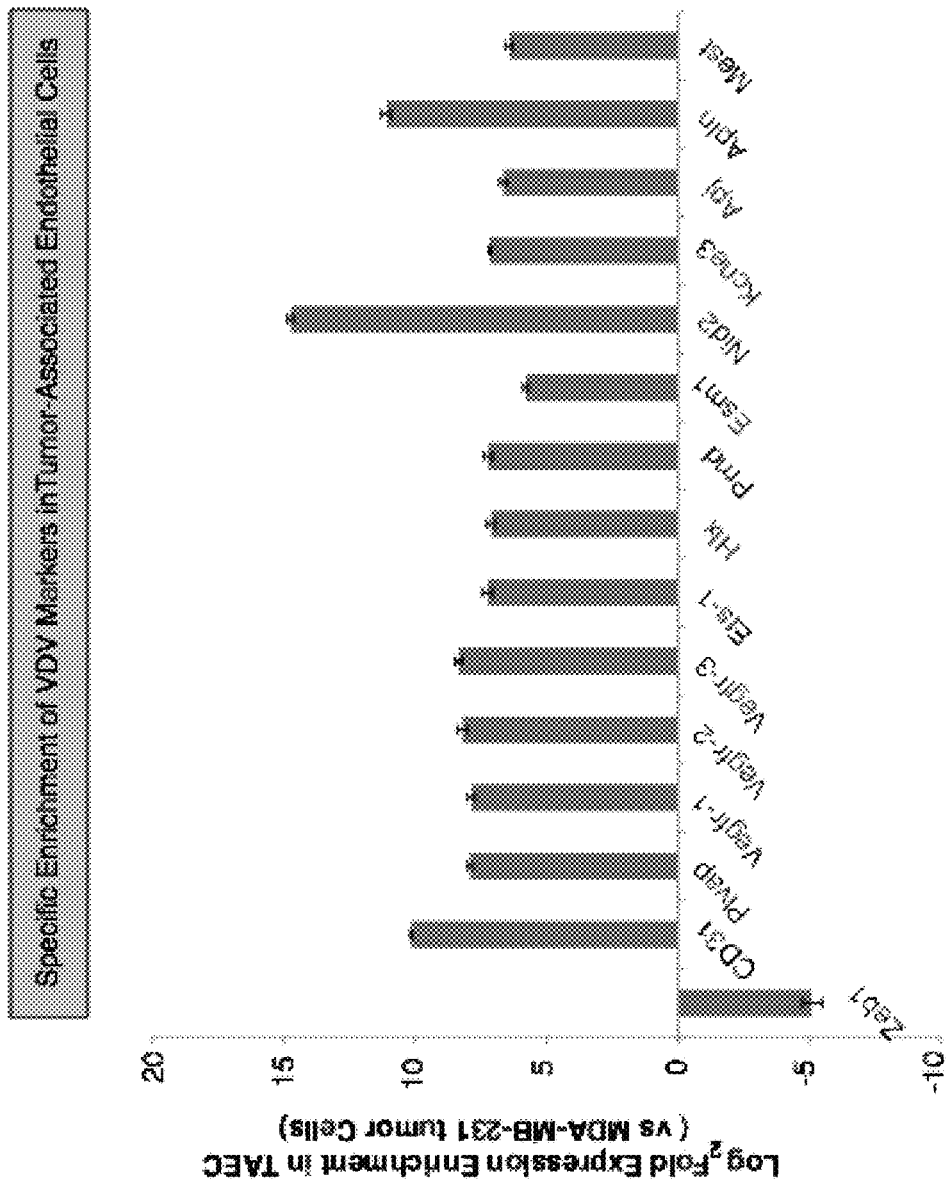
FIG. 6 is a graph showing enrichment of VDV markers in Tumor-Associated Endothelial Cells (TAECs) by ex vivo enrichment expression analyses of VDV transcripts in freshly FACS isolated TAEC versus GFP-MDA-MB-231 tumor cells. Relative gene expression in TAEC versus tumor cells was measured by qRT-PCR of selected genes. All VDV genes tested were highly enriched (25-200 fold) in TAECs. By contrast Zeb1 mRNA expression (an epithelial marker) was decreased in TAECs and enriched in tumor cells. Values represent the mean of the relative $\log_2$ fold gene enrichment when comparing TAECs to tumor cells. TAEC cells were sorted as CD31 positive, CD45 negative, and GFP negative cells. Tumor cells were sorted by GFP positivity. Gene expression data represent the mean of six tumors that were pooled for each FACS sorting experiment. qRTPCR was run in triplicates. Error bars represent standard deviation.

To confirm whether this proxVDV gene set was indeed regulated by VEGF signaling in tumor-associated endothelial cells (TAECs), we treated MDA-MB-231-GFP tumor-bearing animals with anti-VEGF or control antibody, and then isolated TAECs (Cd31+, Cd45−, GFP−) by fluorescence-activated cell sorting (FACS), and compared gene expression ex vivo among the two different treatment groups. We found that all pan-vascular markers and proxVDV genes tested were highly enriched on endothelial cells when compared to other sorted cell populations (FIG. 6). The proxVDV genes Prnd, Esm1, Nid2, Kcne3, Apj, Apln, and Mest were consistently downregulated in TAEC cells isolated from anti-VEGF treated animals relative to controls, while other VDV genes such as Cd31, Plvap, Ets-1 and Hlx were not (FIG. 5B). This data confirms that Prnd, Esm1, Nid2, Kcne3, Apln, Apj, and Mest are proximal and sensitive biomarkers of VEGF bioactivity and are candidate reporters for the direct inhibition of the pathway in tumor-associated endothelial cells in vivo.

Figure 7:
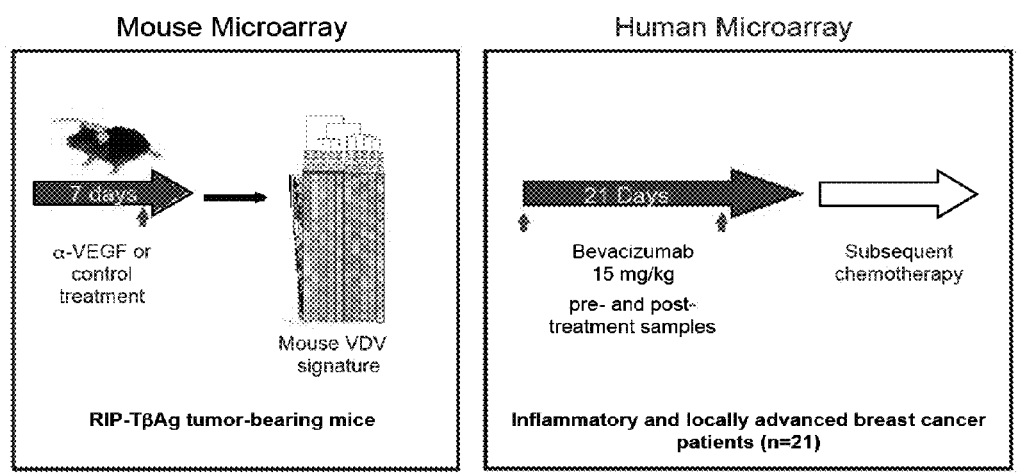
FIG. 7 is a graph showing the change in gene expression (post-vs pre-treatment) in biopsy samples from 19 inflammatory breast cancer patients. Genes in the VDV signature (red lines) decrease significantly relative to all genes (grey histogram), p=0.0275.
Figure 7:
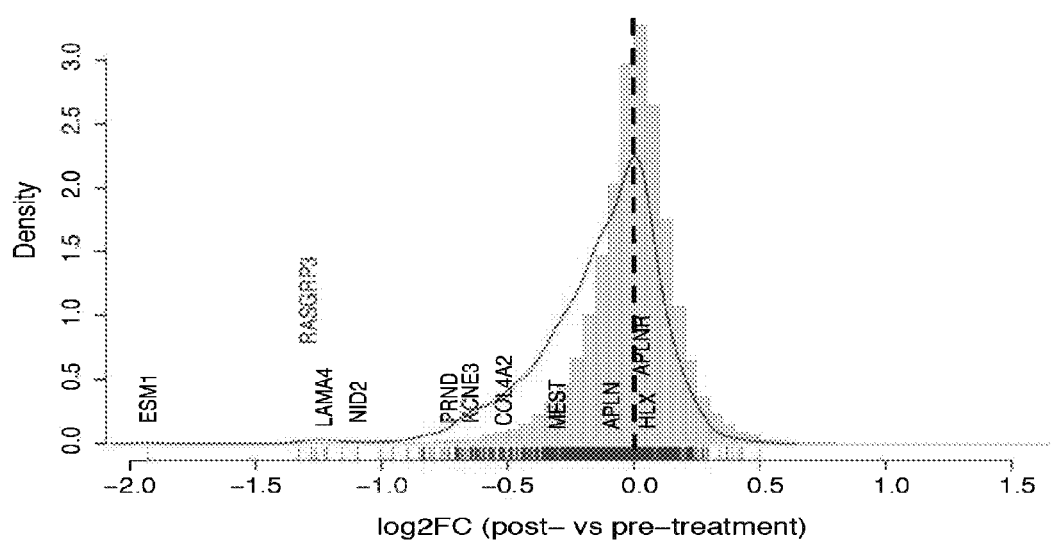

Example 5. Vascular Transcriptional Responses to VEGF Signaling Blockade are Conserved Between Mouse and Human Tumors To test whether the responses to VEGF neutralization we identified in murine models were conserved in human tumor vasculature, we investigated the effect of VEGF blockade on VDV signature expression in tumor biopsies from bevacizumab (Avastin®) treated patients. Here, we took advantage of published micro-array data from matched pre- and 21-days-post-treatment paired biopsies from 19 inflammatory breast cancer patients treated with one dose of bevacizumab as a single agent (Wedam et al. *Journal of Clin. Oncology.* 24: 769-777, 2006). Although conventional bioinformatics analyses had failed to distinguish most specific vascular gene expression changes in response to bevacizumab treatment in these biopsies a priori (Yang et al. *Clin Cancer Res.* 14: 5893-5899, 2008), focused expression analyses of the human orthologues of the VDV gene set showed a clear down regulation of VDV transcripts in post-bevacizumab treatment clinical samples as compared with pre-treatment biopsies (FIG. 7). As in the murine tumor models, we observed that the expression of several proxVDV genes such as ESM1, NID2, PRND, KCNE3, and MEST decreases more markedly upon VEGF treatment. The VDV gene set we identified in preclinical models thus enables the detection of an evolutionary conserved vascular response to VEGF signaling inhibition in clinical tumor samples.

Example 6. Pre-Treatment Expression Levels of VDV Genes in Human Colorectal Cancers Correlate with Clinical Responses to Bevacizumab Our data indicate that human tumor vessels enriched in VDV genes is uniquely responsive to VEGF signaling inhibition. We next tested the hypothesis that the relative enrichment of these markers in pre-treatment tumor samples could actually predict responsiveness to anti-VEGF therapy.

Bevacizumab in combination with chemotherapy has previously been shown to increase progression free survival (PFS) and overall survival (OS) in patients with metastatic colorectal carcinoma (CRC) (Hurwitz et al. *N Engl J Med.* 350: 2335-2342, 2004). NO16966 was a first-line metastatic CRC trial where patients received oxaliplatin-based chemotherapy (XELOX or FOLFOX-4) in combination with either placebo or bevacizumab; the addition of bevacizumab to chemotherapy in this particular study significantly improved the primary endpoint of PFS, albeit the OS differences (a secondary endpoint) did not reach statistical significance (Saltz et al. *Journal of Clin. Oncology.* 26: 2013-2019, 2008). To test if VDV gene expression could correlate with clinical outcomes, we analyzed VDV gene expression levels in available pre-treatment archival tumor tissue from 103 patients (biomarker evaluable subpopulation) that were enrolled in the XELOX-containing arms. Due to the limited quality and amount of RNA from these clinical samples, gene expression was analyzed in a previously designed and validated "angiogenesis" Fluidigm qRT-PCR chip (FIG. 8B) that included 4 different housekeeping genes (for gene expression normalization), VEGF (as a control), and 22 representative proximal and distal VDV genes comprising: (i) pan-vascular markers such as CD31, CD34, and VE-CADH as indicators of MVD; (ii) key VEGF pathway components and proxVDV genes, including VEGFR-1, VEGFR-2, VEGFR-3, EPHRINB2, NRPs, ESM1, NID2, COL4a2, and LAMA4a; and (iii) additional VDV genes that are components of endothelial signaling pathways and potential modulators of VDV biology, including DLL-4, NOTCH1, ALK1, and EGFL7 (see FIG. 9A for validation of this compacted 22 VDV gene signature).

Figure 8A:
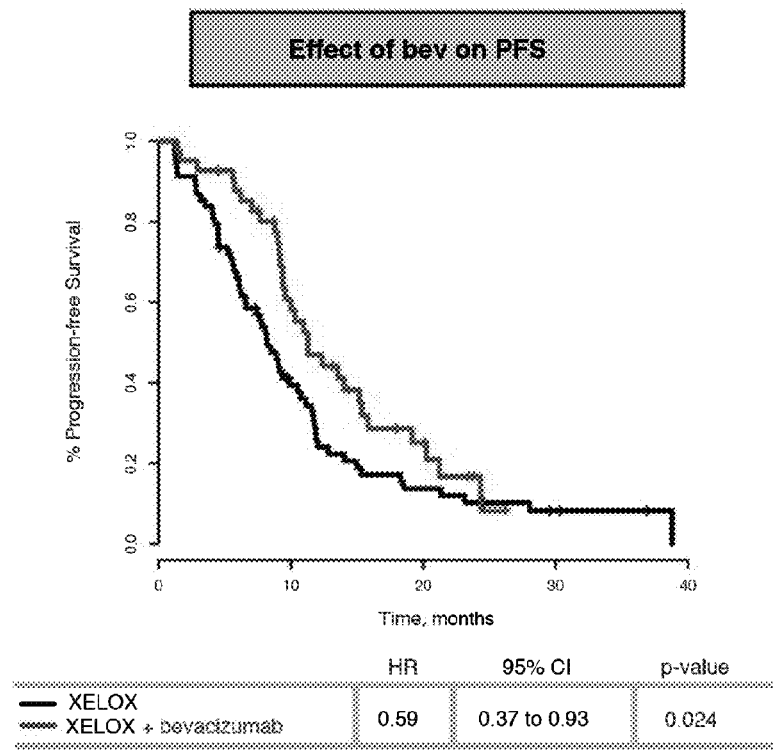
FIG. 8A is a set of graphs showing progression-free (top) and overall survival (bottom) of 103 colorectal cancer patients with available pre-treatment mRNA in the NO16966 trial.
Figure 8A:
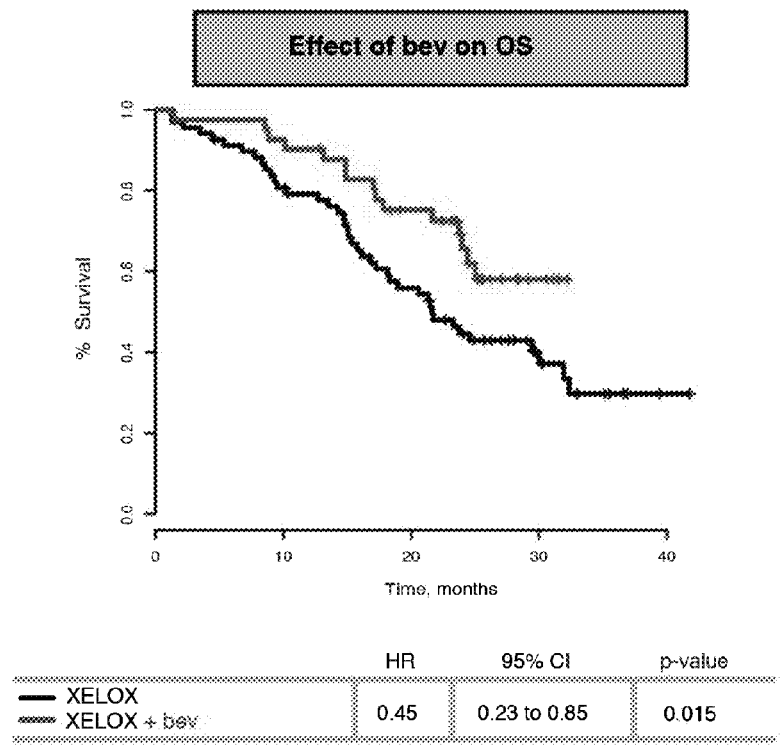
Figure 8B:
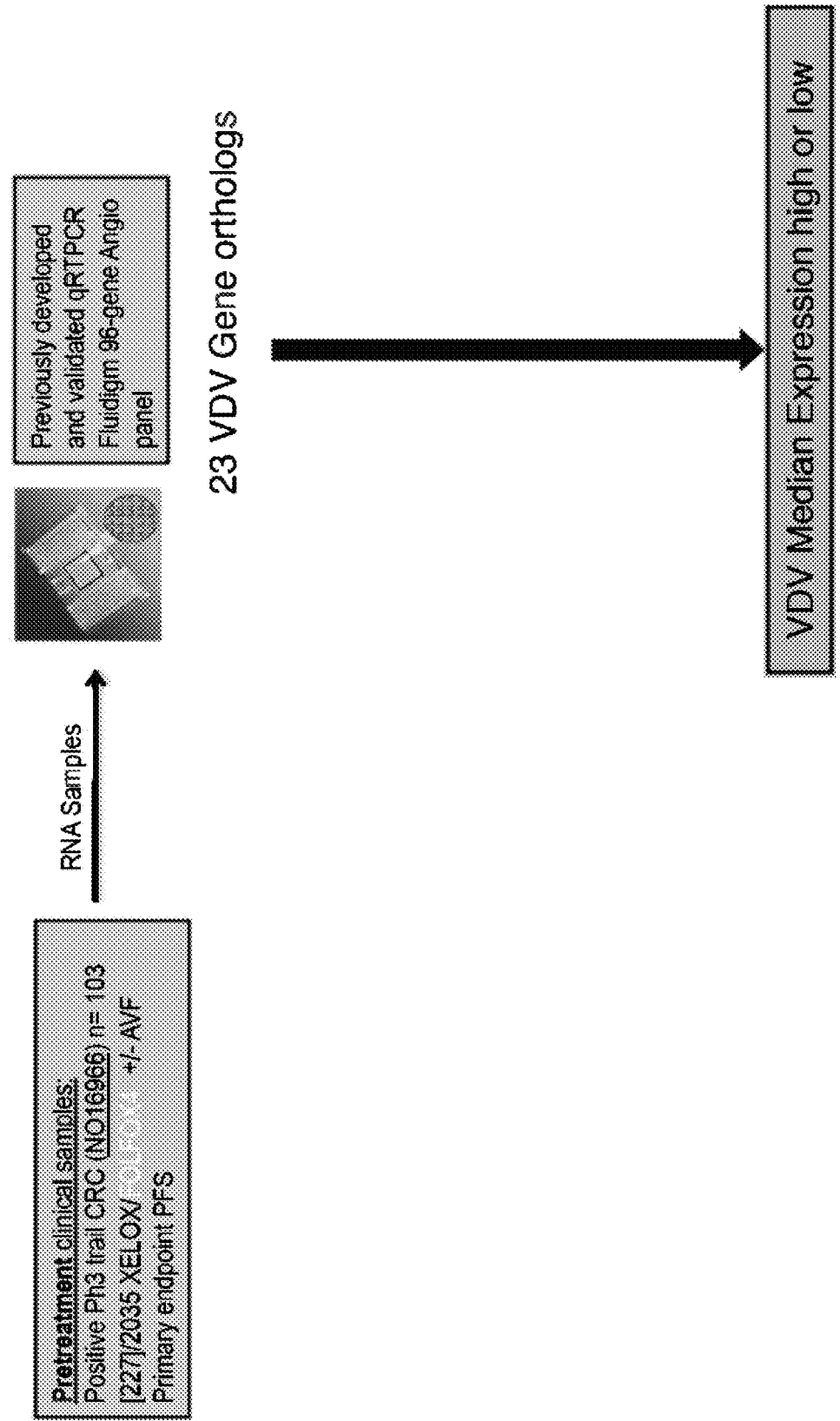
FIG. 8B is a schematic of the experiment overview for quantifying gene expression of 22 VDV genes using the angiogenesis Fluidigm qRT-PCR chip.
Figure 8C:
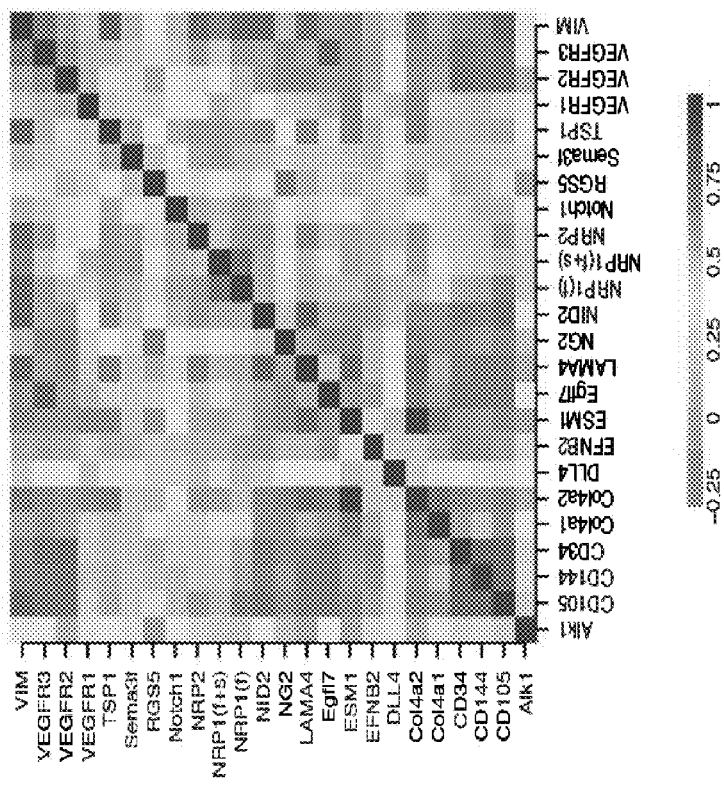
FIG. 8C is a graph showing the correlation of expression levels of the 22 VDV genes in colon cancer samples.
Figure 8D:
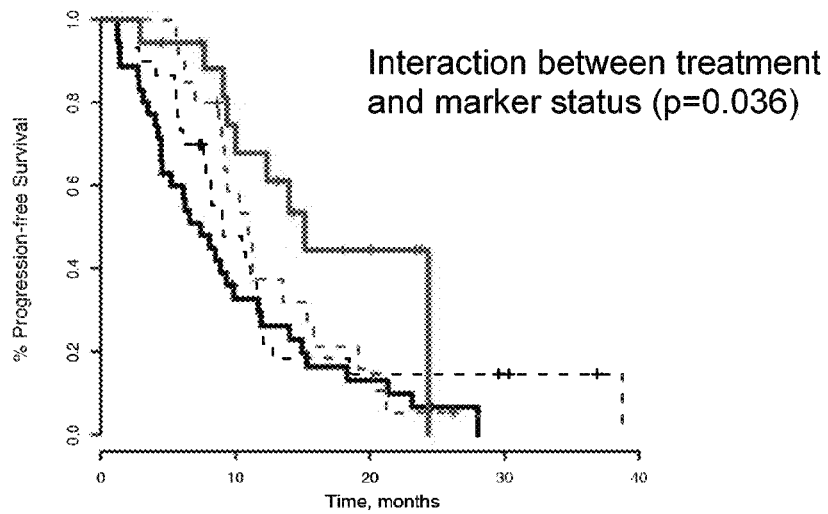
FIG. 8D is a set of graphs showing the 22-gene VDV signature stratifies the effect of bevacizumab (bev) treatment for patients with advanced colorectal cancer. Shown are progression-free (top) or overall survival (bottom) of "VDV-high" (solid lines) versus "VDV-low" patients (dashed lines), which were treated with XELOX (black) or XELOX+ bevacizumab (Mullen et al. *Cell.* 147(3): 565-576, 2011). PFS (top) VDV gene set effect, stratified by expression levels (interaction p=0.036), and OS (bottom) VDV gene set effect stratified by expression levels (interaction p=0.37).
Figure 8D:
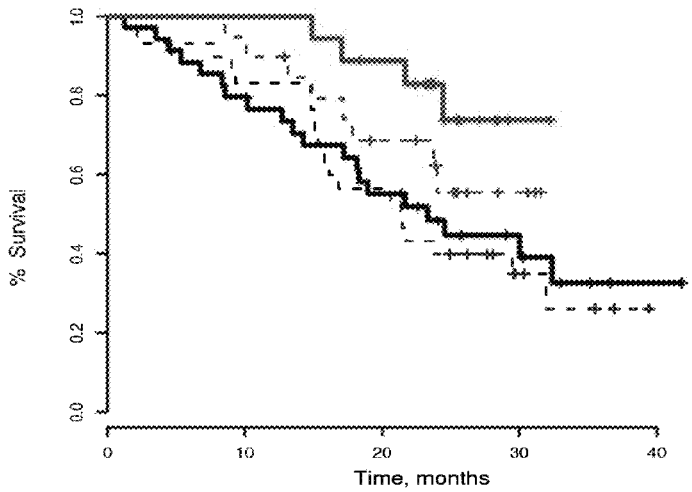
Figure 9A:
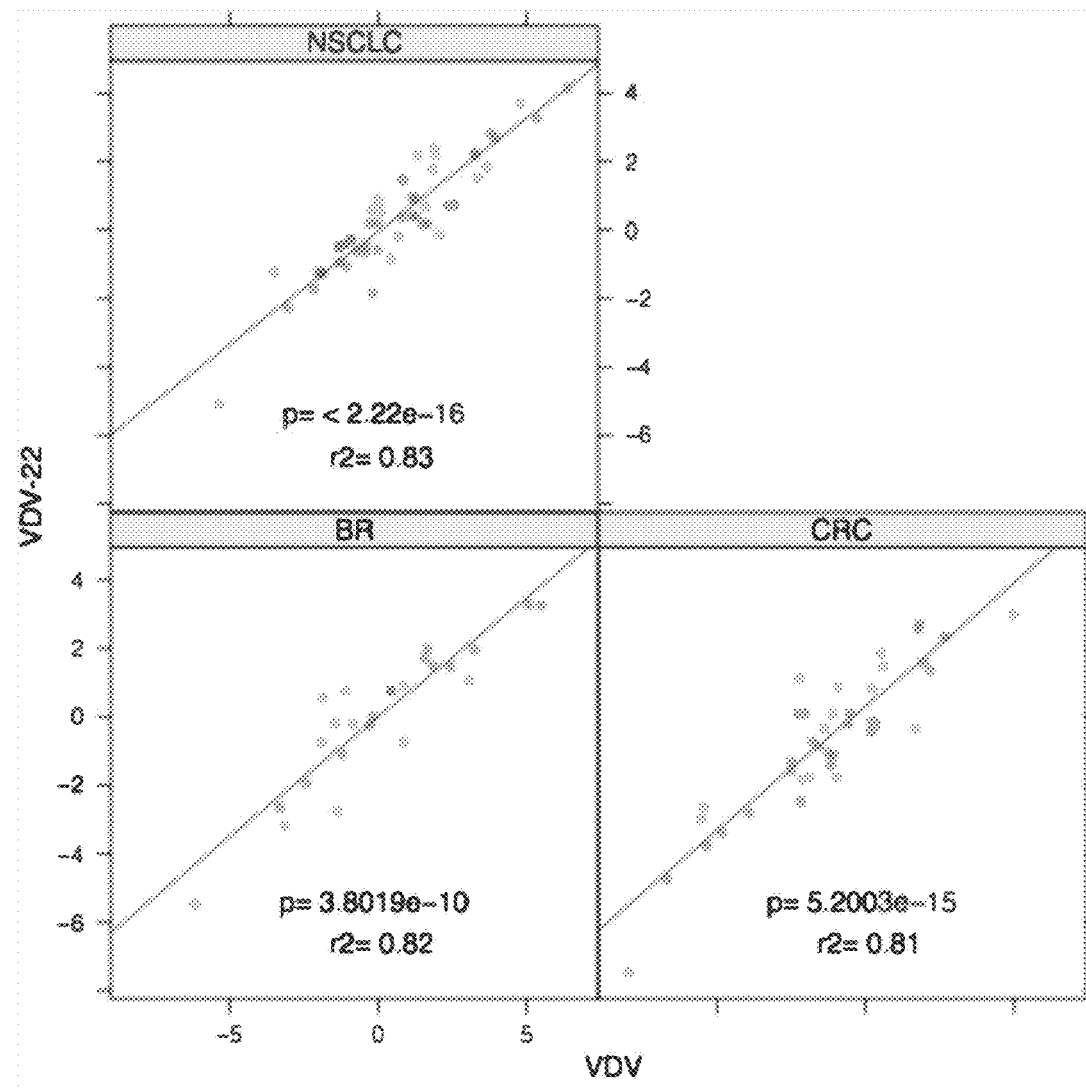
FIG. 9A is a set of graphs verifying concordance between the full VDV signature "VDV" (x-axis) and the 22-gene representative subset "VDV-22" (y-axis) used to interrogate archival clinical material. A prevalence sample set is shown with archival samples from patients that would qualify for metastatic first line trial setting (comparable to NO16966). Archival samples were assessed for whole genome RNA expression on Illumina DASL bead arrays; NSCLC=Non-small cell lung carcinoma, BR=Breast, CRC=Colorectal carcinoma.
Figure 9B:
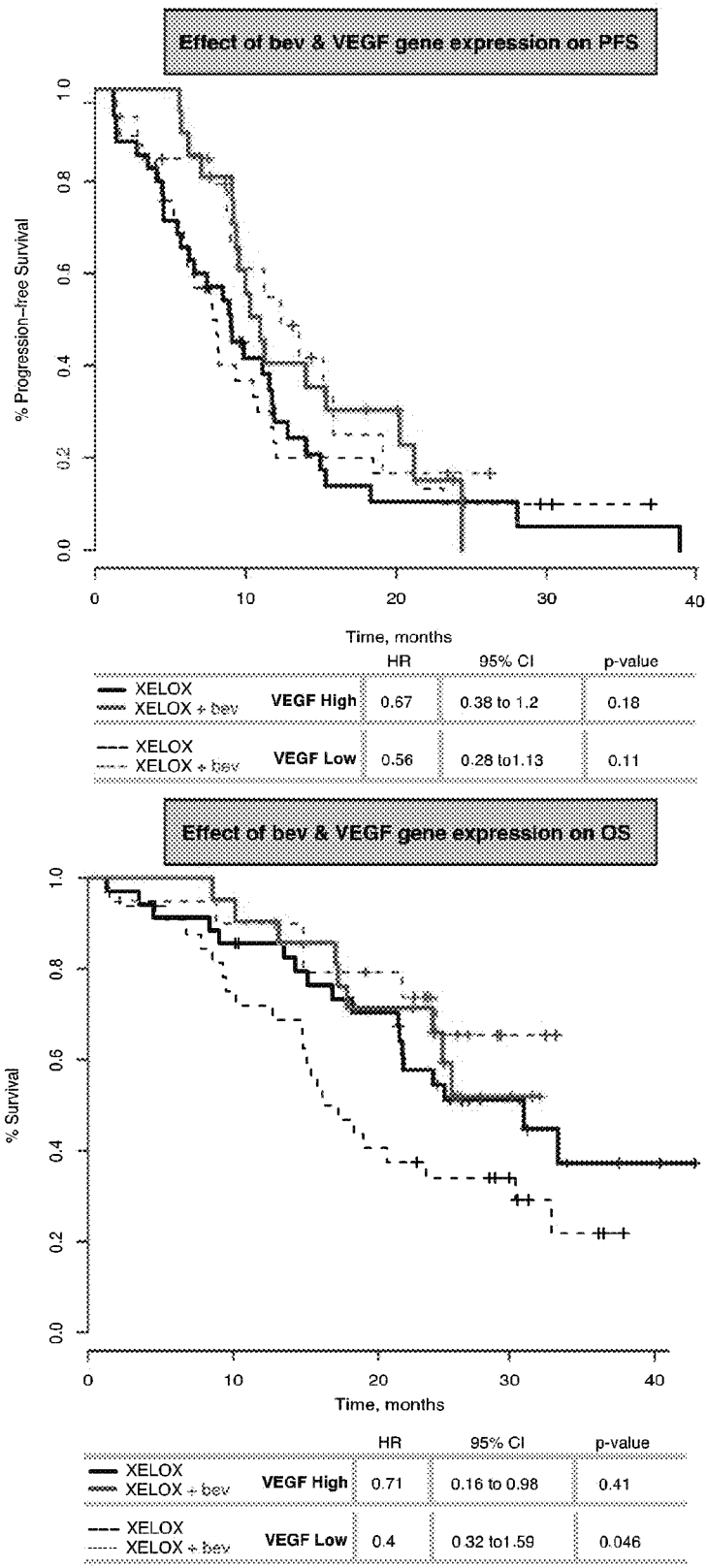
FIG. 9B is a set of graphs showing the stratification of NO 16966 patients by VEGF-A expression levels, PFS (upper), interaction p=0.76 and OS (below), interaction p=0.33.
Figure 9C:
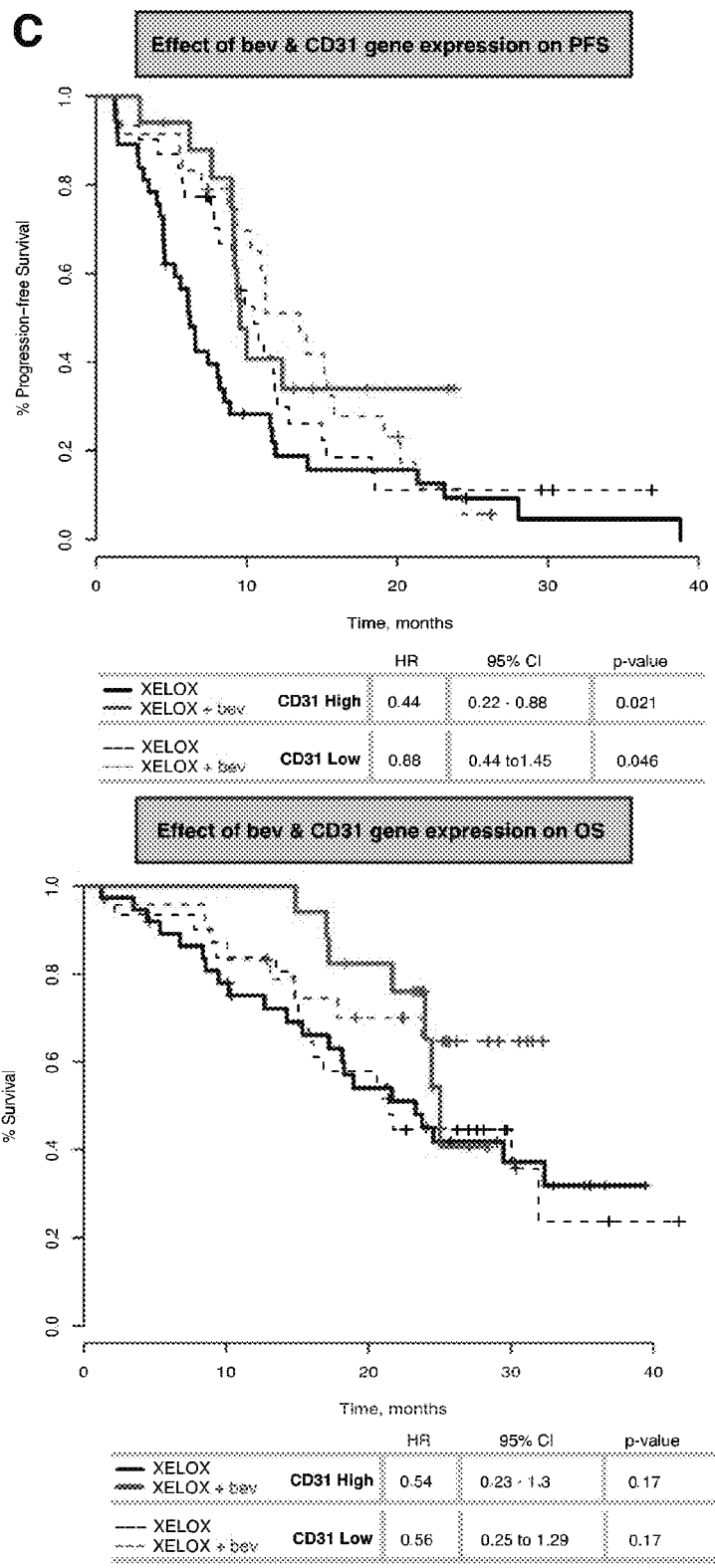
FIG. 9C is a set of graphs showing the stratification of NO 16966 patients by CD31 expression levels, PFS (upper) interaction p=0.15 and OS (lower), interaction p=0.99.

FIG. 8A shows the Kaplan-Meier analysis of OS and PFS in the 103 patients from the NO16966 trial examined in this study. In these patients, the addition of bevacizumab to chemotherapy provided a statistically significant PFS(HR, 0.59; 95% CI, 0.37 to 0.93; p=0.024) and OS benefit (HR, 0.45; 95% CI, 0.23 to 0.85; p=0.015). Since preliminary experiments in colon cancer prevalence samples indicated that the expression of these 22 VDV genes is highly correlated (FIG. 8C), we decided to use the median expression level of either an individual gene or a median expression score for the 22 VDV gene subset as a basis to classify the CRC samples as either "high" or "low" in each case (FIG. 8B). We then tested the correlation between clinical outcomes and "high" or "low" pre-treatment gene expression. As previously reported, the stratification of the treatment cohorts by pre-treatment VEGF mRNA levels alone did not show differential effects on clinical outcomes in the bevacizumab treated patients (FIG. 9B). Also, bevacizumab-treated patients classified into "high" and "low" subsets by the expression levels of a single distVDV gene (CD31) did not show differences in PFS; although there was a trend in OS benefit (FIG. 9C). In either case, the interaction between VEGF or CD31 and treatment did not show any predictive effect. Notably, when the same patient population was stratified into "VDV high" vs. "VDV low" populations (FIG. 8D), the effect size and significance altered substantially as compared to the baseline analysis: in "VDV low" patients (dotted lines in FIG. 8D), the combination of bevacizumab and chemotherapy conferred modest gains as compared to chemotherapy alone in both PFS(HR, 0.88; 95% CI, 0.47 to 1.62; p=0.67) and OS(HR, 0.58; 95% CI, 0.25 to 1.33; p=0.2). In contrast, in "VDV high" patients (FIG. 8D, solid lines), the addition of bevacizumab to chemotherapy vs chemotherapy alone provided a marked and significant PFS(HR, 0.36; 95% CI, 0.17 to 0.77; p=0.0079) and OS(HR, 0.31; 95% CI, 0.11 to 0.93; p=0.036) benefit. The interaction between treatment and marker status shows a significant predictive effect for PFS (p=0.036), but despite the observed improvement in relative risk in the "VDV high" patients, did not reach statistical significance for OS (p=0.37). Thus, in this relatively small 103-patient sample set, the higher expression of a collective VDV gene subset correlates specifically with the improved clinical outcome provided by bevacizumab addition to chemotherapy, and has a predictive effect with respect to PFS.

Example 7. Monitoring Patient Responsiveness or Sensitivity to a VEGF Antagonist This example describes an assay to monitor whether a patient will be responsive or sensitive to a VEGF antagonist. A sample (e.g., blood or tissue biopsy) is obtained, with informed consent, from one or more patients before treatment with a VEGF antagonist (e.g., an anti-VEGF antibody). DNA and serum/plasma are isolated, according to well known procedures. The samples may be pooled or maintained as individual samples.

The expression of at least one gene set forth in Table 1 or 2 is assessed by measuring mRNA for the at least one gene or by detecting protein encoded by the at least one gene using an ELISA as described above, with the following substitutions: (1) human gene (e.g., Nid2) standards for murine gene (e.g., Nid2) standards; (2) biotinylated goat anti-human gene (e.g., Nid2) polyclonal antibodies for biotinylated goat anti-mouse gene (e.g., Nid2) polyclonal Ab; and (3) 10% FBS for 0.5% BSA. Patients whose samples exhibit at least a two-fold increase in expression of the at least one gene relative to a control as described herein are identified as patients responsive or sensitive to treatment with VEGF antagonists.

Although the foregoing invention has been described in some detail by way of illustration and example for purposes of clarity of understanding, the descriptions and examples should not be construed as limiting the scope of the invention. The disclosures of all patents, patent applications, scientific references, and Genbank Accession Nos. cited herein are expressly incorporated by reference in their entirety for all purposes as if each patent, patent application, scientific reference, and Genbank Accession No. were specifically and individually incorporated by reference. Such patent applications specifically include U.S. Provisional Patent Application No. 61/586,660, filed on Jan. 13, 2012, from which this application claims benefit.

The invention claimed is:

1. A method of optimizing therapeutic efficacy of a VEGF antagonist for a patient, the method comprising:
    (a) detecting expression of at least three genes set forth in Table 2 in a sample obtained from the patient prior to any administration of a VEGF antagonist to the patient;
    (b) comparing the expression level of the at least three genes to a reference expression level of the at least three genes, wherein a change in the level of expression of the at least three genes in the patient sample relative to the reference expression level identifies a patient who is likely to respond to treatment with a VEGF antagonist; and
    (c) administering a VEGF antagonist to the patient identified in step (b) as likely to respond to treatment with a VEGF antagonist,
        wherein the VEGF antagonist is an anti-VEGF antibody and the change in the level of expression of the at least three genes in the patient sample is an increase relative to the reference expression level.

2. A method for treating an angiogenic disorder in a patient, the method comprising:
    (a) determining that a sample obtained from the patient has a level of at least three genes set forth in Table 2 that is above a reference expression level of the at least three genes; and
    (b) administering an effective amount of a VEGF antagonist,
        wherein the VEGF antagonist is an anti-VEGF antibody.

3. A method of treating a patient identified as likely to respond to treatment with a VEGF antagonist, the method comprising:
    (a) detecting expression of at least three genes set forth in Table 2 in a sample obtained from the patient prior to any administration of a VEGF antagonist to the patient;
    (b) comparing the expression level of the at least three genes to a reference expression level of the at least three genes, wherein a change in the level of expression of the at least three genes in the patient sample relative to the reference expression level identifies a patient who is likely to respond to treatment with a VEGF antagonist; and
    (c) administering a VEGF antagonist to the patient identified in step (b) as likely to respond to treatment with a VEGF antagonist,
        wherein the VEGF antagonist is an anti-VEGF antibody and the change in the level of expression of the at least three genes in the patient sample is an increase relative to the reference expression level.

4. The method of any one of claims 3, 1, and 2, wherein the anti-VEGF antibody is bevacizumab.

5. The method of claim 3 or 1, wherein the patient has an angiogenic disorder.

6. The method of claim 5, wherein the angiogenic disorder is a cancer selected from the group consisting of: colorectal cancer, breast cancer, lung cancer, glioblastoma, and combinations thereof.

7. The method of claim 3, wherein the patient is in a population of patients being tested for responsiveness to a VEGF antagonist and the reference expression level is the median level of expression of the at least three genes in the population of patients.

8. The method of claim 3, wherein expression of the at least three genes in the sample obtained from the patient is detected by measuring mRNA.

9. The method of claim 3, wherein expression of the at least three genes in the sample obtained from the patient is detected by measuring plasma protein levels.

10. The method of claim 3, wherein the sample is tumor tissue.

11. The method of claim 3, further comprising detecting expression of at least a fourth gene set forth in Table 2 in the sample from the patient.

12. The method of claim 3, wherein the change in the level of expression of the at least three genes in the patient sample relative to the reference expression level is determined by calculating a VDV signature score ($VDV_i$) for the patient sample according to the algorithm:

$$VDV_i = \frac{1}{\sqrt{n}} \sum_{g=1}^{n} Z_{g,i}$$

wherein $Z_{g=1,i}, Z_{g=2,i}, \ldots Z_{g=n,i}$ are standardized z-scores of expression values for each gene g, from g=1 to g=n, of the sample i, and
wherein a $VDV_i$ below a first defined threshold indicates a decrease relative to the reference expression level, and a $VDV_i$ above a second defined threshold indicates an increase relative to the reference expression level.

13. The method of claim 12, wherein the expression values for each gene g, from g=1 to g=n, are qRT-PCR values for each gene g, from g=1 to g=n.

14. The method of claim 12, wherein the first defined threshold is from −4 to −0.5 and the second defined threshold is from 0.5 to 4.

15. The method of claim 14, wherein the first defined threshold is from −4 to −1 and the second defined threshold is from 1 to 4.

16. The method of claim 15, wherein the first defined threshold is from −4 to −1.5 and the second defined threshold is from 1.5 to 4.

17. The method of claim 16, wherein the first defined threshold is from −4 to −2 and the second defined threshold is from 2 to 4.

* * * * *

UNITED STATES PATENT AND TRADEMARK OFFICE
CERTIFICATE OF CORRECTION

PATENT NO. : 10,364,466 B2
APPLICATION NO. : 13/836535
DATED : July 30, 2019
INVENTOR(S) : Bais et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 318 days.

Signed and Sealed this
Sixth Day of December, 2022

Katherine Kelly Vidal
*Director of the United States Patent and Trademark Office*